(12) United States Patent
Koya

(10) Patent No.: US 7,939,564 B2
(45) Date of Patent: May 10, 2011

(54) COMBINATION WITH BIS(THIOHYDRAZIDE AMIDES) FOR TREATING CANCER

(75) Inventor: Keizo Koya, Chestnut Hill, MA (US)

(73) Assignee: Synta Pharmaceuticals Corp., Lexington, MA (US)

( * ) Notice: Subject to any disclaimer, the term of this patent is extended or adjusted under 35 U.S.C. 154(b) by 0 days.

(21) Appl. No.: 11/897,538

(22) Filed: Aug. 30, 2007

(65) Prior Publication Data

US 2008/0119440 A1 May 22, 2008

Related U.S. Application Data

(60) Provisional application No. 60/841,570, filed on Aug. 31, 2006.

(51) Int. Cl.
A61K 31/16 (2006.01)
(52) U.S. Cl. .................................. 514/599; 514/562
(58) Field of Classification Search .................. None
See application file for complete search history.

(56) References Cited

U.S. PATENT DOCUMENTS

| | | | |
|---|---|---|---|
| 4,012,360 A | 3/1977 | Schwarzenbach et al. |
| 4,822,777 A | 4/1989 | Abra |
| 4,826,866 A | 5/1989 | Taylor et al. |
| 5,300,278 A | 4/1994 | Pasqualini et al. |
| 5,498,421 A | 3/1996 | Grinstaff et al. |
| 5,560,933 A | 10/1996 | Soon Shiong et al. |
| 5,665,382 A | 9/1997 | Grinstaff et al. |
| 5,739,686 A | 4/1998 | Naughn et al. |
| 5,753,200 A | 5/1998 | Zolotoochin et al. |
| 5,840,746 A | 11/1998 | Ducharme |
| 5,843,400 A | 12/1998 | Fujibayashi et al. |
| 5,916,596 A | 6/1999 | DeSai et al. |
| 6,013,836 A | 1/2000 | Hsu et al. |
| 6,096,331 A | 8/2000 | DeSai et al. |
| 6,172,108 B1 | 1/2001 | Vega et al. |
| 6,172,188 B1 | 1/2001 | Thastrup et al. |
| 6,214,863 B1 | 4/2001 | Bissery et al. |
| 6,235,787 B1 | 5/2001 | Broadhurst et al. |
| 6,365,745 B1 | 4/2002 | Matsui et al. |
| 6,399,659 B2 | 6/2002 | Usui et al. |
| 6,435,787 B1 | 8/2002 | John |
| 6,455,515 B2 | 9/2002 | Gypser et al. |
| 6,506,405 B1 | 1/2003 | DeSai et al. |
| 6,537,579 B1 | 3/2003 | DeSai et al. |
| 6,656,971 B2 | 12/2003 | Wu et al. |
| 6,703,426 B1 | 3/2004 | Miles et al. |
| 6,749,868 B1 | 6/2004 | DeSai et al. |
| 6,753,006 B1 | 6/2004 | DeSai et al. |
| 6,762,204 B2 | 7/2004 | Koya et al. |
| 6,800,660 B2 | 10/2004 | Koya et al. |
| 6,809,119 B2 | 10/2004 | Hu et al. |
| 6,825,235 B2 | 11/2004 | Chen et al. |
| 6,897,335 B2 | 5/2005 | Okabe et al. |
| 6,924,312 B2 | 8/2005 | Koya et al. |
| 7,001,923 B2 | 2/2006 | Koya et al. |
| 7,037,940 B2 | 5/2006 | Koya et al. |
| 7,074,952 B2 | 7/2006 | Chen et al. |
| 7,250,432 B2 | 7/2007 | Kwon |
| 7,345,094 B2 | 3/2008 | Koya et al. |
| 7,368,473 B2 | 5/2008 | Koya et al. |
| 7,385,084 B2 | 6/2008 | Koya et al. |
| 7,435,843 B2 | 10/2008 | Chen et al. |
| 2002/0198160 A1 | 12/2002 | Everitt et al. |
| 2004/0022869 A1 | 2/2004 | Chen et al. |
| 2004/0225016 A1 | 11/2004 | Koya et al. |
| 2004/0235813 A1 | 11/2004 | Wanker et al. |
| 2005/0154039 A1 | 7/2005 | Glacera Contour |
| 2006/0142386 A1 | 6/2006 | Barsoum |
| 2006/0142393 A1 | 6/2006 | Sherman et al. |
| 2006/0167106 A1 | 11/2006 | Zhang et al. |
| 2006/0270873 A1 | 11/2006 | Chen et al. |
| 2006/0281811 A1 | 12/2006 | Chen et al. |
| 2007/0088057 A1 | 4/2007 | Lusmann et al. |
| 2008/0089950 A1 | 4/2008 | Chen et al. |
| 2008/0118562 A1 | 5/2008 | Koya |
| 2008/0119440 A1 | 5/2008 | Koya |
| 2008/0146842 A1 | 6/2008 | Koya et al. |
| 2008/0176828 A1 | 7/2008 | Koya et al. |
| 2008/0214655 A1 | 9/2008 | Koya et al. |
| 2008/0226588 A1 | 9/2008 | McLeod |
| 2008/0242702 A1 | 10/2008 | Koya et al. |
| 2008/0269340 A1 | 10/2008 | Koya et al. |
| 2009/0005594 A1 | 1/2009 | Chen et al. |
| 2009/0023736 A1 | 1/2009 | Koya et al. |
| 2009/0042991 A1 | 2/2009 | Barsoum |
| 2009/0093538 A1 | 4/2009 | Bertin et al. |
| 2009/0137682 A1 | 5/2009 | Dahl |

FOREIGN PATENT DOCUMENTS

AU 2006-228035 A1 10/2006
(Continued)

OTHER PUBLICATIONS

Sausville et al., Contributions of human tumor xenografts to anticancer drug development. Cancer Research, 66:3351-3354, 2006.*
Johnson et al., Relationship s between drug activity in NCI preclinical in vitro and in vivo models and early clinical trials. Br J Cancer, 84(10):1424-1431, 2001.*
Gavezzotti, "Are Crystal Structures Predictable?", Accounts of Chemical Research, 27:309-314, 1994.*
Vippagunta et al, "Crystalline Solids", Advanced Drug Delivery Reviews, 48: 3-26, 2001.*
Inclusion complex: Lewis, Hawley's Condensed Chemical Dictionary, 14th Edition, 1997, Van Nostrand Reinhold.*
Hoffman, Henry, published online Dec. 6, 2003 in Wiley InterScience (www.interscience.wiley.com).*
Clathrate: Lewis, Hawley's Condensed Chemical Dictionary, 14th Edition, 1997, Van Nostrand Reinhold.*
Berge et al., J Pharm Sci, 66 (1): 1-19, 1977.*

*Primary Examiner* — Ardin Marschel
*Assistant Examiner* — Bong-Sook Baek
(74) *Attorney, Agent, or Firm* — Steven G. Davis

(57) ABSTRACT

Disclosed herein are methods of treating a proliferative disease, such as cancer, with bis(thio-hydrazide amides) or a tautomer, pharmaceutically acceptable salt, solvate, clathrate, or prodrug thereof, in combination with hyperthermia treatment. Also disclosed are methods of treating a proliferative disease, such as cancer, with bis(thio-hydrazide amides) or a tautomer, pharmaceutically acceptable salt, solvate, clathrate, or prodrug thereof, in combination with radiotherapy.

4 Claims, 8 Drawing Sheets

FOREIGN PATENT DOCUMENTS

| | | |
|---|---|---|
| AU | 2006/228035 A1 | 11/2006 |
| CH | 482394 A | 12/1969 |
| DE | 2037257 | 2/1972 |
| EP | 1454628 | 9/2004 |
| EP | 1493445 A1 | 1/2005 |
| EP | 1406869 B1 | 9/2006 |
| EP | 1731148 A1 | 12/2006 |
| EP | 1845083 | 10/2007 |
| FR | 2097737 | 4/1972 |
| GB | 1272920 | 5/1972 |
| JP | 50-91056 | 7/1975 |
| JP | 63-267752 | 11/1988 |
| JP | 07-165693 | 6/1995 |
| JP | 10-501215 | 2/1998 |
| WO | WO 94/10995 | 5/1994 |
| WO | WO 99/34796 | 7/1999 |
| WO | WO 03/006428 | 1/2003 |
| WO | WO 03/006428 A | 1/2003 |
| WO | WO 03/006429 | 1/2003 |
| WO | WO 03/006430 | 1/2003 |
| WO | WO 03/047524 | 6/2003 |
| WO | WO 2004/064826 | 8/2004 |
| WO | WO 2004/064826 A1 | 8/2004 |
| WO | WO 2004/072051 | 8/2004 |
| WO | WO 2005/028475 A2 | 3/2005 |
| WO | WO 2005-097758 A1 | 10/2005 |
| WO | WO 2006/009940 | 1/2006 |
| WO | WO 2006/033913 | 3/2006 |
| WO | WO 2006/055747 | 5/2006 |
| WO | WO 2006/055747 A2 | 5/2006 |
| WO | WO 2006/062732 A2 | 6/2006 |
| WO | WO 2006/089177 A2 | 8/2006 |
| WO | WO 2006/113493 | 10/2006 |
| WO | WO 2006/113493 A2 | 10/2006 |
| WO | WO 2006/113572 | 10/2006 |
| WO | WO 2006/113572 A1 | 10/2006 |
| WO | WO 2006/113695 | 10/2006 |
| WO | WO 2006/113695 A1 | 10/2006 |
| WO | WO 2006/124736 | 11/2006 |
| WO | WO 2007/021881 | 2/2007 |
| WO | WO 2008/024298 | 2/2008 |
| WO | WO 2008/024298 A1 | 2/2008 |
| WO | WO 2008/024299 | 2/2008 |
| WO | WO 2008/024301 | 2/2008 |
| WO | WO 2008/024301 A2 | 2/2008 |
| WO | WO 2008/024302 | 2/2008 |
| WO | WO 2008/024303 | 2/2008 |
| WO | WO 2008/024303 A2 | 2/2008 |
| WO | WO 2008/024305 | 2/2008 |
| WO | WO 2008/027445 | 3/2008 |
| WO | WO 2008/027445 A2 | 3/2008 |
| WO | WO 2008/033300 | 3/2008 |
| WO | WO 2008/033449 A2 | 3/2008 |
| WO | WO 2008/033494 | 3/2008 |
| WO | WO 2008/082579 A1 | 7/2008 |
| WO | WO 2008/136976 A2 | 11/2008 |
| WO | WO 2009/020631 | 2/2009 |
| WO | WO 2009/064374 A2 | 5/2009 |
| WO | WO 2009/073147 | 6/2009 |
| WO | WO 2009/073148 | 6/2009 |

OTHER PUBLICATIONS

Gehrmann, Mathias, "Drug Evaluation: STA-4783—Enhancing Taxane Efficacy by Induction of Hsp70," *Current Opinion in Investigational Drugs*, 7(6): 574-580 (Jun. 2006).

"Principals of Cancer Therapy," *The Merck Manual*, Merck Research Laboratories, 987-995 (1999).

Wust, P., et al., "Hyperthermia in Combined Treatment of Cancer," *Lancet Onocology*, 3(8): 487-497 (Aug. 2002).

Valeriote, F., et al. "Synergistic Interaction of Anticancer Agents: A Cellular Perspective," *Cancer Chemotherapy Reports.*, 59(5): 895-900 (1975).

Savage, E., et al., "Living with Melanoma," [online], [retrieved on Aug. 9, 2006]. Retrieved from the Internet URL: http://ericandfran.com/melanona.htm.

Garlock, K., "Experimental Treatment Gives a Cancer Patient Hope," *The Charlotte Observer* [online], Apr. 25, 2005 [retrieved on May 23, 2008]. Retrieved from the Internet URL: http://www.ericandfran.com/charlotte_observer_april_25.htm.

"Hyperthermia in Cancer Treatment: Questions and Answers," *FactSheet*, National Cancer Institute, [online], Aug. 12, 2004 [retrieved on Dec. 12, 2008]. Retrieved from the Internet URL: www.cancer.gov/PDF/FactSheet/fs7_3.pdf.

V. Bradova, "Hyperthermia," [online], Dec. 25, 1998 [retrieved on Dec. 12, 2008]. Retrieved from the Internet URL: http://www.geocities.com/hotsprings/villa/5443/alts/hytherm.html.

J. Radons, et al., "Immunostimulatory Functions of Membrane-Bound and Exported Heat Shock Protein 70," *Exerc Immunol Rev.*, 2005;11:17-33.

Search Report in international application PCT/US2007/019021 (May 2008).

Badawy, M. A., "Synthesis and Reactions of 1,2,4-Triazino-1,2,4-Triazines," *Sulfur Letters* 11(1+2):21-28 (1990).

Baker, W., et al., "663: 1 : 4-Diaryl-1: 4-dihydro-1 : 2 : 4 : 5-tetrazines and Derived Substances," *Journal of the Chemical Society*, 3389-3394 (1950).

Barta-Szalai, G., et al., "Electron Deficient Heteroaromatic Ammonioamidates. XVII. N-(3-Quinazolinio)amidates. VI. The Photochemistry of N-(3-Quinazolinio)amidates in the Presence of ÿ-Toluenethiol," *Acta Chemica Scandinavica B* 33:79-85 (1979).

Branch, C. L., et al., "Synthesis of 6-Hydroxy-2-Methyl-3-Thioxo-2H-1,2,4-Triazin-5-one," *Synthetic Communications* 26(11):2075-2084 (1996).

Cava, M.P., et al., "Thionation Reactions of Lawesson's Reagents," *Tetrahedron*, 14(22): 5061-5087 (1985).

El-Barbary, A.A., et al., "Studies in Organophosphorus Compounds," *Tetrahedron*, 36: 3309-3315 (1980).

Heindel, N.D., et al., "Thiohydrazides and Acetylene Esters, A New Route to 1,3,4-Thiadiazoles," *Journal of Heterocyclic Chemistry*, 17(1): 191-193 (1980).

Henderson, N. D. et al., "Synthesis of new bifunctional compounds which selectively alkylate guanines in DNA," *Anti-Cancer Drug Design*, 13:749-768 (1998).

Jensen, K. A., et al., "Thiohydrazides and Thiohydrazones: A New Class of Antibacterial Substances," *Acta Chemica Scandinavica*, 6(*Pt. II*): 957-958 (1952).

Mohamed, M. M., et al., "Synthesis & Some Reactions of 2-(alβ-Naphthyl)-3,1-benzoxazin-4(*H*)-ones 3-Amino-2-(ÿ-naphthyl)quinazolin-4(3*H*)-one," *Indian Journal of Chemistry* 25B(2):207-211 (1986).

Molina, P., et al., "Methyl 2-Methyldithiocarbazate in Heterocyclic Synthesis: Preparation of 2,5-Disubstituted 1,3,4-Thiadiazoles, Bis(1,3,4-Thiadiazolium) Salts and Macrocycles containing 1,3,4-Thiadiazole Subunits, X-Ray Crystal Structure of 2,2'-Bis[4,5-dihydro-5-(2-hydroxyethylimino)-4-methyl-1,3,4-thiadiazole]," *J. Chem. Soc. Perkin Trans. 1 s* 5:1159-1166 (1991).

Molina, P., et al., "Preparation of a Novel Type of Ligands Incorporating Two or Three 1,3,4-Thiadiazole Units," *Heterocycles* 36(6):1263-1278 (1993).

Przheval, N. M., et al., "A New General Synthesis of Bistetrafluoroborates of 2,3,4,5-Tetrasubstituted 1,3,4-Thiadiazoliums," *Synthesis* 5:463-464 (1993).

Rupp, W., "5-Amino-1,3,4-Thiadiazole Compounds," CA76:126992 (1972).

Sato, T., et al., "Studies in Organic Sulfur Compounds. I. Thioformyl Phenylhydrazide," *Bulletin of the Chemical Society of Japan*, 27(9): 624-627 (1954).

Schwarz, J. and Just, H., "Virustatic Thiosemicarbazides," CA77:48081 (1972).

Tsuji, T., et al., "Synthesis and Reactions of N-Aminothiouracils and Thiadiazolo [3,2-ÿ] pyrimidinones," *Chem. Pharm. Bull.* 26(9):2765-2767 (1978).

Ueda, H. and Ohta, M., "Studies on Sulfur-Containing Heterocyclic Compounds," *Nippon Kagaku Zasshi*, 80:571-574 (1959).

Walter, W., et al., "Chapter 9: The Chemistry of the Thiohydrazide Group," *The Chemistry of Amides* (Ed. J. Zabicky), (London: Interscience Publishers), pp. 477-514 (1970).

"The Merck Manual," Chapter 14: Principles of Cancer Therapy, 1999 Merck Research Laboratories, pp. 987-995 (1999), XP002477370.

Abuchowski, A., et al.,"Alteration of Immunological Properties of Bovine Serum Albumin by Covalent Attachment of Polyethylene Glycol," The *Journal of Biological Chemistry* 252(11):3578-3581 (1977).

Al-Talib, M. et al., "Diacyl Acid Dihydrazides," *Magnetic Resonance in Chemistry*, 28: 1072-1078 (1990).

Asahi Chemical Ind. K.K. Abstract of Japanese Patent No. 50-91056, Accession No. 47521Y/27 (1975).

Ashburner, M. and Bonner, J.J., "The Induction of Gene Activity in *Drosophila* by Heat Shock," *Cell*, 17: 241-254 (1979).

Atherton, F.R., et al., "Synthesis of 3(S)-Acylamino-1-[(Phenyl)(1H-Tetrazol-5-YL)Amino]-2-Azetidinones," *Tetrahedron*, 39(15): 2599-2608 (1983).

Auluck, P.K., et al., "Chaperone Suppression of α-Synuclein Toxicity in a *Drosophila* Model for Parkinson's Disease," *Science*, 295: 865-868 (2002).

Bahceci, et al., "Reactions of amidines with some carboxylic acid hydrazides," Indian Journal of Chemistry Section B, vol. 44B, 2005, pp. 568-572, XP009083365, p. 569, Scheme 1.

Chuyguk, V. A. and Nemazanyj A.G., "Mesoionic Methine Dyes from Biquaternary Salts of Dihetarylmethanes-1,3,4-Oxa(thia)diazoles and 1,2,4-Triazoles Derivatives," *Ukr. Khim. Zhurn.* 48:520 (1984). Translation submitted in U.S. Appl. No. 10/193,075, filed Jul. 10, 2002.

Clathrate: Lewis, Hawley's Condensed Chemical Dictionary, 14th Edition, 1997, Van Nostrand Reinhold.

Craig, E. A., "The Heat Shock," *Crit. Rev. Biochem.*, 18(3): 239-280 (1985).

Daniels, G., et al., "A simple method to cure established tumors by inflammatory killing of normal cells," Nature Biotechnoloyg, Sep. 2004, 22(9), 1125-1132 (Epub Aug. 1, 2004).

Doi, Y., et al., "Effect of HSP70 Induced by Warm Ischemia to the Liver on Liver Function after Partial Hepatectomy," *Hepato-Gastroenterology*, 48: 533-540 (2001).

Dunn, S.E., et al., "Polystyrene-Poly (Ethylene Glycol) (PS-PEG2000) Particles as Model Systems for Site Specific Drug Delivery. 2. The Effect of PEG Surface Density on the in Vitro Cell Initeraction and in Vivo Biodistribution," *Pharmaceutical Research* 11(7):1016-1022 (1994).

Dvorak, H.F., et al., "Identification and Characterization of the Blood Vessels of Solid Tumors That Are Leaky to Circulating Macromolecules," *American Journal of Pathology* 133(1):95-109 (1988).

Balkwill, F. et al., "Inflammation and Cancer: Back to Virchow?" *The Lancet*, 357: 539-545 (Feb. 2001).

Gabizon, A.A., "Selective Tumor Localization and Improved Therapeutic Index of Anthracyclines Encapsulated in Long-Circulating Liposomes," *Cancer Research* 52:891-896 (1992).

Gao, Y., et al., "Protein Kinase C-dependent Activation of P44/42 Mitogen-activated Protein Kinase and Heat Shock Protein 70 in Signal Transduction During Hepatocyte Ischemic Preconditioning," *World J. Gastroenterol.*, 10(7): 1019-1027 (2004).

Gavezzotti, "Are crystal structures predictable?," Accounts of Chemical Research, 27:309-314, 1994.

Gehrmann, M., "Drug Evaluation: STA-4783—Enhancing Taxane Efficacy by Induction of Hsp70," *Current Opinion in Investigational Drugs*, 7(6): 574-580 (Jun. 2006), XP008087326.

Georgopoulos, C. and Welch, W. J., "Role of the Major Heat Shock Proteins as Molecular Chaperones," *Annu. Rev. Cell Biol.*, 9: 601-634 (1993).

Golub et al., "Molecular Classification of Cancer: Class Discovery and Class Prediction by Gene Expression Monitoring," *Science*, 286, 1999, pp. 531-537.

Goodman & Gilman's, The Pharmacological Basis of Therapeutics, Ninth Edition, (1996), Section X, Calabresi et al., pp. 1225-1232.

Barclay, J.W. and Roberson,R.M., "Role for Calcium in Heat Shock-Mediated Synaptic Thermoprotection in *Drosophila* Larvae," *J. Neurobiol.*, 56(4): 360-371 (2003).

Barrett, William G. and McKay, Donald, "Decomposition and Cycloaddition Reactions of Some Bis(azodicarbonyl) Compounds," *Journal of Chem. Soc.*, (4): 1046-1052 (1975).

Gref, R., et al., "Biodegradable Long-Circulating Polymeric Nanospheres," *Science* 263:1600-1603 (1994).

Gura et al., "Systems for Identifying New Drugs are Often Faulty," *Science*, 1997, 278: 1041-1042.

Gurney, M. E., et al., "Motor Neuron Degeneration in Mice That Express a Human Cu,Zn Superoxide Dismutase Mutation," *Science*, 264: 1772-1775 (1994).

Barry, V.C. et al., "Anticancer Agents-III. Synthesis and Anticancer Activity of Some Bis-Thiosemicarbazones and Thiosemicarbazides," *Proc. R.I.A.*, 65: 309-324 (1967).

Beck, F-X., et al., "Molecular Chaperones in the Kidney: Distribution, Putative Roles, and Regulation," *Am. J. Physiol. Renal. Physiol.*, 279: F203-F215 (2000).

Hiratsuka, M., et al., "Heat Shock Pretreatment Protects Pulmonary Isografts from Subsequent Ischemia-reperfusion Injury," *J. Heart Lung Transplant*, 17(12): 1238-1246 (1998).

Holcomb, L., et al., "Accelerated Alzheimer-Type phenotype in transgenic mice carrying both mutant *amyloid precursor protein* and *presenilin I* transgenes," *Nature Medicine*, 4(1): 97-100 (1998).

Honshu Paper Mfg. Co. Ltd, Abstract of Japanese Patent No. 182050, published Feb. 13, 1996.

Howland, D. S., et al., "Focal Loss of the Glutamate Transporter Eaat2 in a Transgenetic Rat Model of Sod1 Mutant-mediated Amyotrophic Lateral Sclerosis (ALS)," *Proc. Nat. Acad. Sci. USA*, 99(3): 1604-1609 (2002).

Ichihara, et al., "Roles of oxidative stress and Akt signaling in doxorubicin cardiotoxicity," Biochemical and Biophysical Research Communications, Academic Press Inc., Orlando, FL, US, vol. 359, No. 1, Jun. 2, 2007, pp. 27-33, XP022103137, ISSN: 0006-291X.

Inclusion complex: Lewis, Hawley's Condensed Chemical Dictionary, 14th Edition, 1997, Van Nostrand Reinhold.

Ishii, Y., et al., "Retinal Ganglion Cell Protection with Geranylgeranylacetone, a Heat Shock Protein Inducer, in a Rat Glaucoma Model," *Invest. Opthalmol. Vis. Sci.*, 44(5): 1982-1992 (2003).

Jacquier-Sarlin, M.R. et al., "Protective Effects of hsp70 in Inflammation," *Experientia*, 50(11-12): 1031-1038 (Nov. 1994).

Beillerot, et al., "Synthesis and protective effects of coumarin derivatives against oxidative stress induced by doxorubicin," Bioorganic & Medicinal Chemistry Letters, Oxford, GB, vol. 18, No. 3, Dec. 27, 2007, pp. 1102-1105, XP022475694, ISSN: 0960-894X.

Johnson, A.D., et al., "Differential Distribution of 70-kD Heat Shock Protein Atherosclerosis," *Arterio Thromb Vasc Biol*, 15(1): 27-36 (1995).

Kandror, O. and Goldberg, A.L., "Trigger Factor is Induced Upon Cold Shock and Enhances Viability of *Escherichia coli* at Low Temperatures," *Proc Natl Acad Sci USA*, 94(10): 4978-4981 (1997).

Kelly, S. and Yenari, M.A., "Neuroprotection: Heat Shock Proteins," *Curr Res Med Opin*, 18(Suppl. 2): s55-s60 (2002).

Keswani, et al., "FK506 Is Neuroprotective in a Model of Antiretroviral Toxic Neuropathy," *Annals Neurology*, 53(1): 57-64 (2003).

Kiang, J.G. and Tsokos, G.C., "Heat Shock Protein 70 kDA: Molecular Biology, Biochemistry, and Physiology," *Pharmacol Ther*, 80(2): 183-201 (1998).

Klettner, A. and Herdegen, T., "The Immunophilin-Ligands FK506 and V-10,367 Mediate Neuroprotection by the Heat Shock Response," *Br J Pharmacol*, 138(5): 1004-1012 (2003).

Klettner, A., "The Induction of Heat Shock Proteins as a Potential Strategy to Treat Neurodegenerative Disorders," *Drug News Perspect*, 17(5): 299-306 (2004).

Klibanov, A., et al., "Amphipathic Polyethyleneglycols Effectively Prolong the Circulation Time of Liposomes," *FEBS* 268(1):235-237 (1990).

Kruse, L.I., et al., "Some Benzyl-Substituted Imidazoles, Triazoles, Terazoles, Pyridinethiones, and Structural Relatives as Multisubstrate Inhibitors of Dopamine β-Hydroxylase. 4.[1] Structure-Activity Relationships at the Copper Binding Site," *J. Med. Chem.*, 33: 781-789 (1990).

Langston, J.W., et al., "Selective Nigral Toxicity After Systemic Administration of 1-Methyl-4Phenyl-1,2,5,6-Tetrahydropyrine (MPTP) in the Squirrel Monkey," *Brain Res*, 292: 390-394 (1984).

Lee, J.E., et al., "Differential Neuroprotection From Human Heat Shock Protein 70 Overexpression in in Vitro and in Vivo Models of Ischemia and Ischemia-Like Conditions,"*Exp Neurol*, 170(1): 129-139 (2001).

Lepore, D.A., et al., "Role of Priming Stresses and Hsp70 in Protection From Ischemia-Reperfusion Injury in Cardiac and Skeletal Muscle," *Cell Stress & Chaperones*, 6(2): 93-96 (2001).

Lindquist, S., "The Heat-Shock Response," *Ann Rev Biochem*, 55: 1151-1191 (1986).

Longa, E.Z., et al., "Reversible Middle Cerebral Artery Occlusion Without Craniectomy in Rats," *Stroke*, 20(1): 84-91 (1989).

Malberg, J.E. and Seiden, L.S., Poster "MDMA Administration Induces Expression of HSP70 in the Rat Brain." Society for Neuroscience Annual Meeting, New Orleans, LA, Oct. 25-30, 1997.

Mangiarini, L., et al., "Exon 1 of the *HD* Gene With an Expanded CAG Repeat is Sufficient to Cause a Progressive Neurological Phenotype in Transgenic Mice," *Cell*, 87: 493-506 (1996).

Marber, M.S., et al., "Overexpression of the Rat Iducible 70-kD Heat Stree Protein in a Transgenic Mouse Increases the Resistance of the Heart to Ischemic Injury," *J Clin Invest*, 95: 1446-1456 (1995).

McCarthy, A.R., et al., "Cyclic Meso-ionic Compounds. Part IX.[1] Synthesis, Spectroscopic Properties, and Chemistry of 1,3,4-Thiadiazolium-2-olates and 1,3,4-Oxadiazolium-2-thiolates[2]," *J.C.S. Perkin I*, 627-632 (1974).

Merlin, J.-L. et al., "In vitro Comparative Evaluation of Trastuzumab (Herceptin®) Combined with Paclitaxel (Taxol®) or Docetaxel (Taxotere®) in HER2-Expressing Human Breast Cancer Cell Lines," Annals of Oncology, vol. 13: 1743-1748 (2002).

Bellmann, K., et al., "Heat Shock Induces Resistance in Rat Pancreatic Islet Cells against Nitric Oxide, Oxygen Radicals and Streptozotocin Toxicity In Vitro," *J. Clin. Invest.*, 95(6): 2840-2845 (1995).

Milas, et al., "Chemoradiotherapy: emerging treatment improvement strategies," published online Dec. 6, 2003 in Wiley InterScience (www.interscience.wiley.com).

Minowada, G. and Welch, W.J., "Clinical Implications of the Stress Response," *J Clin Invest*, 95: 3-12 (1995).

Mitsui Toatsu Chem. Inc., Abstract of Japanese Patent No. 308024, published Dec. 25, 1986. From Derwent Publications Ltd.

Bräuniger, H., "Hydrazide und Hydrazidderivate von Dicarbonsäuren," Pharmaceutical-Chemical Institute of University of Rostock, Supplied by the "British Library," *Pharmazie*, 25(5-6): 279-283 (1970).

Brittain et al., in *Polymorphism in Pharmaceutical Solids*, (NY: M. Dekker), vol. 95, pp. 348-361 (1999).

Calderwood, S., et al., "Extracellular heat shock proteins in cell signaling and immunity," Annals of the New York Academy of Sciences, Oct. 2007, 1113, 28-39.

Morimoto, et al., In: The Biology of Heat Shock Proteins and Molecular Chaperone. (NY: Cold Spring Harbor Laboratory Press) pp. 417-455 (1994).

Mosser, D.D., et al., "The Chaperone Function of hsp70 Is Required for Protecti Induced Apoptosis," *Mol Cell Biol*, 20(19): 7146-7159 (2000).

O'Callaghan, C.N., "Anticancer Agents-X. Cyclisation of 1-Acyl-4-Alkylthiosemicarbazide Derivatives to 1,2,4-Triazoline-3-Thiones in the Presence of Hydrazine," *Proc. R.I.A.*, 74: 455-461 (1974).

Papahadjopoulos, D., et al., "Sterically Stabilized Liposomes: Improvements in Pharmacokinetics and Antitumor Therapeutic Efficacy," *Proc. Natl. Acad. Sci. USA* 88:11460-11464 (1991).

Patani, et al., "Bioisosterism: A Rational Approach in Drug Design," Chem. Rev., 96: 3147-3176 (1996), esp. p. 3152.

Notification of Transmittal of the International Preliminary Examination Report for International Application No. PCT/US 02/21716, mailed Sep. 19, 2003.

Notification of Transmittal of the International Search Report or the Declaration for International Application No. PCT/US 02/21716, mailed Nov. 15, 2002.

Notification of Transmittal of the Written Opinion of the International Searching Authority for International Application No. PCT/US 02/21716, mailed Feb. 20, 2003.

Plumier, J.-C. L., et al., "Transgenic Mice Expressing the Human Heat Shock Protein 70 Have I proved Post-Ischemic Myocardial Recovery," *J Clin Invest*, 95: 1854-1860 (1995).

Cancer, Wikipedia, http://en.wikipedia.org/wiki/Cancer (1 of 40) Aug. 2, 2008 (all pages).

Radford, N.B., et al., "Cardioprotective Effects of 70-kDa Heat Shock Proteiin in Transgenic Mice," *Proc Natl Acad Sci USA*, 93(6): 2339-2342 (1996).

Rao et al., Cancer, vol. 106, No. 2: 375-382 (2006).

Renshaw, G.M.C., et al., "Oxygen Sensors and Energy Sensors Act Synergistically to Achieve a Graded Alteration in Gene Expression: Consequences for Assessing the Level of Neuroprotection in Response to Stressors," *Front Biosci*, 9: 110-116 (2004).

Carmel, J.B., et al., "Mediators of Ischemic Preconditioning Identified by Microarray Analysis of Rat Spinal Cord," *Exp. Neurol.*, 185: 81-96 (2004).

Sanchez, et al., "New naphthylcombretastatins. Modifications on the ethylene bridge," Bioorganic and Medicinal Chemistry, vol. 13, No. 6, Mar. 2005, pp. 2097-2107, XP002470852, ISSN: 0968-0896.

Sato, K., et al., "HSP70 is Essential to the Neuroprotective Effect of Heat-Shock," *Brain Res*, 740(1-2): 117-123 (1996).

Carter, R. J., et al., "Characterization of Progressive Motor Deficits in Mice Transgenic for the Human Huntington's Disease Mutation," *J. Neuroscience*, 19(8): 3248-3257 (1999).

Sauer, H. and Oertel, W.H., "Progressive Degeneration of Nigrostriatal Dopamine Neurons Following Instrastriatal Terminal Lesions with 6-Hydroxydopamine: A Combined Retrograde Tracing and Immunocytochemical Study in the Rat," *Neuroscience*, 59(2): 401-415 (1994).

Sausville et al., "Contributions to Human Tumor Xenografts to Anticancer Drug Development," *Cancer Research*, 2006, vol. 66, pp. 3351-3354.

Savage, E., et al., Living with Melanoma, [online], [retrieved on Aug. 9, 2006]. Retrieved from the Internet URL: http://ericandfran.com/melanona.htm.

Schroeter, G., et al., "Über methionsäure und deren verwendung zu synthesen," Instit der KgI. Tierärztlichen Hochschule Berlin, Oct. 26, 1918.

Chen, H-C., et al., Induction of Heat Shock Protein 70 Protects Mesangial Cells Against Oxidative Injury, *Kidney Int.*, 56: 1270-1273 (1999).

Shin, K.D., et al., "Blocking tumor cell migration and invasion with biphenyl isoxazole derivative KRIBB3, a synthetic molecule that inhibits Hsp27 phosphorylation" Journal of Biological Chemistry, American Society of Biolochemical Biologists, Birmingham, US, vol. 280 No. 50, Oct. 18, 2005, pp. 41439-41448, XP002391924, ISSN: 0021-9258.

Simon, M.M., et al., "Heat Shock Protein 70 Overexpression Affects the Response to Ultraviolet Light in Murine Fibroblasts," *J Clin Res*, 95(3): 926-933 (1995).

Sobue, G., Molecular Pathogenesis of Motor Neuron Diseases (In Japanese) English abstract, *Nihon Shinkei Seishin Yakurigaku Zasshi*, 21(1): 21-25 (2001).

Stalteri, M.A., et al., "Site-specific conjugation and labelling of prostate antibody 7E11C5.3 (CYT-351) with technetium-99m," *European Journal of Nuclear Medicine* 24(6):651-654, (1997).

Sun, et al., Shengwu Huaxue Yu Shengwu Wuli Xuebao, 4(5), 539-550 (1964).

Tanaka, S., et al., "Activation of T cells recognizing an epitope of heat-shock protein 70 can protect against rat adjuvant arthritis," Journal of Immunology, Nov. 1999, 163(10), 5560-5565.

Tavaria, M. et al., "A Hitchhiker's Guide to the Human Hsp70 Family," *Cell Stress Chaperones*, 1(1): 23-28 (1996).

Todryk, S.M., et al. "Facets of Heat Shock Protein 70 Show Immunotherapeutic Potential,", *Immunology*, 110(1): 1-9 (2003).

Tsuchiya, D., et al., "Overexpression of Rat Heat Shock Protein 70 Reduces Neuronal injury After Transient Focal Ischemia, Transient Global Ischemia, or Kainic Acid-Induced Seizures," *Neurosurgery*, 53(5): 1179-1187 (2003).

Berge, et al., "Pharmaceutical Salts," J. Pharm. Sci., 66 (1): 1-19, 1977.

Twomey, D., "Anticancer Agents-IX. Derivatives of Pyridine, Pyridazine and Phthalazine," *Proceedings of the Royal Irish Academy*, vol. 74, Sect. B:37-52,(1974).

Biagi, G. et al.,"1,5-Diarylsubstituted 1,2,3-triazoles as Potassium Channel Activators. VI," *Il Farmaco*, 59(5): 397-404 (2004), esp. p. 398.

Vippagunta, et al., "Crystalline solids," Advanced Drug Delivery Reviews, 48: 3-26, 2001.

Vleminckx, V., et al., "Upregulation of HSP27 in a Transgenic Model of ALS," *J Neuropathol Exp Neurol*, 61(11): 968-974 (2002).

Voss, R.M., et al., "Gender Differences in the Expression of Heat Shock Proteins: The Effect of Estrogen," *Am J Physiol Heart Circ Physiol*, 285: H687-H692 (2003).

Blondeau, N., et al., "Polyunsaturated Fatty Acids Induce Ischemic and Epileptic Tolerance," *Neuroscience*, 109(2): 231-241 (2002).

Wust, P. et al., "Hyperthermia in Combined Treatment of Cancer," *The Lancet Oncology*, 3(8): 487-497 (Aug. 2002), XP004813895.

Yenari, M.A., "Heat Shock Proteins and Neuroprotection," *Adv Exp Med Biol*, 513: 281-299 (2002).

Yu, Q., et al., "Retinal Uptake of Intravitreally Injected Hsc/Hsp70 and its Effect on Susceptibility to Light Damage," *Molecular Vision*, 7: 48-56 (2001).

Zhang, Y., et al., "Estrogen and Androgen Protection of Human Neurons Against Intracellular Amyloid $\beta_{1-42}$ Toxicity Through Heat Shock Protein 70," *J Neuroscience*, 24(23): 5315-5321 (2004).

Zinner, G., et al., "Über 2-Adamantylhydrazin und einige seiner Vorstufen und Derivate," *Arch. Pharm.* (Weinheim), 317: 1024-1028 (1984).

Gawande, N.G. et al., "Synthesis of Some Thiosemicarbazides and Related Compounds," CAPLUS, 1989, XP002391517.

Wiernik, P.H., et al., "Taxol in Malignant Melanoma," *J. Natl. Cancer Inst. Monogr.*, 15: 185-187 (1993) (abstract only).

* cited by examiner

COMBINATION WITH BIS(THIOHYDRAZIDE AMIDES) FOR TREATING CANCER

RELATED APPLICATIONS

This application claims the benefit of U.S. Provisional Application No. 60/841,570, filed Aug. 31, 2006, the entire teachings of which are incorporated herein by reference.

BACKGROUND OF THE INVENTION

Cancer is a group of diseases that are characterized by uncontrolled cell division. This uncontrolled division can compromise the function of an organism and ultimately may cause its death.

On average, in the United States, men have a 1 in 2 lifetime risk of developing cancer and women, a 1 in 3 risk. The International Agency for Research on Cancer estimated that there were 5.3 million new cases of cancer and 3.5 million cancer deaths worldwide in 2000. In the United States, more than 1.2 million new cases were diagnosed in 2002 and more than 550,000 people died of the disease. In fact, cancer is the second leading cause of death in the United States, exceeded only by heart disease.

Many cancers are immunosensitive. Immunosensitive cancers respond to immunotherapy, i.e., agents that stimulate the immune system. Examples of immunosensitive cancers include, renal cell carcinoma, melanoma, multiple myeloma, myeloma, lymphoma, non-small-cell lung cancer, bladder cancer, prostate cancer, squamous cell carcinoma, basal cell carcinoma, fibrosarcoma, malignant brain tumors, Kaposi's Sarcoma, chronic myelogenous leukemia (CML) and hairy cell leukemia.

Heat shock proteins (HSPs) are found in virtually all prokaryotic and eukaryotic cells where they support folding of nascent polypeptides, prevent protein aggregation, and assist transport of other proteins across membranes. The proteins in the Hsp70 family (referred to collectively as "Hsp70") play a dual role of protecting cells from lethal damage after environmental stress, on the one hand, and targeting cells for immune mediated cytolytic attack on the other hand. Increased expression of Hsp70 in the cytoplasma is known to protect a broad range of cells under stress by preventing the misfolding, aggregation and denaturation of cytoplasmic proteins and inhibiting various apoptotic pathways (Mosser, et al., Mol Cell Biol. 2000 October; 20(19): 7146-7159; Yenari, Adv Exp Med Biol, 2002, 513, 281-299; Kiang and Tsokos, Pharmacol Ther. 1998; 80(2):182-201). However, membrane-bound Hsp70 provides a target structure for cytolytic attack mediated by natural killer cells.

Cells can experience stress due to temperature; injury (trauma); genetic disease; metabolic defects; apoptosis; infection; toxins; radiation; oxidants; excess/lack of nutrients or metabolic products; and the like. For example, it is known in the art that cells damaged in the following variety of medical conditions can experience a protective effect in response to Hsp70.

Protein misfolding/aggregation conditions resulting in neurodegeneration include Alzheimers' disease (Zhang, et al., J. Neuroscience, 2004, 24(23), 5315-5321; Klettner, Drug News Perspect, 2004 17(5), 299-306); Huntington's disease (Klettner, ibid); Parkinson's disease (Auluck, et al., Science, 2002, 295(5556), 865-868); and the like. Other neurodegenerative conditions include spinal/bulbar muscular atrophy (Sobue, Nihon Shinkei Seishin Yakurigaku Zasshi, 2001, 21(1), 21-25); and familial amyotrophic lateral sclerosis (Howland, et al., Proc Nat Acad Sci USA, 2002, 99(3), 1604-1609; Sobue, ibid; Vleminck, et al., J Neuropathol Exp Neurol, 2002, 61(11), 968-974).

Ischemia and associated oxidative damage affects diverse tissues including: neurons and glia (Carmel, et al., Exp Neurol, 2004, 185(1) 81-96; Renshaw and Warburton, Front Biosci, 2004, 9, 110-116; Yenari, Adv Exp Med Biol, 2002, 513, 281-299; Kelly and Yenari, Curr Res Med Opin, 2002, 18 Suppl 2, s55-60; Lee, et al., Exp Neurol, 2001, 170(1), 129-139; Klettner, ibid; Klettner and Herdegen, Br J Pharmacol, 2003, 138(5), 1004-1012); cardiac muscle (Marber, M. S., et al. (1995) J. Clin. Invest. 95:1446-1456; Plumier, J. C., et al. (1995) J. Clin. Invest. 95:1854-1860; Radford, N. B., et al. (1996) Proc. Natl. Acad. Sci. USA 93(6): 2339-2342; Voss, et al., Am J Physiol Heart Circ Physiol 285: H687-H692, 2003); liver tissue (Doi, et al., Hepatogastroenterology. 2001 March-April; 48(38):533-40; Gao, et al. World J Gastroenterol 2004; 10(7):1019-1027); skeletal muscle (Lepore et al., Cell Stress & Chaperones, 2001, 6(2), 93-96); kidney tissue (Chen, et al., Kidney Int. 1999; 56: 1270-1273; Beck, et al., Am J Physiol Renal Physiol 279: F203-F215, 2000); pulmonary tissue (Hiratsuka, et al., J Heart Lung Transplant. 1998 December; 17(12):1238-46); pancreatic tissue (Bellmann, et al., J Clin Invest. 1995 June; 95(6): 2840-2845), and the like.

Seizure conditions that damage neurons include, e.g., epileptic seizure (Yenari, ibid; Blondeau, et al. Neuroscience 2002, 109(2), 231-241); or chemically induced seizure (Tsuchiya, et al., Neurosurgery, 2003, 53(5), 1179-1187).

Thermal stresses include hyperthermia conditions such as fever, heat stroke, and the like (Barclay and Robertson, J Neurobiol, 2003 56(4), 360-271; Sato, et al., Brain Res, 1996, 740(1-2), 117-123); and hypothermia (Kandor and Goldberg, Proc Natl Acad Sci USA. 1997 May 13; 94(10): 4978-4981).

Aging includes conditions such as atherosclerosis which affects smooth muscle cells (Minowada, G. and Welch, W. J. (1995) J. Clin. Invest. 95:3-12; Johnson, A. J., et al. (1995) Arterio. Thromb. Vasc. Biol. 15(1):27-36).

Other conditions include radiation damage, e.g., from ultraviolet light to tissues such as murine fibroblasts (Simon, M. M., et al. (1995) J. Clin. Res. 95(3): 926-933), and light damage to retinal cells (Yu, et, al, Molecular Vision 2001; 7:48-56).

Trauma includes, for example, mechanical injury, e.g., pressure damage to retinal ganglions in glaucoma (Ishii, et al., Invest Opthalmol Vis Sci, 2003, 44(5), 1982-1992).

Toxic conditions include doses of chemicals or biochemicals, for example, methamphetamine (Malberg & Seiden, Poster "MDMA Administration Induces Expression of HSP70 in the Rat Brain" Society for Neuroscience Annual Meeting, New Orleans, La., Oct. 25-30, 1997); antiretroviral HIV therapeutics (Keswani, et al., Annals Neurology, 2002, 53(1), 57-64); heavy metals, amino acid analogs, chemical oxidants, ethanol, glutamate, and other toxins (Ashburner, M. and Bonner, J. J. (1979) Cell: 17:241-254; Lindquist, S. (1986) Ann. Rev. Biochem. 55:1151-1191; Craig, E. A. (1985) Crit. Rev. Biochem. 18(3):239-280; Morimoto, et al., In: The Biology of Heat Shock Proteins and Molecular Chaperone, (1994) pp. 417-455. Cold Spring Harbor Laboratory Press. Cold Spring Harbor, N.Y.); and the like.

Therefore, there is a need for new methods of increasing expression of Hsp70 in order to treat disorders responsive to Hsp70.

Extracellular Hsp70 and membrane bound Hsp70 have been shown to play key roles in activation of the innate immune system. Monocytes have been shown to secrete proinflammatory cytokines in response to soluble Hsp70 protein and membrane bound Hsp70 has been shown to provide a target structure for cytolytic attack by natural killer cell.

Natural killer (NK) cells, a type of white blood cell, are known to be an important component of the body's immune system. Because the defining function of NK cells is spontaneous cytotoxicity without prior immunization, NK cells can be the first line of defense in the immune system, and are believed to play a role in attacking cancer cells and infectious diseases. Many conditions, such as immunodeficiency diseases, aging, toxin exposure, endometriosis, and the like can leave subjects with lowered NK cell activity or dysfunctional NK cells.

For example, subjects can have decreased or deficient NK cell activity, in conditions such as chronic fatigue syndrome (chronic fatigue immune dysfunction syndrome) or Epstein-Barr virus, post viral fatigue syndrome, post-transplantation syndrome or host-graft disease, exposure to drugs such as anticancer agents or nitric oxide synthase inhibitors, natural aging, and various immunodeficiency conditions such as severe combined immunodeficiency, variable immunodeficiency syndrome, and the like. (Caligiuri M, Murray C, Buchwald D, Levine H, Cheney P, Peterson D, Komaroff A L, Ritz J. Phenotypic and functional deficiency of natural killer cells in patients with chronic fatigue syndrome. Journal of Immunology 1987; 139: 3306-13; Morrison L J A, Behan W H M, Behan P O. Changes in natural killer cell phenotype in patients with post-viral fatigue syndrome. Clinical and Experimental Immunology 1991; 83: 441-6; Klingemann, H G Relevance and Potential of Natural Killer Cells in Stem Cell Transplantation Biology of Blood and Marrow Transplantation 2000; 6:90-99; Ruggeri L, Capanni M, Mancusi A, Aversa F, Martelli M F, Velardi A. Natural killer cells as a therapeutic tool in mismatched transplantation. Best Pract Res Clin Haematol. 2004 September; 17(3):427-38; Cifone M G, Ulisse S, Santoni A. Natural killer cells and nitric oxide. Int Immunopharmacol. 2001 August; 1(8):1513-24; Plackett T P, Boehmer E D, Faunce D E, Kovacs E J. Aging and innate immune cells. J Leukoc Biol. 2004 August; 76(2):291-9. Epub 2004 March 23; Alpdogan O, van den Brink M R. IL-7 and IL-15: therapeutic cytokines for immunodeficiency. Trends Immunol. 2005 January; 26(1):56-64; Heusel J W, Ballas Z K. Natural killer cells: emerging concepts in immunity to infection and implications for assessment of immunodeficiency. Curr Opin Pediatr. 2003 December; 15(6):586-93; Hacein-Bey-Abina S, Fischer A, Cavazzana-Calvo M. Gene therapy of X-linked severe combined immunodeficiency. Int J Hematol. 2002 November; 76(4):295-8; Baumert E, Schlesier M, Wolff-Vorbeck G, Peter H H. Alterations in lymphocyte subsets in variable immunodeficiency syndrome Immun Infekt. 1992 July; 20(3):73-5.)

NK cells are known to have activity against a wide range of infectious pathogens such as bacteria, viruses, fungi, protozoan parasites, combined infections, e.g., combined bacterial/viral infections, and the like. NK cells are believed to be particularly important in combating intracellular infections where the pathogens replicate in the subjects cells, e.g., a substantial fraction of viruses and many other pathogens that can form intracellular infections.

For example, a wide range of fungal infections are reported to be targeted by NK cells such as *Cryptococcus neoformans*, dermatophytes, e.g., *Trichophyton rubrum, Candida albicans, Coccidioides immitis, Paracoccidioides brasiliensis*, or the like (Hidore M R, Mislan T W, Murphy J W. Responses of murine natural killer cells to binding of the fungal target *Cryptococcus neoformans* Infect Immun. 1991 April; 59(4): 1489-99; Akiba H, Motoki Y, Satoh M, Iwatsuki K, Kaneko F; Recalcitrant trichophytic granuloma associated with NK-cell deficiency in a SLE patient treated with corticosteroid. Eur J. Dermatol. 2001 January-February; 11(1):58-62; Mathews H L, Witek-Janusek L. Antifungal activity of interleukin-2-activated natural killer (NK1.1+) lymphocytes against *Candida albicans*. J Med. Microbiol. 1998 November; 47(11):1007-14; Ampel N M, Bejarano G C, Galgiani J N. Killing of *Coccidioides immitis* by human peripheral blood mononuclear cells. Infect Immun. 1992 October; 60(10):4200-4; Jimenez B E, Murphy J W. In vitro effects of natural killer cells against Paracoccidioides brasiliensis yeast phase. Infect Immun. 1984 November; 46(2):552-8.)

Also targeted by NK cells are bacteria, especially intracellular bacteria, e.g., *Mycobacterium tuberculosis, Mycobacterium avium, Listeria monocytogenes*, many different viruses, such as human immunodeficiency virus, herpesviruses, hepatitis, and the like, and viral/bacterial co-infection (Esin S, Batoni G, Kallenius G, Gaines H, Campa M, Svenson S B, Andersson R, Wigzell H. Proliferation of distinct human T cell subsets in response to live, killed or soluble extracts of *Mycobacterium tuberculosis* and *Myco. avium*. Clin Exp Immunol. 1996 June; 104(3):419-25; Kaufmann S H. Immunity to intracellular bacteria. Annu Rev Immunol. 1993; 11:129-63; See D M, Khemka P, Sahl L, Bui T, Tilles J G. The role of natural killer cells in viral infections. Scand J. Immunol. 1997 September; 46(3):217-24; Brenner B G, Dascal A, Margolese R G, Wainberg M A. Natural killer cell function in patients with acquired immunodeficiency syndrome and related diseases. J Leukoc Biol. 1989 July; 46(1):75-83; Kottilil S, Natural killer cells in HIV-1 infection: role of NK cell-mediated non-cytolytic mechanisms in pathogenesis of HIV-1 infection. Indian J Exp Biol. 2003 November; 41(11): 1219-25; Herman R B, Koziel M J. Natural killer cells and hepatitis C: is losing inhibition the key to clearance? Clin Gastroenterol Hepatol. 2004 December; 2(12):1061-3; Beadling C, Slifka M K. How do viral infections predispose patients to bacterial infections? Curr Opin Infect Dis. 2004 June; 17(3): 185-91).

In addition, NK cells combat protozoal infections including toxoplasmosis, trypanosomiasis, leishmaniasis and malaria, especially intracellular infections (Korbel D S, Finney O C, Riley E M. Natural killer cells and innate immunity to protozoan pathogens. Int J Parasitol. 2004 December; 34(13-14):1517-28; Ahmed J S, Mehlhorn H. Review: the cellular basis of the immunity to and immunopathogenesis of tropical theileriosis. Parasitol Res. 1999 July; 85(7):539-49; Osman M, Lausten S B, El-Sefi T, Boghdadi I, Rashed M Y, Jensen S L. Biliary parasites. Dig Surg. 1998; 15(4):287-96; Gazzinelli R T, Denkers E Y, Sher A. Host resistance to *Toxoplasma gondii*: model for studying the selective induction of cell-mediated immunity by intracellular parasites. Infect Agents Dis. 1993 June; 2(3): 139-49; Askonas B A, Bancroft G J. Interaction of African trypanosomes with the immune system. Philos Trans R Soc Lond B Biol Sci. 1984 Nov. 13; 307(1131):41-9; Allison A C, Eugui E M. The role of cell-mediated immune responses in resistance to malaria, with special reference to oxidant stress. Annu Rev Immunol. 1983; 1:361-92.)

NK cells have been shown to play a role in attacking cancer cells that present membrane bound Hsp70. It is believed that membrane bound Hsp70 binds to CD94 receptors on the surface of NK cells and cause them to produce and secrete high amounts of the enzyme, granzyme B which is thought to enter the tumor cell via interaction with membrane bound Hsp70 and induce apoptosis (see Radons and Multhoff, Exerc. Immunol. Rev. (2005), 11:17-33). Therefore, there is an urgent need for effective treatments for increasing NK cell activity for the treatment of cancer and other disorders that respond to NK induction.

Radiation therapy and chemotherapy are commonly used treatments for cancer. However, it is well known that these therapies often result in incomplete killing of the cancer cells and that reoccurrence of the cancer can result in cancer that is more resistant to radiation or chemotherapy.

Many chemotherapeutic drugs cause cells to generate reactive oxygen species (ROS) which can lead to cellular signaling that induces either apoptosis or proliferation. ROS are generated during normal metabolism in the mitochondria of cells. However, the buffering action of endogenous thiols, such as glutathione and thioredoxin, protect cells from oxidative damage and help maintain the reduction-oxidation (redox) state of the cell. If ROS are elevated to a level which exceeds the buffering capacity of the cell, activation of signaling pathways and gene expression that induce apoptosis can occur. Cancer cells are generally more susceptible to ROS induced apoptosis than normal cells because the environment created by uncontrolled growth of a tumor is typically hypoxic. However, radiation therapy and chemotherapy that results in incomplete killing of cancer cells can result in the remaining cancer cells developing a resistance to oxidative stress. For example, cancer cells can compensate for the generation of ROS by upregulating the amount of glutathione (GSH) or components of the thioredoxin system, such as thioredoxin reductase. GSH is a cellular antioxidant that contains a reducing thiol group which donates electrons to ROS, thereby neutralize them. The thioredoxin system includes thioredoxin, a protein that has a redox-active disulfide group which can be reduced by thioredoxin reductase to two dithiol groups in the presence of NADPH. The dithiol form of thioredoxin is a powerful protein-disulfide reductase which helps regulate the redox state of the cell. Cellular resistance to anticancer drugs such as paclitaxel has been shown to be proportional to the total antioxidant capacity of a target cell.

By upregulating cellular defense mechanisms against ROS, cancer cells can evade destruction by radiation and chemotherapeutic drugs. Therefore, a need exists for agents that reduce cellular mechanism of compensating for ROS and induce cellular signaling pathways that lead to apoptosis. Such agents would be expected to increase the effectiveness of existing anti-cancer agents.

SUMMARY OF THE INVENTION

Certain compounds of the invention induce Hsp70 production in cells and thereby increase the level of Hsp70 in the cytoplasm and on the surface of cells. In addition, certain compounds of the invention are cytotoxic to cancer cell lines, including multi-drug resistant cancer cell lines, and enhance the anti-proliferative and apoptotic activity (e.g., anti-cancer activity) of Taxol and taxane analogs.

It has now been found that bis(thiohydrazide amides) in combination with taxol significantly increase the time to disease progression in patients with Stage IV melanoma. As noted above melanoma is an immunosensitive cancer. The use of bis(thiohydrazide amides) in combination with other anticancer therapies to treat a proliferative disorder, such as cancer, is disclosed herein. In one embodiment, the method is used to treat melanoma and other immunosensitive cancers.

Moreover it has also been found that bis(thiohydrazide amides) concentrate in the kidneys. In one particular embodiment, the method of treating renal cell carcinoma, another immunosensitive cancer, is also disclosed herein.

The present invention is directed to methods of treating a subject with a proliferative disorder, such as cancer, comprising administering to the subject an effective amount of a bis(thiohydrazide amide) in combination with hyperthermia treatment, optionally comprising one or more additional anticancer therapies.

The present invention is also directed to methods of treating a subject with a proliferative disorder, such as cancer, comprising administering to the subject an effective amount of a bis(thiohydrazide amide) in combination with radiotherapy, optionally comprising one or more additional anticancer therapies.

The methods include administering to the subject an effective amount of a bis(thio-hydrazide amide) represented by Structural Formula I:

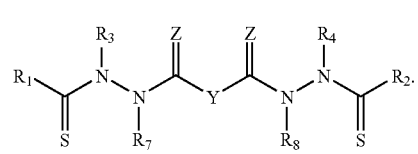

or a tautomer, pharmaceutically acceptable salt, solvate, clathrate, or prodrug thereof, wherein Y is a covalent bond or an optionally substituted straight chained hydrocarbyl group, or, Y, taken together with both >C=Z groups to which it is bonded, is an optionally substituted aromatic group.

$R_1$-$R_4$ are independently —H, an optionally substituted aliphatic group, an optionally substituted aryl group, or $R_1$ and $R_3$ taken together with the carbon and nitrogen atoms to which they are bonded, and/or $R_2$ and $R_4$ taken together with the carbon and nitrogen atoms to which they are bonded, form a non-aromatic ring optionally fused to an aromatic ring.

$R_7$-$R_8$ are independently —H, an optionally substituted aliphatic group, or an optionally substituted aryl group.

Z is O or S;

in combination with hyperthermia treatment or radiotherapy.

Also disclosed are methods of treating a subject with a cancer selected from the group consisting of:

i) human sarcoma or carcinoma, selected from the group consisting of fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, colorectal cancer, anal carcinoma, esophageal cancer, gastric cancer, hepatocellular cancer, bladder cancer, endometrial cancer, pancreatic cancer, breast cancer, ovarian cancer, prostate cancer, stomach cancer, atrial myxomas, squamous cell carcinoma, basal cell carcinoma, adenocarcinoma, sweat gland carcinoma, sebaceous gland carcinoma, thyroid and parathyroid neoplasms, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, non-small-cell lung cancer, bladder carcinoma, epithelial carcinoma, glioma, pituitary neoplasms, astrocytoma, medulloblastoma, craniopharyngioma, ependymoma, pinealoma, hemangioblastoma, acoustic neuroma, schwannomas, oligodendroglioma, meningioma, spinal cord tumors, melanoma, neuroblastoma, pheochromocytoma, Types 1-3 endocrine neoplasia, retinoblastoma; and ii) leukemia, selected from the group consisting of acute lymphocytic leukemia, acute myelocytic leukemia; chronic leukemia, polycythemia vera, lymphoma, multiple myeloma, Waldenstrobm's macroglobulinemia, heavy chain disease, T-cell leukemias, B cell leukemia; mixed cell leukemias, myeloid leukemias, neutrophilic leukemia, eosinophilic leukemia, monocytic leukemia, myelomonocytic leukemia, Naegeli-type myeloid leukemia, and nonlymphocytic leukemia;

comprising administering to the subject an effective amount of a compound represented by Structural Formula I and in combination with hyperthermia treatment or radiotherapy.

DETAILED DESCRIPTION OF THE INVENTION

Figure 1:
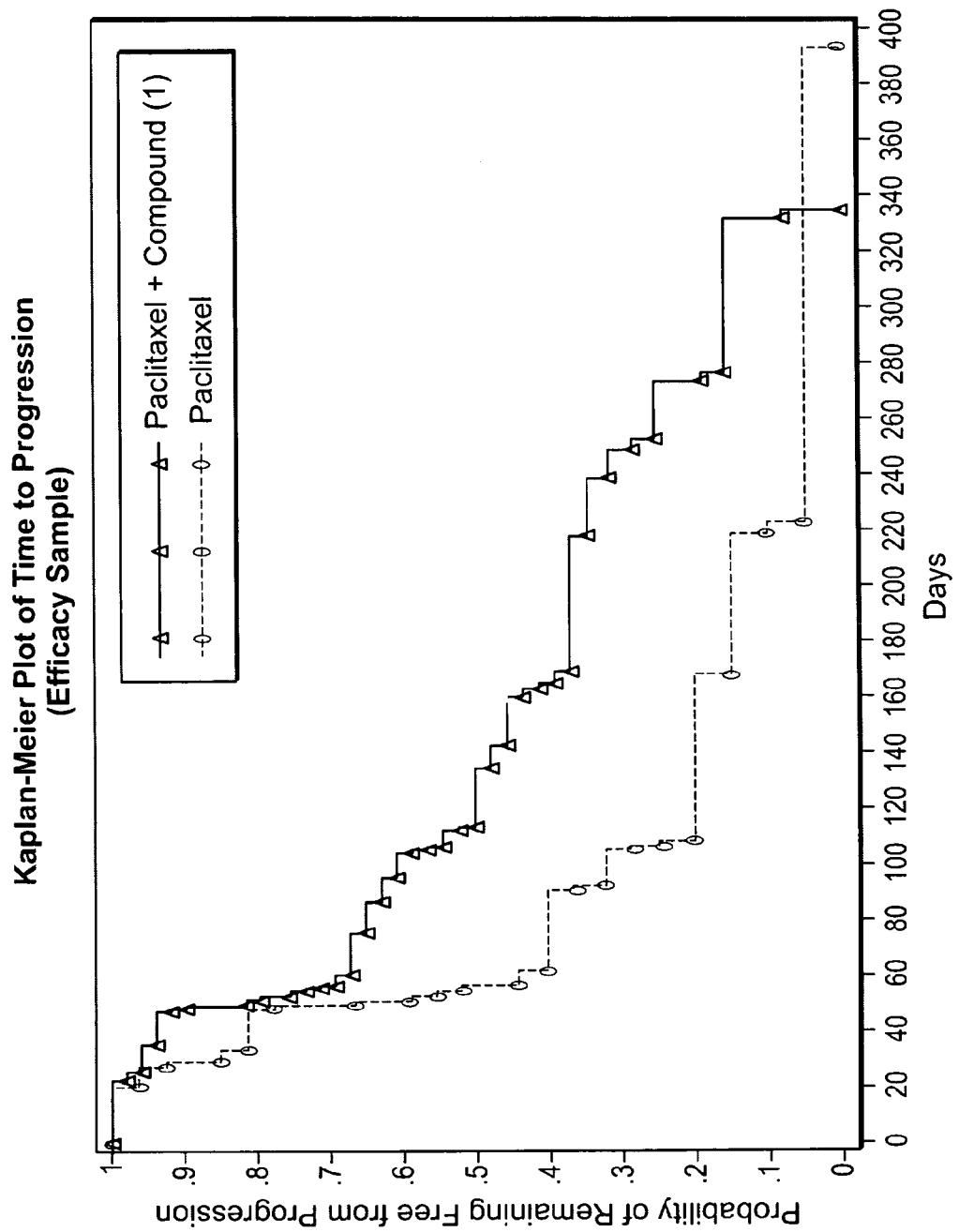
FIG. 1 is a Kaplan-Meier graph of time-to-progression (resumption of cancer growth) in a study of Paclitaxel+compound (I) versus Paclitaxel alone.

The present invention relates to methods of treating a subject with a proliferative disorder, such as cancer, comprising administering to the subject an effective amount of a bis(thio-hydrazide amide) represented by a formula selected from Structural Formulas (I)-(IX) (or a compound encompassed by these structural formulas) or a tautomer, pharmaceutically acceptable salt, solvate, clathrate, or prodrug thereof, in combination with another anti-proliferative or anticancer therapy.

The present invention also relates to methods of treating a subject with a proliferative disorder, such as cancer, comprising administering to the subject an effective amount of a bis(thio-hydrazide amide) represented by a formula selected from Structural Formulas (I)-(IX) (or a compound encompassed by these structural formulas) or a tautomer, pharmaceutically acceptable salt, solvate, clathrate, or prodrug thereof, in combination with hyperthermia treatment.

The present invention also relates to methods of treating a subject with a proliferative disorder, such as cancer, comprising administering to the subject an effective amount of a bis(thio-hydrazide amide) represented by a formula selected from Structural Formulas (I)-(IX) (or a compound encompassed by these structural formulas) or a tautomer, pharmaceutically acceptable salt, solvate, clathrate, or prodrug thereof, in combination with radiotherapy.

The present invention is also directed to methods of treating an immunosensitive cancer with an effective amount of a bis(thio-hydrazide amide) represented by a formula selected from Structural Formulas (I)-(IX) (or a compound encompassed by these structural formulas) or a tautomer, pharmaceutically acceptable salt, solvate, clathrate, or prodrug thereof, in combination with hyperthermia treatment. In particular, melanoma and renal cell carcinoma are two immunosensitive treated using the disclosed methods.

The present invention is also directed to methods of treating an immunosensitive cancer with an effective amount of a bis(thio-hydrazide amide) represented by a formula selected from Structural Formulas (I)-(IX) (or a compound encompassed by these structural formulas) or a tautomer, pharmaceutically acceptable salt, solvate, clathrate, or prodrug thereof, in combination with radiotherapy. In particular, melanoma and renal cell carcinoma are two immunosensitive cancers treated using the disclosed methods.

The present invention is also directed to methods of preventing or delaying the recurrence of an immunosensitive cancer in a subject who has been treated for the cancer. The methods include administering to the subject an effective amount of a bis(thio-hydrazide amide) represented by Structural Formula I or a tautomer, pharmaceutically acceptable salt, solvate, clathrate, or prodrug thereof, in combination with another anti-proliferative or anticancer therapy.

The bis(thio-hydrazide amides) employed in the disclosed invention are represented by Structural Formula I and pharmaceutically acceptable salts and solvates of the compounds represented by Structural Formula I.

In one embodiment, Y in Structural Formula I is a covalent bond, —C($R_5R_6$)—, —($CH_2CH_2$)—, trans-(CH=CH)—, cis-(CH=CH)— or —(C≡C)— group, preferably —C($R_5R_6$)—. $R_1$-$R_4$ are as described above for Structural Formula I. $R_5$ and $R_6$ are each independently —H, an aliphatic or substituted aliphatic group, or $R_5$ is —H and $R_6$ is an optionally substituted aryl group, or, $R_5$ and $R_6$, taken together, are an optionally substituted C2-C6 alkylene group. In one embodiment, the compound of Structural Formula I is in the form of a pharmaceutically acceptable salt. In one embodiment, the compound of Structural Formula I is in the form of a pharmaceutically acceptable salt in combination with one or more pharmaceutically acceptable cations. The pharmaceutically acceptable cations are as described in detail below.

In specific embodiments, Y taken together with both >C=Z groups to which it is bonded, is an optionally substituted aromatic group. In this instance, certain bis(thio-hydrazide amides) are represented by Structural Formula II:

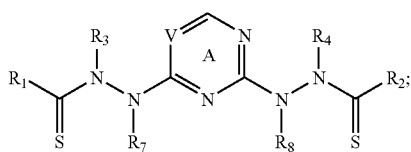

or a tautomer, pharmaceutically acceptable salt, solvate, clathrate, or prodrug thereof, wherein Ring A is substituted or unsubstituted and V is —CH— or —N—. The other variables in Structural Formula II are as described herein for Structural Formula I or IIIa.

In particular embodiments, the bis(thio-hydrazide amides) are represented by Structural Formula IIIa:

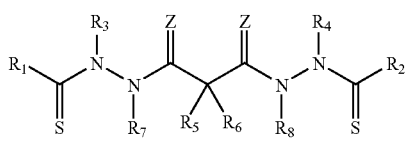

or a tautomer, pharmaceutically acceptable salt; solvate, clathrate, or prodrug thereof, wherein $R_1$-$R_8$ are as described above for Structural Formula I.

In Structural Formulas I-IIIa, $R_1$ and $R_2$ are the same or different and/or $R_3$ and $R_4$ are the same or different; preferably, $R_1$ and $R_2$ are the same and $R_3$ and $R_4$ are the same. In Structural Formulas I and IIIa, Z is preferably O. Typically in Structural Formulas I and IIIa, Z is O; $R_1$ and $R_2$ are the same; and $R_3$ and $R_4$ are the same. More preferably, Z is O; $R_1$ and $R_2$ are the same; $R_3$ and $R_4$ are the same, and $R_7$ and $R_8$ are the same.

In other embodiments, the bis(thio-hydrazide amides) are represented by Structural Formula IIIa: $R_1$ and $R_2$ are each an optionally substituted aryl group, preferably an optionally substituted phenyl group; $R_3$ and $R_4$ are each an optionally substituted aliphatic group, preferably an alkyl group optionally substituted with —OH, halogen, phenyl, benzyl, pyridyl, or C1-C8 alkoxy and $R_6$ is —H or methyl, more preferably, methyl or ethyl group optionally substituted with —OH, halogen, phenyl, benzyl, pyridyl, or C1-C8 alkoxy and $R_6$ is —H or methyl optionally substituted with —OH, halogen or C1-C4 alkoxy; and $R_5$ and $R_6$ are as described above, but $R_5$ is preferably —H and $R_6$ is preferably —H, an aliphatic or substituted aliphatic group.

Alternatively, $R_1$ and $R_2$ are each an optionally substituted aryl group; $R_3$ and $R_4$ are each an optionally substituted aliphatic group; $R_5$ is —H; and $R_6$ is —H, an aliphatic or substituted aliphatic group. Preferably, $R_1$ and $R_2$ are each an optionally substituted aryl group; $R_3$ and $R_4$ are each an alkyl group optionally substituted with —OH, halogen, phenyl, benzyl, pyridyl, or C1-C8 alkoxy and $R_6$ is —H or methyl; and $R_5$ is —H and $R_6$ is —H or methyl. Even more preferably, $R_1$ and $R_2$ are each an optionally substituted phenyl group, preferably optionally substituted with —OH, halogen, C1-4 alkyl or C1-C4 alkoxy; $R_3$ and $R_4$ are each methyl or ethyl optionally substituted with —OH, halogen or C1-C4 alkoxy; and $R_5$ is —H and $R_6$ is —H or methyl. Suitable substituents for an aryl group represented by $R_1$ and $R_2$ and an aliphatic group represented by $R_3$, $R_4$ and $R_6$ are as described below for aryl and aliphatic groups.

In another embodiment, the bis(thio-hydrazide amides) are represented by Structural Formula IIa: $R_1$ and $R_2$ are each an optionally substituted aliphatic group, preferably a C3-C8 cycloalkyl group optionally substituted with at least one alkyl group, more preferably cyclopropyl or 1-methylcyclopropyl; $R_3$ and $R_4$ are as described above for Structural Formula I, preferably both an optionally substituted alkyl group; and $R_5$ and $R_6$ are as described above, but $R_5$ is preferably —H and $R_6$ is preferably —H, an aliphatic or substituted aliphatic group, more preferably —H or methyl.

Alternatively, the bis(thio-hydrazide amides) are represented by Structural Formula IIIa: $R_1$ and $R_2$ are each an optionally substituted aliphatic group; $R_3$ and $R_4$ are as described above for Structural Formula I, preferably both an optionally substituted alkyl group; and $R_5$ is —H and $R_6$ is —H or an optionally substituted aliphatic group. Preferably, $R_1$ and $R_2$ are both a C3-C8 cycloalkyl group optionally substituted with at least one alkyl group; $R_3$ and $R_4$ are both as described above for Structural Formula I, preferably an alkyl group; and $R_5$ is —H and $R_6$ is —H or an aliphatic or substituted aliphatic group. More preferably, $R_1$ and $R_2$ are both a C3-C8 cycloalkyl group optionally substituted with at least one alkyl group; $R_3$ and $R_4$ are both an alkyl group optionally substituted with —OH, halogen, phenyl, benzyl, pyridyl, or C1-C8 alkoxy and $R_6$ is —H or methyl; and $R_5$ is —H and $R_6$ is —H or methyl. Even more preferably, $R_1$ and $R_2$ are both cyclopropyl or 1-methylcyclopropyl; $R_3$ and $R_4$ are both an alkyl group, preferably methyl or ethyl optionally substituted with —OH, halogen or C1-C4 alkoxy; and $R_5$ is —H and $R_6$ is —H or methyl.

In particular embodiments, the bis(thio-hydrazide amides) are represented by Structural Formula IIIb:

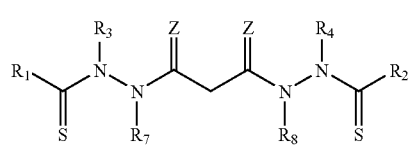

or a tautomer, pharmaceutically acceptable salt, solvate, clathrate, or prodrug thereof, wherein $R_1$, $R_2$, $R_3$, $R_4$, $R_7$, $R_8$, and Z are as defined above for Structural Formula IIIa.

In specific embodiments, the bis(thio-hydrazide amides) are represented by Structural Formula IVa:

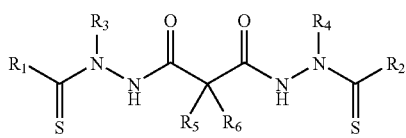

or a tautomer, pharmaceutically acceptable salt, solvate, clathrate, or prodrug thereof, wherein: $R_1$ and $R_2$ are both phenyl, $R_3$ and $R_4$ are both methyl, and $R_5$ and $R_6$ are both —H; $R_1$ and $R_2$ are both phenyl, $R_3$ and $R_4$ are both ethyl, and $R_5$ and $R_6$ are both —H; $R_1$ and $R_2$ are both 4-cyanophenyl, $R_3$ and $R_4$ are both methyl, $R_5$ is methyl, and $R_6$ is —H; $R_1$ and $R_2$ are both 4-methoxyphenyl, $R_3$ and $R_4$ are both methyl, and $R_5$ and $R_6$ are both —H; $R_1$ and $R_2$ are both phenyl, $R_3$ and $R_4$ are both methyl, $R_5$ is methyl, and $R_6$ is —H; $R_1$ and $R_2$ are both phenyl, $R_3$ and $R_4$ are both ethyl, $R_5$ is methyl, and $R_6$ is —H; $R_1$ and $R_2$ are both 4-cyanophenyl, $R_3$ and $R_4$ are both methyl, and $R_5$ and $R_6$ are both —H; $R_1$ and $R_2$ are both 2,5-dimethoxyphenyl, $R_3$ and $R_4$ are both methyl, and $R_5$ and $R_6$ are both —H; $R_1$ and $R_2$ are both 2,5-dimethoxyphenyl, $R_3$ and $R_4$ are both methyl, $R_5$ is methyl, and $R_6$ is —H; $R_1$ and $R_2$ are both 3-cyanophenyl, $R_3$ and $R_4$ are both methyl, and $R_5$ and $R_6$ are both —H; $R_1$ and $R_2$ are both 3-fluorophenyl, $R_3$ and $R_4$ are both methyl, and $R_5$ and $R_6$ are both —H; $R_1$ and $R_2$ are both 4-chlorophenyl, $R_3$ and $R_4$ are both methyl, $R_5$ is methyl, and $R_6$ is —H; $R_1$ and $R_2$ are both 2-dimethoxyphenyl, $R_3$ and $R_4$ are both methyl, and $R_5$ and $R_6$ are both —H; $R_1$ and $R_2$ are both 3-methoxyphenyl, $R_3$ and $R_4$ are both methyl, and $R_5$ and $R_6$ are both —H; $R_1$ and $R_2$ are both 2,3-dimethoxyphenyl, $R_3$ and $R_4$ are both methyl, and $R_5$ and $R_6$ are both —H; $R_1$ and $R_2$ are both 2,3-dimethoxyphenyl, $R_3$ and $R_4$ are both methyl, $R_5$ is methyl, and $R_6$ is —H; $R_1$ and $R_2$ are both 2,5-difluorophenyl, $R_3$ and $R_4$ are both methyl, and $R_5$ and $R_6$ are both —H; $R_1$ and $R_2$ are both 2,5-difluorophenyl, $R_3$ and $R_4$ are both methyl, $R_5$ is methyl, and $R_6$ is —H; $R_1$ and $R_2$ are both 2,5-dichlorophenyl, $R_3$ and $R_4$ are both methyl, and $R_5$ and $R_6$ are both —H; $R_1$ and $R_2$ are both 2,5-dimethylphenyl, $R_3$ and $R_4$ are both methyl, and $R_5$ and $R_6$ are both —H; $R_1$ and $R_2$ are both 2,5-dimethoxyphenyl, $R_3$ and $R_4$ are both methyl, and $R_5$ and $R_6$ are both —H; $R_1$ and $R_2$ are both phenyl, $R_3$ and $R_4$ are both methyl, and $R_5$ and $R_6$ are both —H; $R_1$ and $R_2$ are both 2,5-dimethoxyphenyl, $R_3$ and $R_4$ are both methyl, $R_5$ is methyl, and $R_6$ is —H; $R_1$ and $R_2$ are both cyclopropyl, $R_3$ and $R_4$ are both methyl, and $R_5$ and $R_6$ are both —H; $R_1$ and $R_2$ are both cyclopropyl, $R_3$ and $R_4$ are both ethyl, and $R_5$ and $R_6$ are both —H; $R_1$ and $R_2$ are both cyclopropyl, $R_3$ and $R_4$ are both methyl, $R_5$ is methyl, and $R_6$ is —H; $R_1$ and $R_2$ are both 1-methylcyclopropyl, $R_3$ and $R_4$ are both methyl, and $R_5$ and $R_6$ are both —H; $R_1$ and $R_2$ are both 1-methylcyclopropyl, $R_3$ and $R_4$ are both methyl, $R_5$ is methyl and $R_6$ is —H; $R_1$ and $R_2$ are both 1-methylcyclopropyl, $R_3$ and $R_4$ are both methyl, $R_5$ is ethyl, and $R_6$ is —H; $R_1$ and $R_2$ are both 1-methylcyclopropyl, $R_3$ and $R_4$ are both methyl, $R_5$ is n-propyl, and $R_6$ is —H; $R_1$ and $R_2$ are both 1-methylcyclopropyl, $R_3$ and $R_4$ are both methyl, and $R_5$ and $R_6$ are both methyl; $R_1$ and $R_2$ are both 1-methylcyclopropyl, $R_3$ and $R_4$ are both ethyl, and $R_5$ and $R_6$ are both —H; $R_1$ and $R_2$ are both 1-methylcyclopropyl, $R_3$ is methyl, $R_4$ is ethyl, and $R_5$ and $R_6$ are both —H; $R_1$ and $R_2$ are both 2-methylcyclopropyl, $R_3$ and $R_4$ are both methyl, and $R_5$ and $R_6$ are both —H; $R_1$ and $R_2$ are both 2-phenylcyclopropyl, $R_3$ and $R_4$ are both methyl, and $R_5$ and $R_6$ are both —H; $R_1$ and $R_2$ are both 1-phenylcyclopropyl, $R_3$ and $R_4$ are both methyl, and $R_5$ and $R_6$ are both —H; $R_1$ and $R_2$ are both cyclobutyl, $R_3$ and $R_4$ are both methyl, and $R_5$ and $R_6$ are both —H; $R_1$ and $R_2$ are both cyclopentyl, $R_3$ and $R_4$ are both methyl, and $R_5$ and $R_6$ are both —H; $R_1$ and $R_2$ are both cyclohexyl, $R_3$ and $R_4$ are both methyl, and $R_5$ and $R_6$ are both —H; $R_1$ and $R_2$ are both cyclohexyl, $R_3$ and $R_4$ are both phenyl, and $R_5$ and $R_6$ are both —H; $R_1$ and $R_2$ are both methyl, $R_3$ and $R_4$ are both methyl, and $R_5$ and $R_6$ are both —H; $R_1$ and $R_2$ are both methyl, $R_3$ and $R_4$ are both t-butyl, and $R_5$ and $R_6$ are both —H; $R_1$ and $R_2$ are both methyl, $R_3$ and $R_4$ are both phenyl, and $R_5$ and $R_6$ are both —H; $R_1$ and $R_2$ are both t-butyl, $R_3$ and $R_4$ are both methyl, and $R_5$ and $R_6$ are both —H; $R_1$ and $R_2$ are ethyl, $R_3$ and $R_4$ are both methyl, and $R_5$ and $R_6$ are both —H; or $R_1$ and $R_2$ are both n-propyl, $R_3$ and $R_4$ are both methyl, and $R_5$ and $R_6$ are both —H.

In particular embodiments, the bis(thio-hydrazide amides) are represented by Structural Formula IVb:

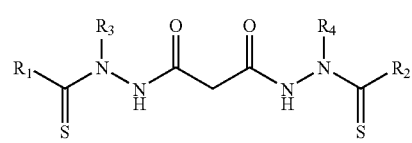

or a tautomer, pharmaceutically acceptable salt, solvate, clathrate, or prodrug thereof, wherein $R_1$, $R_2$, $R_3$, and $R_4$ are as defined above for Structural Formula IVa.

In specific embodiments, the bis(thio-hydrazide amides) are represented by Structural Formula V:

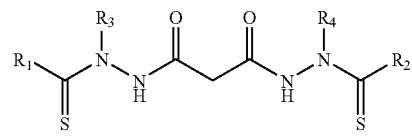

or a tautomer, pharmaceutically acceptable salt, solvate, clathrate, or prodrug thereof, wherein: $R_1$ and $R_2$ are both phenyl, and $R_3$ and $R_4$ are both o-$CH_3$-phenyl; $R_1$ and $R_2$ are both o-$CH_3$C(O)O-phenyl, and $R_3$ and $R_4$ are phenyl; $R_1$ and $R_2$ are both phenyl, and $R_3$ and $R_4$ are both methyl; $R_1$ and $R_2$ are both phenyl, and $R_3$ and $R_4$ are both ethyl; $R_1$ and $R_2$ are both phenyl, and $R_3$ and $R_4$ are both n-propyl; $R_1$ and $R_2$ are both p-cyanophenyl, and $R_3$ and $R_4$ are both methyl; $R_1$ and $R_2$ are both p-nitro phenyl, and $R_3$ and $R_4$ are both methyl; $R_1$ and $R_2$ are both 2,5-dimethoxyphenyl, and $R_3$ and $R_4$ are both methyl; $R_1$ and $R_2$ are both phenyl, and $R_3$ and $R_4$ are both n-butyl; $R_1$ and $R_2$ are both p-chlorophenyl, and $R_3$ and $R_4$ are both methyl; $R_1$ and $R_2$ are both 3-nitrophenyl, and $R_3$ and $R_4$ are both methyl; $R_1$ and $R_2$ are both 3-cyanophenyl, and $R_3$ and $R_4$ are both methyl; $R_1$ and $R_2$ are both 3-fluorophenyl, and $R_3$ and $R_4$ are both methyl; $R_1$ and $R_2$ are both 2-furanyl, and $R_3$ and $R_4$ are both phenyl; $R_1$ and $R_2$ are both 2-methoxyphenyl, and $R_3$ and $R_4$ are both methyl; $R_1$ and $R_2$ are both 3-methoxyphenyl, and $R_3$ and $R_4$ are both methyl; $R_1$ and $R_2$ are both 2,3-dimethoxyphenyl, and $R_3$ and $R_4$ are both methyl; $R_1$ and $R_2$ are both 2-methoxy-5-chlorophenyl, and $R_3$ and $R_4$ are both ethyl; $R_1$ and $R_2$ are both 2,5-difluorophenyl, and $R_3$ and $R_4$ are both methyl; $R_1$ and $R_2$ are both 2,5-dichlorophenyl, and $R_3$ and $R_4$ are both methyl; $R_1$ and $R_2$ are both 2,5-dimethylphenyl, and $R_3$ and $R_4$ are both methyl; $R_1$ and $R_2$ are both 2-methoxy-5-chlorophenyl, and $R_3$ and $R_4$ are both methyl; $R_1$ and $R_2$ are both 3,6-dimethoxyphenyl, and $R_3$ and $R_4$ are both methyl; $R_1$ and $R_2$ are both phenyl, and $R_3$ and $R_4$ are both 2-ethylphenyl; $R_1$ and $R_2$ are both 2-methyl-5-pyridyl, and $R_3$ and $R_4$ are both methyl; or $R_1$ is phenyl;

$R_2$ is 2,5-dimethoxyphenyl, and $R_3$ and $R_4$ are both methyl; $R_1$ and $R_2$ are both methyl, and $R_3$ and $R_4$ are both p-$CF_3$-phenyl; $R_1$ and $R_2$ are both methyl, and $R_3$ and $R_4$ are both o-$CH_3$-phenyl; $R_1$ and $R_2$ are both —$(CH_2)_3COOH$; and $R_3$ and $R_4$ are both phenyl; $R_1$ and $R_2$ are both represented by the following structural formula:

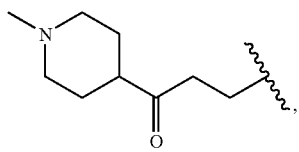

and $R_3$ and $R_4$ are both phenyl; $R_1$ and $R_2$ are both n-butyl, and $R_3$ and $R_4$ are both phenyl; $R_1$ and $R_2$ are both n-pentyl, $R_3$ and $R_4$ are both phenyl; $R_1$ and $R_2$ are both methyl, and $R_3$ and $R_4$ are both 2-pyridyl; $R_1$ and $R_2$ are both cyclohexyl, and $R_3$ and $R_4$ are both phenyl; $R_1$ and $R_2$ are both methyl, and $R_3$ and $R_4$ are both 2-ethylphenyl; $R_1$ and $R_2$ are both methyl, and $R_3$ and $R_4$ are both 2,6-dichlorophenyl; $R_1$-$R_4$ are all methyl; $R_1$ and $R_2$ are both methyl, and $R_3$ and $R_4$ are both t-butyl; $R_1$ and $R_2$ are both ethyl, and $R_3$ and $R_4$ are both methyl; $R_1$ and $R_2$ are both t-butyl, and $R_3$ and $R_4$ are both methyl; $R_1$ and $R_2$ are both cyclopropyl, and $R_3$ and $R_4$ are both methyl; $R_1$ and $R_2$ are both cyclopropyl, and $R_3$ and $R_4$ are both ethyl; $R_1$ and $R_2$ are both 1-methylcyclopropyl, and $R_3$ and $R_4$ are both methyl; $R_1$ and $R_2$ are both 2-methylcyclopropyl, and $R_3$ and $R_4$ are both methyl; $R_1$ and $R_2$ are both 1-phenylcyclopropyl, and $R_3$ and $R_4$ are both methyl; $R_1$ and $R_2$ are both 2-phenylcyclopropyl, and $R_3$ and $R_4$ are both methyl; $R_1$ and $R_2$ are both cyclobutyl, and $R_3$ and $R_4$ are both methyl; $R_1$ and $R_2$ are both cyclopentyl, and $R_3$ and $R_4$ are both methyl; $R_1$ is cyclopropyl, $R_2$ is phenyl, and $R_3$ and $R_4$ are both methyl.

Preferred examples of bis(thio-hydrazide amides) include Compounds (1)-(18) and pharmaceutically acceptable salts and solvates thereof:

Compound (1)
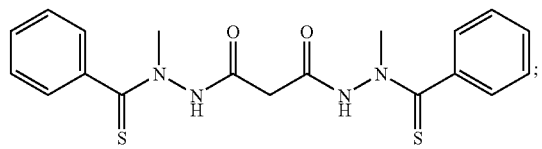

Compound (2)
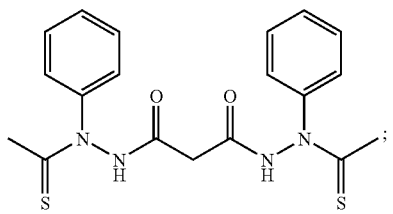

Compound (3)
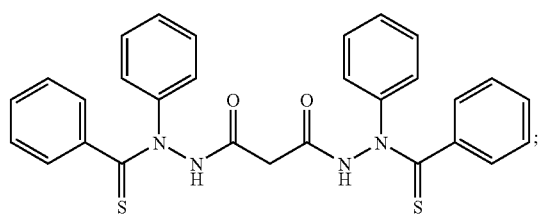

Compound (4)
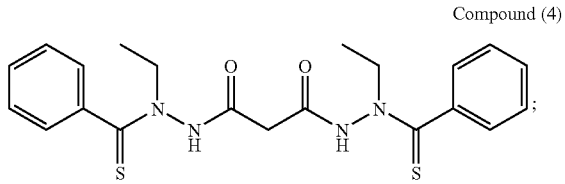

Compound (5)
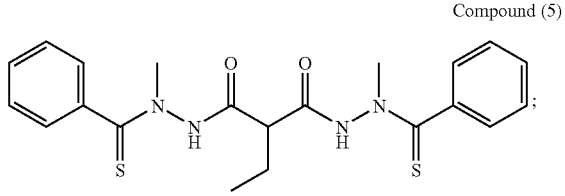

Compound (6)
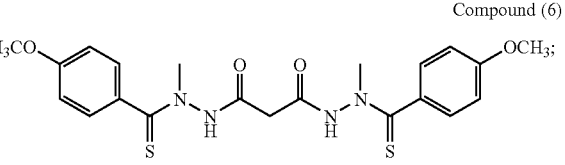

Compound (7)
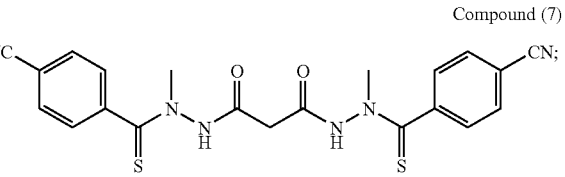

Compound (8)
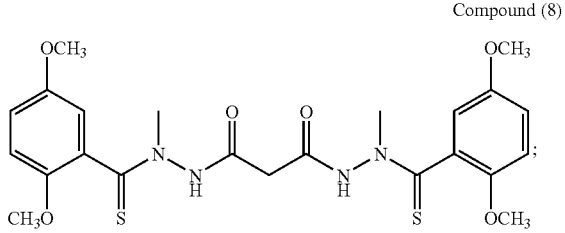

Compound (9)
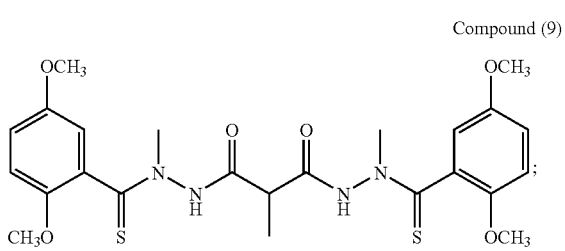

Compound (10)
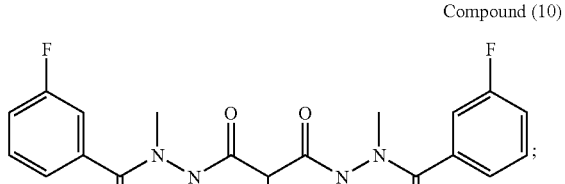

Compound (11)
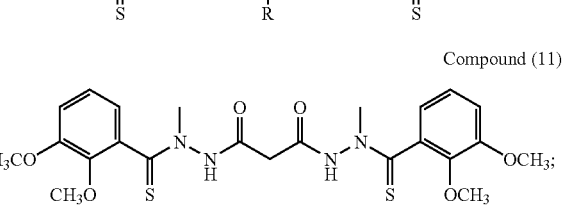

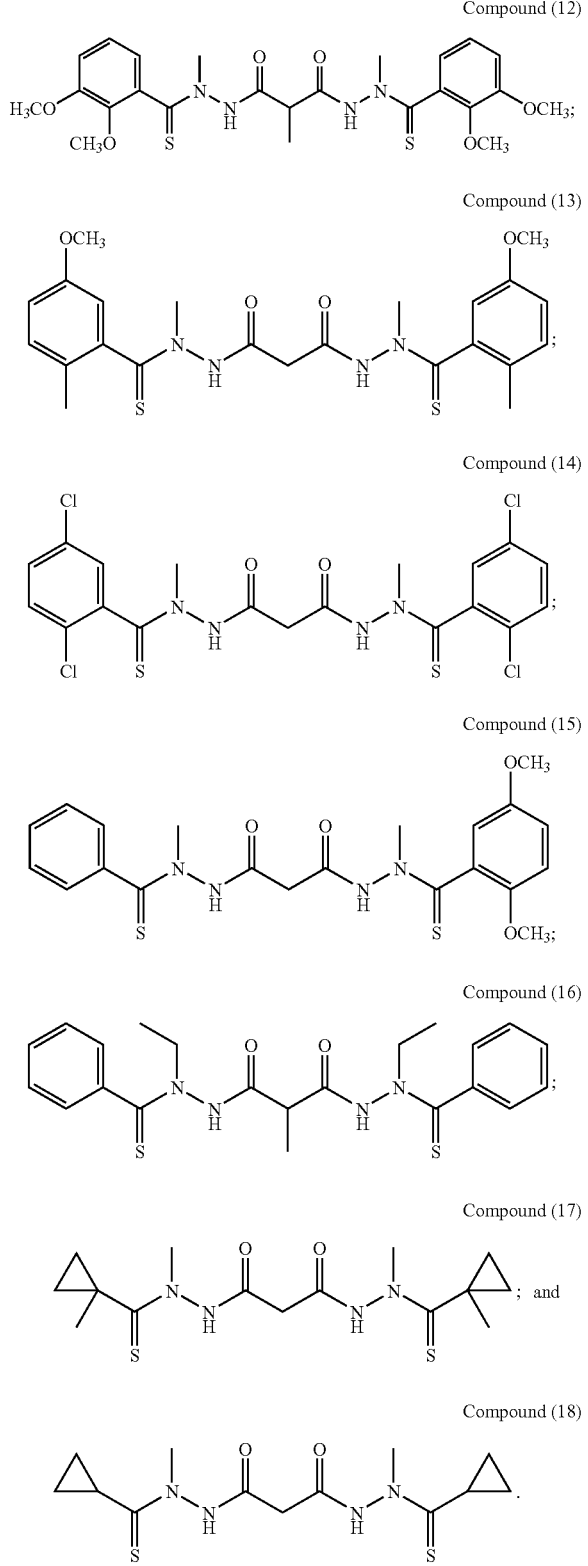

Compound (12)
Compound (13)
Compound (14)
Compound (15)
Compound (16)
Compound (17)
Compound (18)

As used herein, the term "bis(thio-hydrazide amide)" and references to the Structural Formulas of this invention also include pharmaceutically acceptable salts and solvates of these compounds and Structural Formulas. Examples of acceptable salts and solvates are described in US Publication No.: 20060135595 and U.S. patent application Ser. No. 11/432,307 filed 11 May 2006, titled Synthesis Of Bis(Thio-Hydrazide Amide) Salts, the entire contents of each of which are incorporated herein by reference.

These compounds can have one or more sufficiently acidic proton that can react with a suitable organic or inorganic base to form a base addition salt. Base addition salts include those derived from inorganic bases, such as ammonium or alkali or alkaline earth metal hydroxides, carbonates, bicarbonates, and the like, and organic bases such as alkoxides, alkyl amides, alkyl and aryl amines, and the like. Such bases useful in preparing the salts of this invention thus include sodium hydroxide, potassium hydroxide, ammonium hydroxide, potassium carbonate, and the like.

For example, pharmaceutically acceptable salts of bis(thio-hydrazide) amides employed herein (e.g., those represented by Structural Formulas I-VI, Compounds 1-18) are those formed by the reaction of the compound with one equivalent of a suitable base to form a monovalent salt (i.e., the compound has single negative charge that is balanced by a pharmaceutically acceptable counter cation, e.g., a monovalent cation) or with two equivalents of a suitable base to form a divalent salt (e.g., the compound has a two-electron negative charge that is balanced by two pharmaceutically acceptable counter cations, e.g., two pharmaceutically acceptable monovalent cations or a single pharmaceutically acceptable divalent cation). Divalent salts of the bis(thio-hydrazide amides) are preferred. "Pharmaceutically acceptable" means that the cation is suitable for administration to a subject. Examples include $Li^+$, $Na^+$, $K^+$, $Mg^{2+}$, $Ca^{2+}$ and $NR_4^+$, wherein each R is independently hydrogen, an optionally substituted aliphatic group (e.g., a hydroxyalkyl group, aminoalkyl group or ammoniumalkyl group) or optionally substituted aryl group, or two R groups, taken together, form an optionally substituted non-aromatic heterocyclic ring optionally fused to an aromatic ring. Generally, the pharmaceutically acceptable cation is $Li^+$, $Na^+$, $K^+$, $NH_3(C_2H_5OH)^+$ or $N(CH_3)_3(C_2H_5OH)^+$, and more typically, the salt is a disodium or dipotassium salt, preferably the disodium salt.

Bis(thio-hydrazide) amides employed herein having a sufficiently basic group, such as an amine can react with an organic or inorganic acid to form an acid addition salt. Acids commonly employed to form acid addition salts from compounds with basic groups are inorganic acids such as hydrochloric acid, hydrobromic acid, hydroiodic acid, sulfuric acid, phosphoric acid, and the like, and organic acids such as p-toluenesulfonic acid, methanesulfonic acid, oxalic acid, p-bromophenyl-sulfonic acid, carbonic acid, succinic acid, citric acid, benzoic acid, acetic acid, and the like. Examples of such salts include the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, gamma-hydroxybutyrate, glycolate, tartrate, methanesulfonate, propanesulfonate, naphthalene-1-sulfonate, naphthalene-2-sulfonate, mandelate, and the like.

Salts of the disclosed bis(thiohydrazide amides) may have tautomeric forms. By way of example, one tautomeric form for the disalt is:

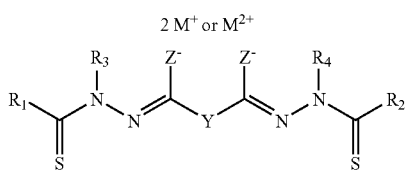

(VI)

Y is a covalent bond or a substituted or unsubstituted straight chained hydrocarbyl group. $R_1$-$R_4$ are independently —H, an aliphatic group, a substituted aliphatic group, an aryl group or a substituted aryl group, or $R_1$ and $R_3$ taken together with the carbon and nitrogen atoms to which they are bonded, and/or $R_2$ and $R_4$ taken together with the carbon and nitrogen atoms to which they are bonded, form a non-aromatic heterocyclic ring optionally fused to an aromatic ring. Z is —O or —S. $M^+$ is a pharmaceutically acceptable monovalent cation and $M^{2+}$ is a pharmaceutically acceptable divalent cation.

In one embodiment, the variables for Structural Formula (VI) are defined below:

$M^+$ is a pharmaceutically acceptable monovalent cation. $M^{2+}$ is a pharmaceutically acceptable divalent cation. "Pharmaceutically acceptable" means that the cation is suitable for administration to a subject. Examples of $M^+$ or $M^{2+}$ include $Li^+$, $Na^+$, $K^+$, $Mg^{2+}$, $Ca^{2+}$, $Zn^{2+}$, and $NR_4^+$, wherein each R is independently hydrogen, a substituted or unsubstituted aliphatic group (e.g., a hydroxyalkyl group, aminoalkyl group or ammoniumalkyl group) or substituted or unsubstituted aryl group, or two R groups, taken together, form a substituted or unsubstituted non-aromatic heterocyclic ring optionally fused to an aromatic ring. Preferably, the pharmaceutically acceptable cation is $Li^+$, $Na^+$, $K^+$, $NH_3(C_2H_5OH)^+$, $N(CH_3)_3(C_2H_5OH)^+$, arginine or lysine. More preferably, the pharmaceutically acceptable cation is $Na^+$ or $K^+$. $Na^+$ is even more preferred.

Exemplary tautomeric forms of the disalt compounds represented by Structural Formula (VI) wherein Y is —$CH_2$— are shown below:

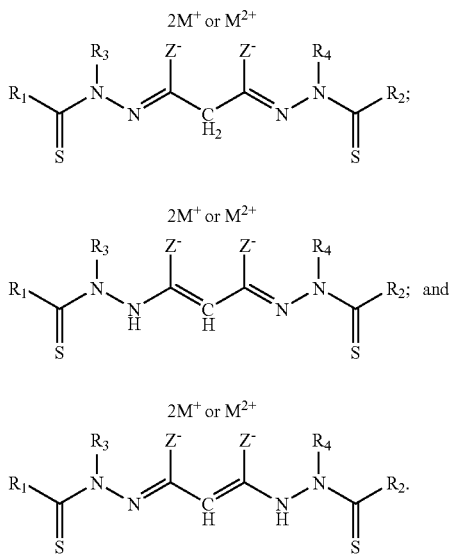

Representative tautomeric structures of the disalt of Compound (1) are shown below:

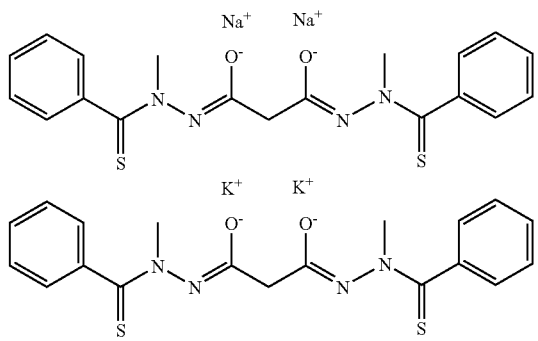

Preferred examples of bis(thio-hydrazide amide) disalts of the present invention are the following:

(VI)

(VIII)

(IX)

$2M^+$ and $M^{2+}$ are as described above for Structural Formula (VI). Preferably, the pharmaceutically acceptable cation is $2 M^+$, wherein $M^+$ is $Li^+$, $Na^+$, $K^+$, $NH_3(C_2H_5OH)^+$ or $N(CH_3)_3(C_2H_5OH)^+$. More preferably, $M^+$ is $Na^+$ or $K^+$. Even more preferably, $M^+$ is $Na^+$.

It is to be understood when one tautomeric form of a disclosed compound is depicted structurally, other tautomeric forms are also encompassed.

Certain compounds of the invention may be obtained as different stereoisomers (e.g., diastereomers and enantiomers). The invention includes all isomeric forms and racemic mixtures of the disclosed compounds and methods of treating a subject with both pure isomers and mixtures thereof, including racemic mixtures. Stereoisomers can be separated and isolated using any suitable method, such as chromatography.

As used herein, the term "clathrate" means a compound of the present invention or a salt thereof in the form of a crystal lattice that contains spaces (e.g., channels) that have a guest molecule (e.g., a solvent or water) trapped within.

As used herein and unless otherwise indicated, the term "prodrug" means a derivative of a compound that can hydrolyze, oxidize, or otherwise react under biological conditions (in vitro or in vivo) to provide a compound of this invention. Prodrugs may become active upon such reaction under biological conditions, or they may have activity in their unreacted forms. Examples of prodrugs contemplated in this invention include, but are not limited to, analogs or derivatives of compounds of formula (I) through (XII) and Table 1 that comprise biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Other examples of prodrugs include derivatives of compounds of formula (I) through (XII) and Table 1, that comprise —NO, —NO$_2$, —ONO, or —ONO$_2$ moieties. Prodrugs can typically be prepared using well-known methods, such as those described by 1 BURGER'S MEDICINAL CHEMISTRY AND DRUG DISCOVERY (1995) 172-178, 949-982 (Manfred E. Wolff ed., 5$^{th}$ ed).

As used herein and unless otherwise indicated, the terms "biohydrolyzable amide", "biohydrolyzable ester", "biohydrolyzable carbamate", "biohydrolyzable carbonate", "biohydrolyzable ureide" and "biohydrolyzable phosphate analogue" mean an amide, ester, carbamate, carbonate, ureide, or phosphate analogue, respectively, that either: 1) does not destroy the biological activity of the compound and confers upon that compound advantageous properties in vivo, such as improved water solubility, improved circulating half-life in the blood (e.g., because of reduced metabolism of the prodrug), improved uptake, improved duration of action, or improved onset of action; or 2) is itself biologically inactive but is converted in vivo to a biologically active compound. Examples of biohydrolyzable amides include, but are not limited to, lower alkyl amides, α-amino acid amides, alkoxyacyl amides, and alkylaminoalkylcarbonyl amides. Examples of biohydrolyzable esters include, but are not limited to, lower alkyl esters, alkoxyacyloxy esters, alkyl acylamino alkyl esters, and choline esters. Examples of biohydrolyzable carbamates include, but are not limited to, lower alkylamines, substituted ethylenediamines, aminoacids, hydroxyalkylamines, heterocyclic and heteroaromatic amines, and polyether amines.

An "alkyl group" is saturated straight or branched chain linear or cyclic hydrocarbon group. Typically, a straight chained or branched alkyl group has from 1 to about 20 carbon atoms, preferably from 1 to about 10, and a cyclic alkyl group has from 3 to about 10 carbon atoms, preferably from 3 to about 8. An alkyl group is preferably a straight chained or branched alkyl group, e.g., methyl, ethyl, n-propyl, iso-propyl, n-butyl, sec-butyl, tert-butyl, pentyl, hexyl, pentyl or octyl, or a cycloalkyl group with 3 to about 8 carbon atoms. A C1-C8 straight chained or branched alkyl group or a C3-C8 cyclic alkyl group is also referred to as a "lower alkyl" group. Suitable substituents for an alkyl group are those which do not substantially interfere with the anti-cancer activity of the disclosed compounds. Suitable substituents are as described below for aliphatic groups. Preferred substituents on alkyl groups include, —OH, —NH$_2$, —NO$_2$, —CN, —COOH, halogen, aryl, C1-C8 alkoxy, C1-C8 haloalkoxy and —CO(C1-C8 alkyl). More preferred substituents on alkyl groups include —OH, halogen, phenyl, benzyl, pyridyl, and C1-C8 alkoxy. More preferred substituents on alkyl groups include —OH, halogen, and C1-C4 alkoxy.

A "straight chained hydrocarbyl group" is an alkylene group, i.e., —(CH$_2$)$_y$—, with one or more (preferably one) internal methylene groups optionally replaced with a linkage group. y is a positive integer (e.g., between 1 and 10), preferably between 1 and 6 and more preferably 1 or 2. A "linkage group" refers to a functional group which replaces a methylene in a straight chained hydrocarbyl. Examples of suitable linkage groups include a ketone (—C(O)—), alkene, alkyne, phenylene, ether (—O—), thioether (—S—), or amine (—N(R$^a$)—), wherein R$^a$ is defined below. A preferred linkage group is —C(R$_5$R$_6$)—, wherein R$_5$ and R$_6$ are defined above. Suitable substituents for an alkylene group and a hydrocarbyl group are those which do not substantially interfere with the anti-cancer activity of the disclosed compounds. R$_5$ and R$_6$ are preferred substituents for an alkylene or hydrocarbyl group represented by Y.

An aliphatic group is a straight chained, branched or cyclic non-aromatic hydrocarbon which is completely saturated or which contains one or more units of unsaturation. Typically, a straight chained or branched aliphatic group has from 1 to about 20 carbon atoms, preferably from 1 to about 10, and a cyclic aliphatic group has from 3 to about 10 carbon atoms, preferably from 3 to about 8. An aliphatic group is preferably a straight chained or branched alkyl group, e.g., methyl, ethyl, n-propyl, iso-propyl, n-butyl, sec-butyl, tert-butyl, pentyl, hexyl, pentyl or octyl, or a cycloalkyl group with 3 to about 8 carbon atoms. A C1-C8 straight chained or branched alkyl group or a C3-C8 cyclic alkyl group is also referred to as a "lower alkyl" group.

The term "aromatic group" may be used interchangeably with "aryl," "aryl ring," "aromatic ring," "aryl group" and "aromatic group." Aromatic groups include carbocyclic aromatic groups such as phenyl, naphthyl, and anthracyl, and heteroaryl groups such as imidazolyl, thienyl, furanyl, pyridyl, pyrimidy, pyranyl, pyrazolyl, pyrroyl, pyrazinyl, thiazole, oxazolyl, and tetrazole. The term "heteroaryl group" may be used interchangeably with "heteroaryl," "heteroaryl ring," "heteroaromatic ring" and "heteroaromatic group." Heteroaryl groups are aromatic groups that comprise one or more heteroatom, such as sulfur, oxygen and nitrogen, in the ring structure. Preferably, heteroaryl groups comprise from one to four heteroatoms.

Aromatic groups also include fused polycyclic aromatic ring systems in which a carbocyclic aromatic ring or heteroaryl ring is fused to one or more other heteroaryl rings. Examples include benzothienyl, benzofuranyl, indolyl, quinolinyl, benzothiazole, benzooxazole, benzimidazole, quinolinyl, isoquinolinyl and isoindolyl.

Non-aromatic heterocyclic rings are non-aromatic rings which include one or more heteroatoms such as nitrogen, oxygen or sulfur in the ring. The ring can be five, six, seven or eight-membered. Preferably, heterocyclic groups comprise from one to about four heteroatoms. Examples include tetrahydrofuranyl, tetrahydrothiophenyl, morpholino, thiomorpholino, pyrrolidinyl, piperazinyl, piperidinyl, and thiazolidinyl.

Suitable substituents on an aliphatic group (including an alkylene group), non-aromatic heterocyclic group, benzylic or aryl group (carbocyclic and heteroaryl) are those which do not substantially interfere with the anti-cancer activity of the disclosed compounds. A substituent substantially interferes with anti-cancer activity when the anti-cancer activity is reduced by more than about 50% in a compound with the substituent compared with a compound without the substituent. Examples of suitable substituents include —R$^a$, —OH, —Br, —Cl, —I, —F, —OR$^a$, —O—COR$^a$, —COR$^a$, —CN, —NO$_2$, —COOH, —SO$_3$H, —NH$_2$, —NHR$^a$, —N(R$^a$R$^b$), —COOR$^a$, —CHO, —CONH$_2$, —CONHR$^a$, —CON(R$^a$R$^b$), —NHCOR$^a$, —NR$^c$COR$^a$, —NHCONH$_2$, —NH-CONR$^a$H, —NHCON(R$^a$R$^b$), —NRCCONH$_2$, NRCCON- R$^a$H, —NRCCON(R$^a$R$^b$), —C(=NH)—NH$_2$, —C(=NH)—NHR$^a$, —C(=NH)—N(R$^a$R$^b$), —C(=NR$^c$)—NH$_2$, —C(=NR$^c$)—NHR$^a$, —C(=NR$^c$)—N(R$^a$R$^b$), —NH—C(=NH)—NH$_2$, —NH—C(=NH)—NHR$^a$, —NH—C(=NH)—N(R$^a$R$^b$), —NH—C(=NR$^c$)—NH$_2$, —NH—C(=NR$^c$)—NHR$^a$, —NH—C(=NR$^c$)—N(R$^a$R$^b$), —NR$^d$H—C(=NH)—NH$_2$, —NR$^d$—C(=NH)—NHR$^a$, —NR$^d$—C(=NH)—N(R$^a$R$^b$), —NR$^d$—C(=NR$^c$)—NH$_2$, —NR$^d$—C(=NR$^c$)—NHR$^a$, NR$^d$—C(=NR$^c$)—N(R$^a$R$^b$), —NHNH$_2$, —NHNHR$^a$, —NR$^a$R$^b$, —SO$_2$NH$_2$, —SO$_2$NHR$^a$, —SO$_2$NR$^a$R$^b$, —CH=CHR$^a$, —CH=CR$^a$R$^b$, —CR$^c$=CR$^a$R$^b$, —CR$^c$=CHR$^a$, —CR$^c$=CR$^a$R$^b$, —CCR$^a$, —SH, —SR$^a$, —S(O)R$^a$, —S(O)$_2$R$^a$.

R$^a$-R$^d$ are each independently an alkyl group, aromatic group, non-aromatic heterocyclic group or —N(R$^a$R$^b$), taken together, form a non-aromatic heterocyclic group. The alkyl, aromatic and non-aromatic heterocyclic group represented by R$^a$-R$^d$ and the non-aromatic heterocyclic group represented by —N(R$^a$R$^b$) are each optionally and independently substituted with one or more groups represented by R$^\#$. Preferably R$^a$-R$^d$ are unsubstituted.

R$^\#$ is R$^+$, —OR$^+$, —O(haloalkyl), —SR$^+$, —NO$_2$, —CN, —NCS, —N(R$^+$)$_2$, —NHCO$_2$R$^+$, —NHC(O)R$^+$, —NHNHC(O)R$^+$, —NHC(O)N(R$^+$)$_2$, —NHNHC(O)N(R$^+$)$_2$, —NHNHCO$_2$R$^+$, —C(O)C(O)R$^+$, —C(O)CH$_2$C(O)R$^+$, —CO$_2$R$^+$, —C(O)R$^+$, —C(O)N(R$^+$)$_2$, —OC(O)R$^+$, —OC(O)N(R$^+$)$_2$, —S(O)$_2$R$^+$, —SO$_2$N(R$^+$)$_2$, —S(O)R$^+$, —NHSO$_2$N(R$^+$)$_2$, —NHSO$_2$R$^+$, —C(=S)N(R$^+$)$_2$, or —C(=NH)—N(R$^+$)$_2$.

R$^+$ is —H, a C1-C4 alkyl group, a monocyclic heteroaryl group, a non-aromatic heterocyclic group or a phenyl group optionally substituted with alkyl, haloalkyl, alkoxy, haloalkoxy, halo, —CN, —NO$_2$, amine, alkylamine or dialkylamine. Preferably R$^+$ is unsubstituted. Optionally, the group —N(R$^+$)$_2$ is a non-aromatic heterocyclic group, provided that non-aromatic heterocyclic groups represented by R$^+$ and —N(R$^+$)$_2$ that comprise a secondary ring amine are optionally acylated or alkylated.

Preferred substituents for a phenyl group, including phenyl groups represented by R$_1$-R$_4$, include C$_1$-C$_4$ alkyl, C$_1$-C$_4$ alkoxy, C$_1$-C$_4$ haloalkyl, C1-C4 haloalkoxy, phenyl, benzyl, pyridyl, —OH, —NH$_2$, —F, —Cl, —Br, —I, —NO$_2$ or —CN. More preferred for a phenyl group, including phenyl groups represented by R$_1$-R$_4$, include R$_1$ and R$_2$ are optionally substituted with —OH, —CN, halogen, C1-4 alkyl or C1-C4 alkoxy Preferred substituents for a cycloalkyl group, including cycloalkyl groups represented by R$_1$ and R$_2$, are alkyl groups, such as a methyl or ethyl group.

Other anti-proliferative or anticancer therapies may be combined with the compounds of this invention to treat proliferative diseases and cancer. Other therapies or anticancer agents that may be used in combination with the inventive anticancer agents of the present invention include surgery, radiotherapy (including, but not limited to, gamma-radiation, neutron beam radiotherapy, electron beam radiotherapy, proton therapy, brachytherapy, and systemic radioactive isotopes), endocrine therapy, biologic response modifiers (including, but not limited to, interferons, interleukins, and tumor necrosis factor (TNF)), hyperthermia and cryotherapy, agents to attenuate any adverse effects (e.g., antiemetics), and other approved chemotherapeutic drugs.

The prophylactic or therapeutic agents of the combination therapies of the invention can be administered sequentially or concurrently.

As used herein, the terms "hyperthermia", "hyperthermia therapy," "thermal therapy," and "thermotherapy" are used interchangeably to mean a treatment where body tissue is exposed to high temperatures (up to 113° F.). The term as used herein includes all forms of hyperthermia, including local, regional, and whole-body. Various forms of energy can be used to deliver heat to the desired area, such as microwave, radiofrequency, lasers, and ultrasound. The treatment temperatures vary depending on the location of the tumor and the approach used.

In local hyperthermia, heat is applied to a small area (e.g. a tumor). The approaches to local hyperthermia vary with tumor location. External approaches are used to treat tumors in or just below the skin. In this method, applicators are place near or around the tumor and deliver energy directly to the tumor. Intraluminal or endocavitary approaches use probes to deliver energy to tumors within or near body cavities. Interstitial approaches are used to treat tumors deep within the body (e.g. brain tumors), by inserting probes or needles into the tumor under anesthesia.

In regional hyperthermia, heat is applied to large areas of tissue (e.g. body cavity, organ, or limb). Deep tissue approaches are used to treat cancers within the body (e.g. cervical or bladder cancer) by using external applicators. Regional perfusion approaches are used to treat cancers in the limbs or organs (e.g. melanoma, liver, or lung cancer). In this approach some of the blood is removed and heated and then pumped back into the limb or organ. Anticancer drugs may be given during this process. Continuous hyperthermic peritoneal perfusion (CHPP) is used to treat cancers in the peritoneal cavity (e.g. peritoneal mesothelioma or stomach cancer). In this approach, heated anticancer drugs are pumped through the peritoneal cavity.

Whole-body hyperthermia is used to treat metastatic cancer. In this approach, the whole body is heated to 107-108° F. by using various techniques such as thermal chambers or hot water blankets.

Hyperthermic conditions are known to induce the synthesis of Hsp70.

As used herein, "Hsp70" includes each member of the family of heat shock proteins having a mass of about 70-kiloDaltons, including forms such as constitutive, cognate, cell-specific, glucose-regulated, inducible, etc. Examples of specific Hsp70 proteins include hsp70, hsp70hom; hsc70; Grp78/BiP; mt-hsp70/Grp75, and the like). Typically, the disclosed methods increase expression of inducible Hsp70. Functionally, the 70-kDa HSP (HSP70) family is a group of chaperones that assist in the folding, transport, and assembly of proteins in the cytoplasm, mitochondria, and endoplasmic reticulum. Membrane-bound Hsp70 In humans, the Hsp70 family encompasses at least 11 genes encoding a group of highly related proteins. See, for example, Tavaria, et al., Cell Stress Chaperones, 1996; 1(1):23-28; Todryk, et al., Immunology. 2003, 110(1): 1-9; and Georgopoulos and Welch, Annu Rev Cell Biol. 1993; 9:601-634; the entire teachings of these documents are incorporated herein by reference.

Immunotherapy (also called biological response modifier therapy, biologic therapy, biotherapy, immune therapy, or biological therapy) is treatment that uses parts of the immune system to fight disease. Immunotherapy can help the immune system recognize cancer cells, or enhance a response against cancer cells. Immunotherapies include active and passive immunotherapies. Active immunotherapies stimulate the body's own immune system while passive immunotherapies generally use immune system components created outside of the body.

Examples of active immunotherapies include, but are not limited to vaccines including cancer vaccines, tumor cell vaccines (autologous or allogeneic), viral vaccines, dendritic cell vaccines, antigen vaccines, anti-idiotype vaccines, DNA vaccines, or Tumor-Infiltrating Lymphocyte (TIL) Vaccine with Interleukin-2 (IL-2) or Lymphokine-Activated Killer (LAK) Cell Therapy.

Examples of passive immunotherapies include but are not limited to monoclonal antibodies and targeted therapies containing toxins. Monoclonal antibodies include naked antibodies and conjugated antibodies (also called tagged, labeled, or loaded antibodies). Naked monoclonal antibodies do not have a drug or radioactive material attached whereas conjugated monoclonal antibodies are joined to, for example, a chemotherapy drug (chemolabeled), a radioactive particle (radiolabeled), or a toxin (immunotoxin).

In certain embodiments of the present invention passive immunotherapies, such as, naked monoclonal antibody drugs can be used in combination with the bis(thio hydrazide amides) described herein to treat cancer in the methods of the present invention. Examples of these naked monoclonal antibody drugs include, but are not limited to Rituximab (Rituxan), an antibody against the CD20 antigen used to treat, for example, B cell non-Hodgkin lymphoma; Trastuzumab (Herceptin), an antibody against the HER2 protein used to treat, for example, advanced breast cancer; Alemtuzumab (Campath), an antibody against the CD52 antigen used to treat, for example, B cell chronic lymphocytic leukemia (B-CLL); Cetuximab (Erbitux), an antibody against the EGFR protein used, for example, in combination with irinotecan to treat, for example, advanced colorectal cancer and head and neck cancers; and Bevacizumab (Avastin) which is an antiangiogenesis therapy that works against the VEGF protein and is used, for example, in combination with chemotherapy to treat, for example, metastatic colorectal cancer.

Further examples of therapeutic antibodies that can be used include, but are not limited to, HERCEPTIN® (Trastuzumab) (Genentech, CA) which is a humanized anti-HER2 monoclonal antibody for the treatment of patients with metastatic breast cancer; REOPRO® (abciximab) (Centocor) which is an anti-glycoprotein IIb/IIIa receptor on the platelets for the prevention of clot formation; ZENAPAX® (daclizumab) (Roche Pharmaceuticals, Switzerland) which is an immunosuppressive, humanized anti-CD25 monoclonal antibody for the prevention of acute renal allograft rejection; PANOREX™ which is a murine anti-17-IA cell surface antigen IgG2a antibody (Glaxo Wellcome/Centocor); BEC2 which is a murine anti-idiotype (GD3 epitope) IgG antibody (ImClone System); IMC-C225 which is a chimeric anti-EGFR IgG antibody (ImClone System); VITAXIN™ which is a humanized anti-αVβ3 integrin antibody (Applied Molecular Evolution/MedImmune); Campath 1H/LDP-03 which is a humanized anti CD52 IgG1 antibody (Leukosite); Smart M195 which is a humanized anti-CD33 IgG antibody (Protein Design Lab/Kanebo); RITUXAN™ which is a chimeric anti-CD20 IgG1 antibody (IDEC Pharm/Genentech, Roche/Zettyaku); LYMPHOCIDE™ which is a humanized anti-CD22 IgG antibody (Immunomedics); LYMPHOCIDE™ Y-90 (Immunomedics); Lymphoscan (Tc-99m-labeled; radioimaging; Immunomedics); Nuvion (against CD3; Protein Design Labs); CM3 is a humanized anti-ICAM3 antibody (ICOS Pharm); IDEC-114 is a primatied anti-CD80 antibody (IDEC Pharm/Mitsubishi); ZEVALIN™ is a radiolabelled murine anti-CD20 antibody (IDEC/Schering AG); IDEC-131 is a humanized anti-CD40L antibody (IDEC/Eisai); IDEC-151 is a primatized anti-CD4 antibody (IDEC); IDEC-152 is a primatized anti-CD23 antibody (IDEC/Seikagaku); SMART anti-CD3 is a humanized anti-CD3 IgG (Protein Design Lab); 5G1.1 is a humanized anti-complement factor 5 (C5) antibody (Alexion Pharm); D2E7 is a humanized anti-TNF-α antibody (CAT/BASF); CDP870 is a humanized anti-TNF-α Fab fragment (Celltech); IDEC-151 is a primatized anti-CD4 IgG1 antibody (IDEC Pharm/SmithKline Beecham); MDX-CD4 is a human anti-CD4 IgG antibody (Medarex/Eisai/Genmab); CD20-sreptavidin (+biotin-yttrium 90; NeoRx); CDP571 is a humanized anti-TNF-α IgG4 antibody (Celltech); LDP-02 is a humanized anti-α4β7 antibody (LeukoSite/Genentech); OrthoClone OKT4A is a humanized anti-CD4 IgG antibody (Ortho Biotech); ANTOVA™ is a humanized anti-CD40L IgG antibody (Biogen); ANTEGREN™ is a humanized anti-VLA-4 IgG antibody (Elan); and CAT-152 is a human anti-TGF-β$_2$ antibody (Cambridge Ab Tech).

In certain embodiments of the present invention passive immunotherapies, such as, conjugated monoclonal antibodies can be used in combination with the bis(thio hydrazide amides) described herein to treat cancer in the methods of the present invention. Examples of these conjugated monoclonal antibodies include, but are not limited to Radiolabeled antibody Ibritumomab tiuxetan (Zevalin) which delivers radioactivity directly to cancerous B lymphocytes and is used to treat, for example, B cell non-Hodgkin lymphoma; radiolabeled antibody Tositumomab (Bexxar) which is used to treat, for example, certain types of non-Hodgkin lymphoma; and immunotoxin Gemtuzumab ozogamicin (Mylotarg) which contains calicheamicin and is used to treat, for example, acute myelogenous leukemia (AML). BL22 is a conjugated monoclonal antibody for treating, for example, hairy cell leukemia, immunotoxins for treating, for example, leukemias, lymphomas, and brain tumors, and radiolabeled antibodies such as OncoScint for example, for colorectal and ovarian cancers and ProstaScint for example, for prostate cancers.

In certain embodiments of the present invention targeted therapies containing toxins can be used in combination with the bis(thio hydrazide amides) described herein to treat cancer in the methods of the present invention. Targeted therapies containing toxins are toxins linked to growth factors and do not contain antibodies, for example, denileukin diftitox (Ontak) which can be used to treat, for example, skin lymphoma (cutaneous T cell lymphoma) in combination with the bis (thiohydrazide amides) described herein.

The present invention also includes the use of adjuvant immunotherapies in combination with the bis(thio hydrazide amides) described herein include, such adjuvant immunotherapies include, but are not limited to, cytokines, such as granulocyte-macrophage colony-stimulating factor (GM-CSF), granulocyte-colony stimulating factor (G-CSF), macrophage inflammatory protein (MIP)-1-alpha, interleukins (including IL-1, IL-2, IL-4, IL-6, IL-7, IL-12, IL-15, IL-18, IL-21, and IL-27), tumor necrosis factors (including TNF-alpha), and interferons (including IFN-alpha, EFN-beta, and IFN-gamma); aluminum hydroxide (alum); Bacille Calmette-Guérin (BCG); Keyhole limpet hemocyanin (KLH); Incomplete Freund's adjuvant (IFA); QS-21; DETOX; Levamisole; and Dinitrophenyl (DNP), and combinations thereof, such as, for example, combinations of, interleukins, for example, IL-2 with other cytokines, such as IFN-alpha.

In certain embodiments the immunotherapies described herein can be used in combination with the bis(thio hydrazide amides) described herein for use in the methods of the present invention. In one such embodiment, the method of the present invention is a method of treating melanoma with a combination of an effective amount of a bisthio(hydrazide amide), hyperthermia treatment, and optionally an effective amount of an immunotherapy.

In certain embodiments the immunotherapies described herein can be used in combination with the bis(thio hydrazide amides) described herein for use in the methods of the present invention. In one such embodiment, the method of the present invention is a method of treating melanoma with a combination of an effective amount of a bisthio(hydrazide amide), radiotherapy, and optionally an effective amount of an immunotherapy.

Examples of immunotherapies which are suitable in this method and other methods of the invention include:

IFN-alpha and IL-2 for treatment of, for example, metastatic melanoma; BCG in combination with, for example, melanoma vaccines and optionally other immunotherapies; tumor-infiltrating lymphocytes; human monoclonal antibodies to ganglioside antigens, to treat, for example, cutaneous recurrent melanoma tumors; autologous and allogeneic tumor cell vaccines, antigen vaccines (including polyvalent antigen vaccines), dendritic cell vaccines; viral vaccines; combined IL-12/TNF-alpha immunotherapy to treat, foe example, B16F10 melanoma, Lewis lung (LL/2) carcinoma and L1 sarcoma; and IFN-alpha to treat, for example, malignant melanoma, chronic myelogenous leukemia (CML), hairy cell leukemia, and Kaposi's sarcoma.

In certain embodiments the immunotherapies described herein can be used in combination with the bis(thio hydrazide amides) described herein for use in the methods of the present invention. In one such embodiment, the method of the present invention is a method of treating renal cancer with a combination of an effective amount of a bisthio(hydrazide amide), hyperthermia treatment, and optionally an effective amount of an immunotherapy.

In certain embodiments the immunotherapies described herein can be used in combination with the bis(thio hydrazide amides) described herein for use in the methods of the present invention. In one such embodiment, the method of the present invention is a method of treating renal cancer with a combination of an effective amount of a bisthio(hydrazide amide), radiotherapy, and optionally an effective amount of an immunotherapy Examples of immunotherapies which are suitable in this method and other methods of the invention include:

IFN-alpha and IL-2 alone or in combination; combination of IL-2, interferon and chemotherapy; a tumor cell vaccine plus the adjuvant BCG; DNA vaccines and tumor-infiltrating lymphocytes; and chimeric bispecific G250/anti-CD3 monoclonal antibodies.

In certain embodiments the present invention is directed to administering an effective amount of a bis(thiohydrazide amide and an effective amount of rapamycin, geldenamyci, 17-allylamino, 17-demethoxygeldanamycin, histone deacetylase inhibitors, topoisomerase I inhibitors, thioredoxin 1 inhibitors, mictotubule disruptors, Epothilone, EP0906, an allogenic bone marrow stem cell transplantation, allogenic hematopoietic stem cell transplantation, PTK 787, SU 11248 bey 43-9006, medroxyprogestterone, ABX-EGF, imatinib mesylate, ZD1839, SU5416, bortezomib (PS-341), BAY 59-8862, HSPPC-96, thalidomide ABT-510, CCI-779 or RAD-001, or combinations of bevacizumab and thalidomide, or combinations of thalidomide and IFN-α, or combinations of FUNIL and thalidomide, or combinations of CAPE and IFN-α, or combinations of gemcitabine (GEM) and capecitabine (CAPE), or combinations of thalidomide and IL-2, and thalidomide, or combinations of HSPPC-96 and IL-2 or a combination of bevacizumab, IL-2, interferon and optionally an additional anti-cancer agent.

In a particular embodiment, the method of the present invention comprises administering to a subject with an immunosensitive cancer an effective amount of the bis(thiohydrazide amide) described herein, hyperthermia treatment, an effective amount of the immunotherapy described herein and one or more additional anti-cancer therapies selected from: anti-cancer agents/drugs, biological therapy, radiation therapy, anti-angiogenesis therapy, gene therapy or hormonal therapy.

In a particular embodiment, the method of the present invention comprises administering to a subject with an immunosensitive cancer an effective amount of the bis(thiohydrazide amide) described herein, radition therapy, an effective amount of the immunotherapy described herein and one or more additional anti-cancer therapies selected from: anti-cancer agents/drugs, biological therapy, hyperthermia treatment, anti-angiogenesis therapy, gene therapy or hormonal therapy.

Examples of anti-cancer agents/drugs are described below.

In one embodiment the anti-cancer agents/drug is, for example, Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; ilmofosine; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride.

Other anti-cancer agents/drugs include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; antidorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorlns; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; episteride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer. Preferred additional anti-cancer drugs are 5-fluorouracil and leucovorin.

Agents that can be used in the methods of the invention in combination with the bis(thiohydrazide amides) in the methods disclosed herein, include but are not limited to, alkylating agents, antimetabolites, natural products, or hormones. Examples of alkylating agents useful in the methods of the invention include but are not limited to, nitrogen mustards (e.g., mechloroethamine, cyclophosphamide, chlorambucil, melphalan, etc.), ethylenimine and methylmelamines (e.g., hexamethlymelamine, thiotepa), alkyl sulfonates (e.g., busulfan), nitrosoureas (e.g., carmustine, lomusitne, semustine, streptozocin, etc.), or triazenes (decarbazine, etc.). Examples of antimetabolites useful in the methods of the invention include but are not limited to folic acid analog (e.g., methotrexate), or pyrimidine analogs (e.g., fluorouracil, floxouridine, Cytarabine), purine analogs (e.g., mercaptopurine, thioguanine, pentostatin). Examples of natural products useful in the methods of the invention include but are not limited to vinca alkaloids (e.g., vinblastin, vincristine), epipodophyllotoxins (e.g., etoposide, teniposide), antibiotics (e.g., actinomycin D, daunorubicin, doxorubicin, bleomycin, plicamycin, mitomycin) or enzymes (e.g., L-asparaginase). Examples of hormones and antagonists useful for the treatment or prevention of cancer in the methods of the invention include but are not limited to adrenocorticosteroids (e.g., prednisone), progestins (e.g., hydroxyprogesterone caproate, megestrol acetate, medroxyprogesterone acetate), estrogens (e.g., diethlystilbestrol, ethinyl estradiol), antiestrogen (e.g., tamoxifen), androgens (e.g., testosterone propionate, fluoxymesterone), antiandrogen (e.g., flutamide), gonadotropin releasing hormone analog (e.g., leuprolide). Other agents that can be used in the methods of the invention for the treatment or prevention of cancer include platinum coordination complexes (e.g., cisplatin, carboblatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide).

Preferably, the anti-cancer agent/drug is an agent that stabilizes mictotubules. As used herein, a "microtubulin stabilizer" means an anti-cancer agent/drug which acts by arresting cells in the G2-M phases due to stabilization of microtubules. Examples of microtubulin stabilizers include ACLITAXEL® and Taxol® analogues. Additional examples of microtubulin stabilizers included without limitation the following marketed drugs and drugs in development: Discodermolide (also known as NVP-XX-A-296); Epothilones (such as Epothilone A, Epothilone B, Epothilone C (also known as desoxyepothilone A or dEpoA); Epothilone D (also referred to as KOS-862, dEpoB, and desoxyepothilone B); Epothilone E; Epothilone F; Epothilone B N-oxide; Epothilone A N-oxide; 16-aza-epothilone B; 21-aminoepothilone B (also known as BMS-310705); 21-hydroxyepothilone D (also known as Desoxyepothilone F and dEpoF), 26-fluoroepothilone); FR-182877 (Fujisawa, also known as WS-9885B), BSF-223651 (BASF, also known as ILX-651 and LU-223651); AC-7739 (Ajinomoto, also known as AVE-8063A and CS-39.HCl); AC-7700 (Ajinomoto, also known as AVE-8062, AVE-8062A, CS-39-L-Ser.HCl, and RPR-258062A); Fijianolide B; Laulimalide; Caribaeoside; Caribaeolin; Taccalonolide; Eleutherobin; Sarcodictyin; Laulimalide; Dictyostatin-1; Jatrophane esters; and analogs and derivatives thereof.

As used herein, a "microtubulin inhibitor" means an anti-cancer agent which acts by inhibiting tubulin polymerization or microtubule assembly. Examples of microtubulin inhibitors include without limitation the following marketed drugs and drugs in development: Erbulozole (also known as R-55104); Dolastatin 10 (also known as DLS-10 and NSC-376128); Mivobulin isethionate (also known as CI-980); Vincristine; NSC-639829; ABT-751 (Abbot, also known as E-7010); Altorhyrtins (such as Altorhyrtin A and Altorhyrtin C); Spongistatins (such as Spongistatin 1, Spongistatin 2, Spongistatin 3, Spongistatin 4, Spongistatin 5, Spongistatin 6, Spongistatin 7, Spongistatin 8, and Spongistatin 9); Cemadotin hydrochloride (also known as LU-103793 and NSC-D-669356); Auristatin PE (also known as NSC-654663); Soblidotin (also known as TZT-1027), LS-4559-P (Pharmacia, also known as LS-4577); LS-4578 (Pharmacia, also known as LS-477-P); LS-4477 (Pharmacia), LS-4559 (Pharmacia); RPR-112378 (Aventis); Vincristine sulfate; DZ-3358 (Daiichi); GS-164 (Takeda); GS-198 (Takeda); KAR-2 (Hungarian Academy of Sciences); SAH49960 (Lilly/Novartis); SDZ-268970 (Lilly/Novartis); AM-97 (Armad/Kyowa Hakko); AM-132 (Armad); AM-138 (Armad/Kyowa Hakko); IDN-5005 (Indena); Cryptophycin 52 (also known as LY-355703); Vitilevuamide; Tubulysin A; Canadensol; Centaureidin (also known as NSC-106969); T-138067 (Tularik, also known as T-67, TL-138067 and TI-138067); COBRA-1 (Parker Hughes Institute, also known as DDE-261 and WHI-261); H10 (Kansas State University); H16 (Kansas State University); Oncocidin A1 (also known as BTO-956 and DIME); DDE-313 (Parker Hughes Institute); SPA-2 (Parker Hughes Institute); SPA-1 (Parker Hughes Institute, also known as SPIKET-P); 3-IAABU (Cytoskeleton/Mt. Sinai School of Medicine, also known as MF-569); Narcosine (also known as NSC-5366); Nascapine, D-24851 (Asta Medica), A-105972 (Abbott); Hemiasterlin; 3-BAABU (Cytoskeleton/Mt. Sinai School of Medicine, also known as MF-191); TMPN (Arizona State University); Vanadocene acetylacetonate; T-138026 (Tularik); Monsatrol; Inanocine (also known as NSC-698666); 3-IAABE (Cytoskeleton/Mt. Sinai School of Medicine); A-204197 (Abbott); T-607 (Tularik, also known as T-900607); RPR-115781 (Aventis); Eleutherobins (such as Desmethyleleutherobin, Desaetyleleutherobin, Isoeleutherobin A, and Z-Eleutherobin); Halichondrin B; D-64131 (Asta Medica); D-68144 (Asta Medica); Diazonamide A; A-293620 (Abbott); NPI-2350 (Nereus); TUB-245 (Aventis); A-259754 (Abbott); Diozostatin; (−)-Phenylahistin (also known as NSCL-96F037); D-68838 (Asta Medica); D-68836 (Asta Medica); Myoseverin B; D-43411 (Zentaris, also known as D-81862); A-289099 (Abbott); A-318315 (Abbott); HTI-286 (also known as SPA-110, trifluoroacetate salt) (Wyeth); D-82317 (Zentaris); D-82318 (Zentaris); SC-12983 (NCI); Resverastatin phosphate sodium; BPR-0Y-007 (National Health Research Institutes); SSR-250411 (Sanofi); Combretastatin A4; and analogs and derivatives thereof.

Taxol®, also referred to as "Paclitaxel", is a well-known anti-cancer drug which acts by enhancing and stabilizing microtubule formation. Many analogs of Taxol® are known, including taxotere. Taxotere is also referred to as "Docetaxol". The structures of other Taxol® analogs are shown in below (and in U.S. application Ser. No. 11/157,213 the entire contents of which are incorporated herein by reference):

31
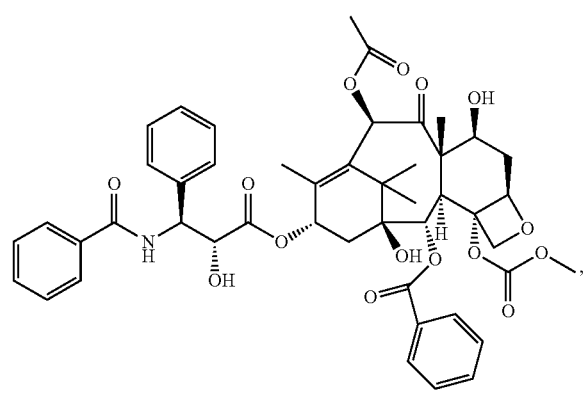
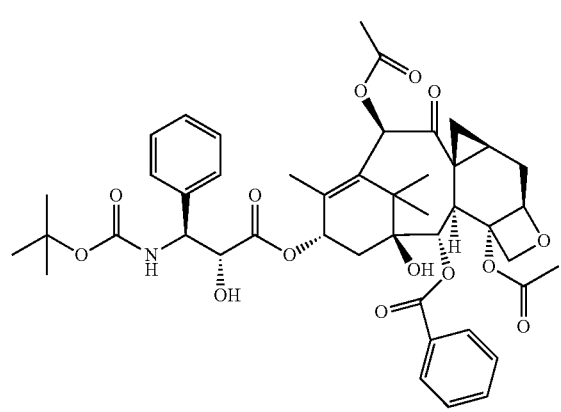
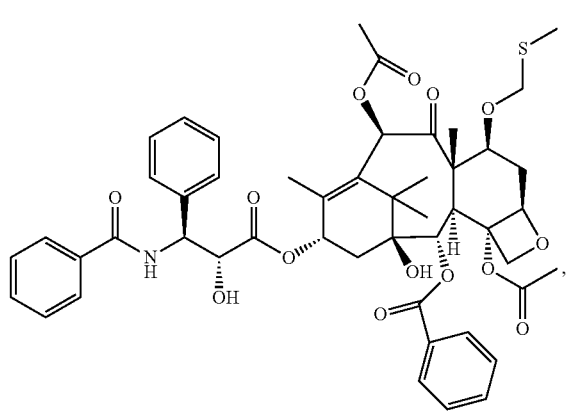
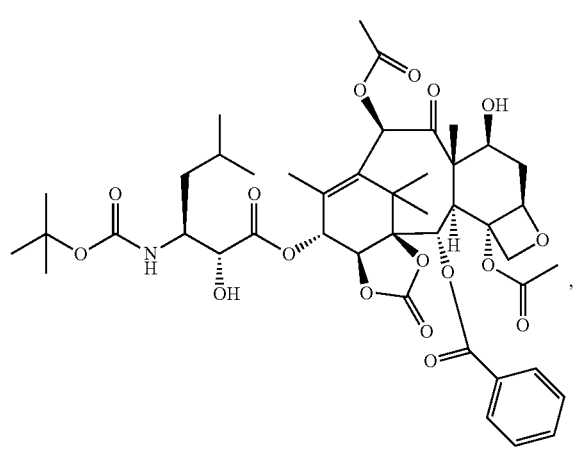
32
-continued
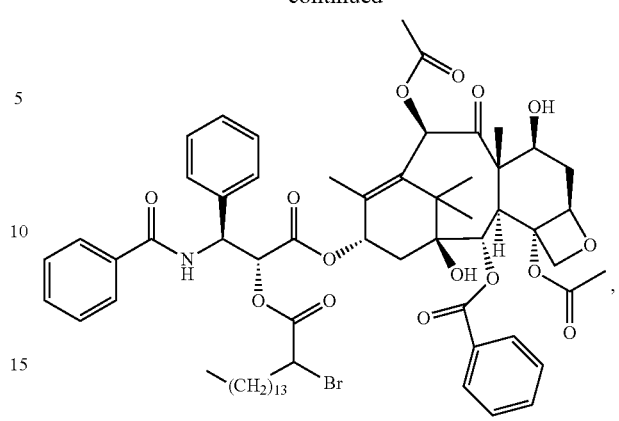
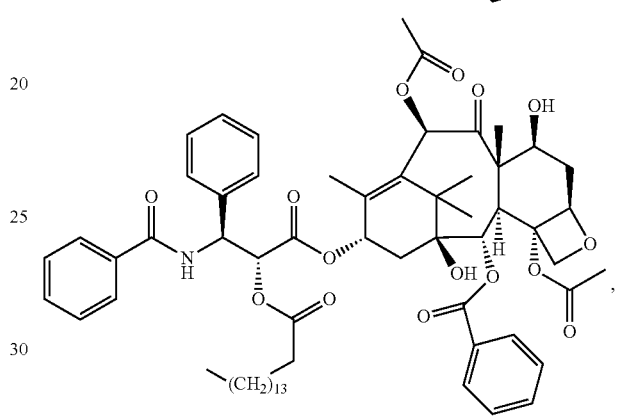
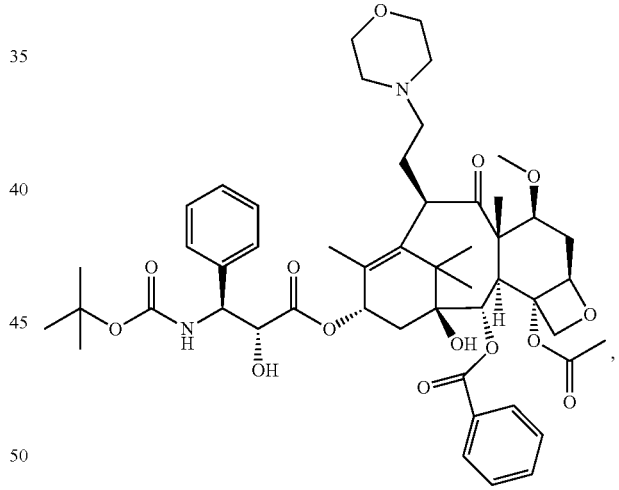
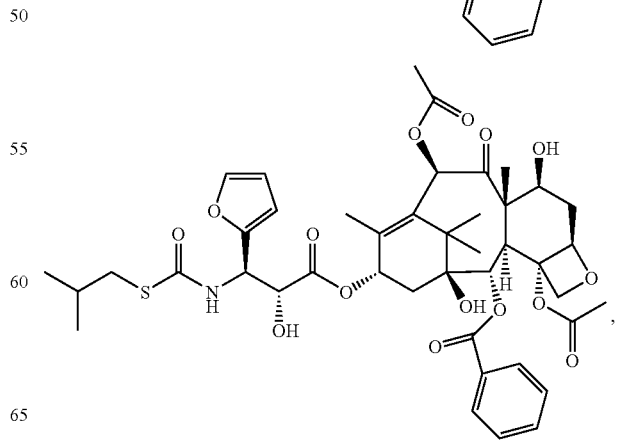

33
-continued
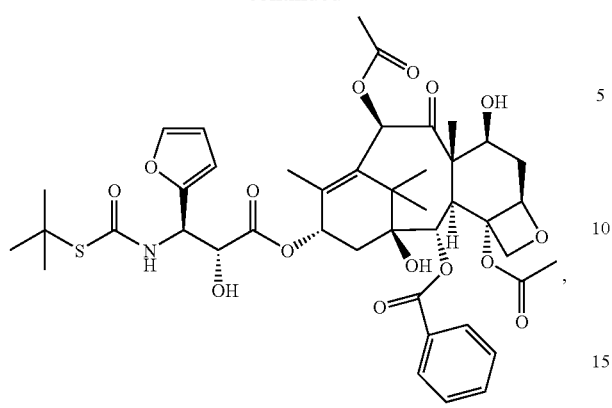
34
-continued
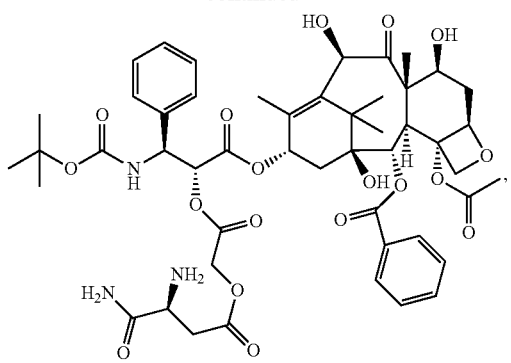
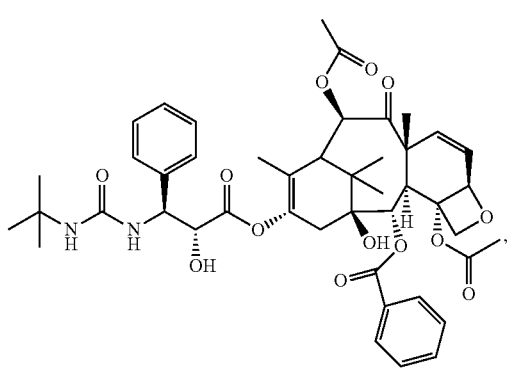
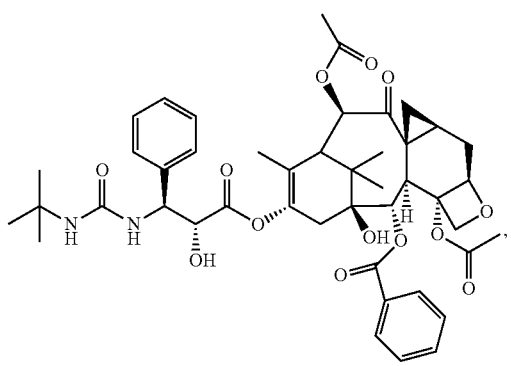

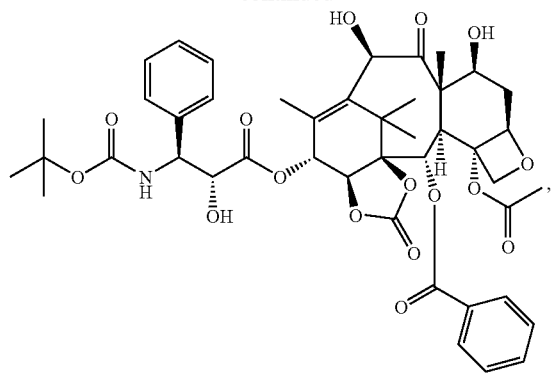

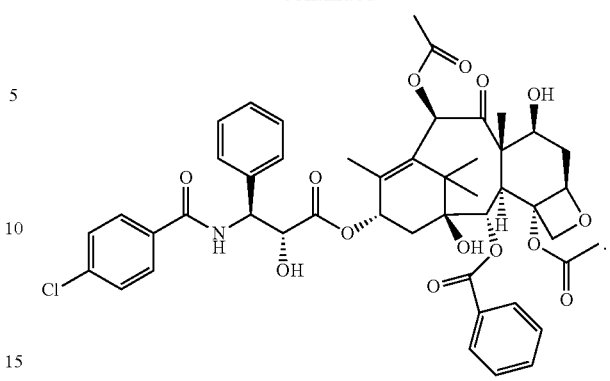

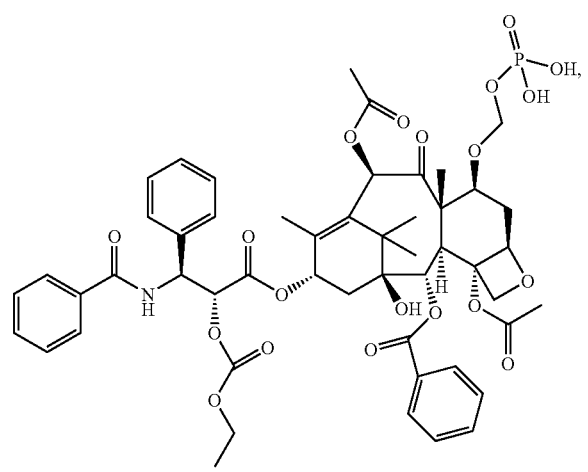

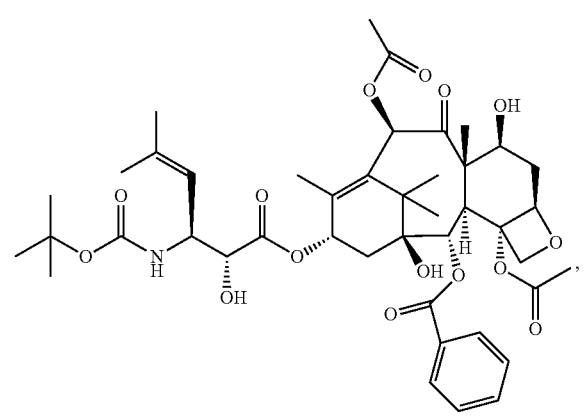

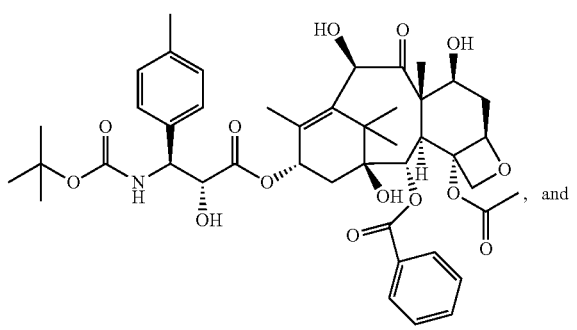

These compounds have the basic taxane skeleton as a common structure feature and have also been shown to have the ability to arrest cells in the G2-M phases due to stabilization of microtubules. Thus, a wide variety of substituents can decorate the taxane skeleton without adversely affecting biological activity. It is also apparent that zero, one or both of the cyclohexane rings of a Taxol® analog can have a double bond at the indicated positions. For clarity purposes, the basic taxane skeleton is shown below in Structural Formula (X):

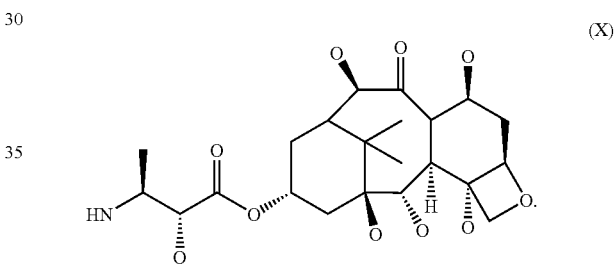

(X)

Double bonds have been omitted from the cyclohexane rings in the taxane skeleton represented by Structural Formula (X). The basic taxane skeleton can include zero or one double bond in one or both cyclohexane rings, as indicated in Structural Formulas (XI) and (XII) below. A number of atoms have also been omitted from Structural Formula (X) to indicate sites in which structural variation commonly occurs among Taxol® analogs. For example, substitution on the taxane skeleton with simply an oxygen atom indicates that hydroxyl, acyl, alkoxy or another oxygen-bearing substituent is commonly found at the site. These and other substitutions on the taxane skeleton can be made without losing the ability to enhance and stabilize microtubule formation. Thus, the term "taxol analog" is defined herein to mean a compound which has the basic taxol skeleton and which promotes microtubule formation. Taxol® analogs may be formulated as a nanoparticle colloidal composition to improve the infusion time and to eliminate the need to deliver the drug with Cremophor which causes hypersensitivity reactions in some patients. An example of a Taxol® analog formulated as a nanoparticle colloidal composition is ABI-007 which is a nanoparticle colloidal composition of protein-stabilized paclitaxel that is reconstituted in saline.

Typically, the Taxol® analogs used herein are represented by Structural Formula (XI) or (XII):

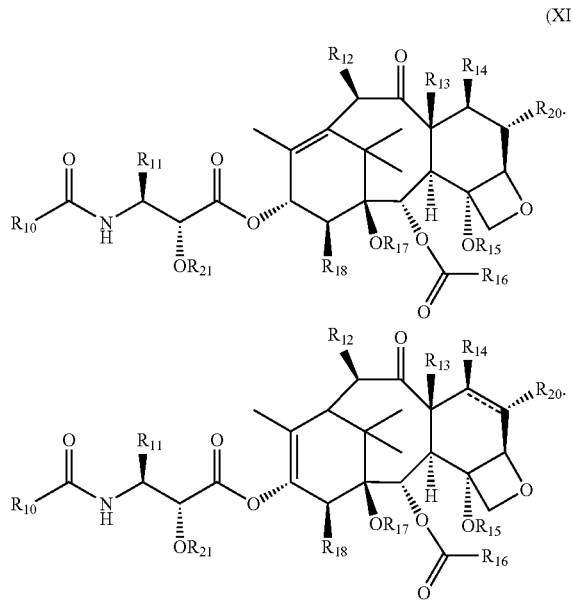

$R_{10}$ is a lower alkyl group, a substituted lower alkyl group, a phenyl group, a substituted phenyl group, —$SR_{19}$, —$NHR_{19}$ or —$OR_{19}$.

$R_{11}$ is a lower alkyl group, a substituted lower alkyl group, an aryl group or a substituted aryl group.

$R_{12}$ is —H, —OH, lower alkyl, substituted lower alkyl, lower alkoxy, substituted lower alkoxy, —O—C(O)-(lower alkyl), —O—C(O)-(substituted lower alkyl), —O—CH$_2$—O-(lower alkyl)-S—CH$_2$—O-(lower alkyl).

$R_{13}$ is —H, —CH$_3$, or, taken together with $R_{14}$, —CH$_2$—.

$R_{14}$ is —H, —OH, lower alkoxy, —O—C(O)-(lower alkyl), substituted lower alkoxy, —O—C(O)-(substituted lower alkyl), —O—CH$_2$—O—P(O)(OH)$_2$, —O—CH$_2$—O-(lower alkyl), —O—CH$_2$—S-(lower alkyl) or, taken together with $R_{20}$, a double bond.

$R_{15}$—H, lower acyl, lower alkyl, substituted lower alkyl, alkoxymethyl, alkthiomethyl, —OC(O)—O(lower alkyl), —OC(O)—O(substituted lower alkyl), —OC(O)—NH(lower alkyl) or —OC(O)—NH(substituted lower alkyl).

$R_{16}$ is phenyl or substituted phenyl.

$R_{17}$ is —H, lower acyl, substituted lower acyl, lower alkyl, substituted, lower alkyl, (lower alkoxy)methyl or (lower alkyl)thiomethyl.

$R_{18}$—H, —CH$_3$ or, taken together with $R_{17}$ and the carbon atoms to which $R_{17}$ and $R_{18}$ are bonded, a five or six membered a non-aromatic heterocyclic ring.

$R_{19}$ is a lower alkyl group, a substituted lower alkyl group, a phenyl group, a substituted phenyl group.

$R_{20}$ is —H or a halogen.

$R_{21}$ is —H, lower alkyl, substituted lower alkyl, lower acyl or substituted lower acyl.

Preferably, the variables in Structural Formulas (XI) and (XII) are defined as follows: $R_{10}$ is phenyl, tert-butoxy, —S—CH$_2$—CH—(CH$_3$)$_2$, —S—CH(CH$_3$)$_3$, —S—(CH$_2$)$_3$CH$_3$, —O—CH(CH$_3$)$_3$, —NH—CH(CH$_3$)$_3$, —CH=C(CH$_3$)$_2$ or para-chlorophenyl; $R_{11}$ is phenyl, (CH$_3$)$_2$CHCH$_2$—, -2-furanyl, cyclopropyl or para-toluoyl; $R_{12}$ is —H, —OH, CH$_3$CO— or —(CH$_2$)$_2$—N-morpholino; $R_{13}$ is methyl, or, $R_{13}$ and $R_{14}$, taken together, are —CH$_2$—;

$R_{14}$ is —H, —CH$_2$SCH$_3$ or —CH$_2$—O—P(O)(OH)$_2$; $R_{15}$ is CH$_3$CO—;

$R_{16}$ is phenyl; $R_{17}$—H, or, $R_{17}$ and $R_{18}$, taken together, are —O—CO—O—;

$R_{18}$ is —H; $R_{20}$ is —H or —F; and $R_{21}$ is —H, —C(O)—CHBr—(CH$_2$)$_{13}$—CH$_3$ or —C(O)—(CH$_2$)$_{14}$—CH$_3$; —C(O)—CH$_2$—CH(OH)—COOH, —C(O)—CH$_2$—O—C(O)—CH$_2$CH(NH$_2$)—CONH$_2$, —C(O)—CH$_2$—O—CH$_2$CH$_2$OCH$_3$ or —C(O)—O—C(O)—CH$_2$CH$_3$.

A Taxol® analog can also be bonded to or be pendent from a pharmaceutically acceptable polymer, such as a polyacrylamide. One example of a polymer of this type is shown in US Application Publication No. 2006/0135595. The term "taxol analog", as it is used herein, includes such polymers.

In some embodiments, Taxol® anologs have a taxane skeleton represented by Structural Formula IX, wherein Z is O, S, or NR. Taxol® anologs that have the taxane skeleton shown in Structural Formula IX can have various substituents attached to the taxane skeleton and can have a double bond in zero, one or both of the cyclohexane rings as shown, for example in FIGS. 3-23.

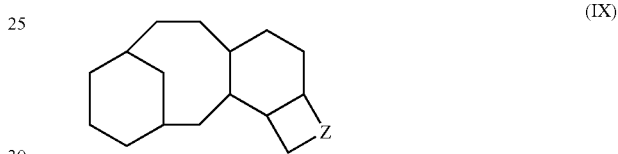

Various Taxol® analogs and Taxol® formulations are described in Hennenfent et al. (2006) *Annals of Oncology* 17:735-749; Gradishar (2006) *Expert Opin. Pharmacother.* 7(8): 1041-53; Attard et al. (2006) *Pathol Biol* 54(2):72-84; Straubinger et al. (2005) *Methods Enzymol.* 391:97-117; Ten Tije et al. (2003) *Clin Pharmacokinet.* 42(7):665-85; and Nuijen et al. (2001) *Invest New Drugs.* 19(2): 143-53, the entire teachings of which are incorporated herein by reference.

In a particular embodiment, the present invention is a method of treating a subject with a proliferative disease, such as cancer, comprising administering to the subject an effective amount of a bis(thiohydrazide amides) in combination with hyperthermia treatment, and an effective amount of a microtubulin stabilizer (e.g., taxol or taxotere). In one embodiment, renal cell carcinoma and melanoma are treated with the disclosed methods.

In a particular embodiment, the present invention is a method of treating a subject with a proliferative disease, such as cancer, comprising administering to the subject an effective amount of a bis(thiohydrazide amides), in combination with hyperthermia treatment, an effective amount of a microtubulin stabilizer (e.g., taxol or taxotere) and an effective amount of another anti-cancer agent as described herein. In one embodiment, renal cell carcinoma and melanoma are treated with the disclosed methods.

In a particular embodiment, the present invention is a method of treating a subject with a proliferative disease, such as cancer, comprising administering to the subject an effective amount of a bis(thiohydrazide amides), in combination with radiotherapy, and an effective amount of a microtubulin stabilizer (e.g., taxol or taxotere). In one embodiment, renal cell carcinoma and melanoma are treated with the disclosed methods.

In a particular embodiment, the present invention is a method of treating a subject with a proliferative disease, such as cancer, comprising administering to the subject an effective amount of a bis(thiohydrazide amides), in combination with radiotherapy, an effective amount of a microtubulin stabilizer (e.g., taxol or taxotere) and an effective amount of another anti-cancer agent as described herein. In one embodiment, renal cell carcinoma and melanoma are treated with the disclosed methods.

In a particular embodiment, the anti-cancer agent is selected from the group consisting of dacarbazine (brand name DTIC), temozolomide (brand name Temodar), cisplatin, carmustine (also known as BCNU), fotemustine, vindesine, vincristine sorafenib and bleomycin. In another particular embodiment, the anti-cancer agent is selected from the group carboplatin, tamoxifen and Nolvadex. In another particular embodiment the anti-cancer agent is selected from the group vinablastine, G-CSF and navelbine. In another particular embodiment the anti-cancer agent is selected from the combinations of drugs selected from dacarbazine and G-CSF or carboplatin and sorafenib. In another particular embodiment the anti-cancer agent is selected from the combinations of drugs selected from dacarbazine and Granulocyte colony-stimulating factor (G-CSF), Carboplatin and Sorafenib, dacarbazine, carmustine cisplatin, and tamoxifen, or cisplatin, vinblastine, and dacarbazine.

In certain embodiments the present invention is directed to administering to a subject with an immunosensitive cancer, in particular melanoma, with an effective amount of a bis(thiohydrazide amide), in combination with hyperthermia or radiotherapy, an effective amount of an immunotherapy and optionally one or more additional anti-cancer agents, wherein the immunotherapy and anti-cancer agent are selected from Interleukin2 (IL2; Proleukin), Interferon (IFN alfa-2b, IFN), IFN (interferon) in combination, MDX 010, MDX-1379, Dacarbazide, Genasense, Cisplatin, vinblastine, Carmustine, dacarbazine, or Nolvadex, or selected from the following groups:
Biologic Response Modifiers:
Interleukin2 (IL2; Proleukin)
Interferon (IFN alfa-2b, IFN)
Biochemotherapy:
IFN (interferon)
MDX 010+IL-2
MDX010+MDX-1379
Dacarbazide+Genasense
Dacarbazide+Cisplatin+IFN
Dacarbazide+Cisplatin+IFN+IL-2
Cisplatin+vinblastine+dacarbazine+IL-2+IFN
Carmustine+dacarbazine+cisplatin+Nolvadex+IL-2+IFN.

In certain embodiments the present invention is directed to administering to a subject with an immunosensitive cancer, in particular renal cell carcinoma, with an effective amount of a bis(thiohydrazide amide), in combination with hyperthermia or radiotherapy, an effective amount of an immunotherapy and optionally one or more additional anti-cancer agents, wherein the immunotherapy and anti-cancer agent are selected from of rapamycin, geldenamyci, 17-allylamino, 17-demethoxygeldanamycin, histone deacetylase inhibitors, topoisomerase I inhibitors, thioredoxin 1 inhibitors, mictotubule disruptors, Epothilone, EP0906, an allogenic bone marrow stem cell transplantation, allogenic hematopoietic stem cell transplantation, PTK 787, SU 11248 bey 43-9006, medroxyprogestterone, ABX-EGF, imatinib mesylate, ZD1839, SU5416, bortezomib (PS-341), BAY 59-8862, HSPPC-96, thalidomide ABT-510, CCI-779 or RAD-001, or combinations of bevacizumab and thalidomide, or combinations of thalidomide and IFN-α, or combinations of FUNIL and thalidomide, or combinations of CAPE and IFN-α, or combinations of gemcitabine (GEM) and capecitabine (CAPE), or combinations of thalidomide and IL-2, and thalidomide, or combinations of HSPPC-96 and IL-2 or a combination of bevacizumab, IL-2, interferon and optionally an additional anti-cancer agent, or a combination of IFN-α and IL-2.

In certain embodiments the present invention is directed to administering to a subject with an immunosensitive cancer, in particular renal cell carcinoma, with an effective amount of a bis(thiohydrazide amide), in combination with hyperthermia or radiotherapy, and an effective amount of an immunotherapy which is a combination of IFN-α and IL-2.

The above methods disclosed in the immediately preceding paragraph are particularly advantageous in treating melanoma.

Numerous non-cancer diseases involve excessive or hyperproliferative cell growth, termed hyperplasia. As used herein, the terms "proliferative disorder", "hyperproliferative disorder," and "cell proliferation disorder" are used interchangeably to mean a disease or medical condition involving pathological growth of cells. Such disorders include cancer.

Non-cancerous proliferative disorders include smooth muscle cell proliferation, systemic sclerosis, cirrhosis of the liver, adult respiratory distress syndrome, idiopathic cardiomyopathy, lupus erythematosus, retinopathy, e.g., diabetic retinopathy or other retinopathies, cardiac hyperplasia, reproductive system associated disorders such as benign prostatic hyperplasia and ovarian cysts, pulmonary fibrosis, endometriosis, fibromatosis, harmatomas, lymphangiomatosis, sarcoidosis, desmoid tumors and the like.

Smooth muscle cell proliferation includes proliferative vascular disorders, for example, intimal smooth muscle cell hyperplasia, restenosis and vascular occlusion, particularly stenosis following biologically- or mechanically-mediated vascular injury, e.g., vascular injury associated with balloon angioplasty or vascular stenosis. Moreover, intimal smooth muscle cell hyperplasia can include hyperplasia in smooth muscle other than the vasculature, e.g., hyperplasia in bile duct blockage, in bronchial airways of the lung in asthma patients, in the kidneys of patients with renal interstitial fibrosis, and the like.

Non-cancerous proliferative disorders also include hyperproliferation of cells in the skin such as psoriasis and its varied clinical forms, Reiter's syndrome, pityriasis rubra pilaris, and hyperproliferative variants of disorders of keratinization (e.g., actinic keratosis, senile keratosis), scleroderma, and the like.

Cancers which can be treated by the methods of the present invention include, but are not limited to, human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, colorectal cancer, anal carcinoma, esophageal cancer, gastric cancer, hepatocellular cancer, bladder cancer, endometrial cancer, pancreatic cancer, breast cancer, ovarian cancer, prostate cancer, stomach cancer, atrial myxomas, squamous cell carcinoma, basal cell carcinoma, adenocarcinoma, sweat gland carcinoma, sebaceous gland carcinoma, thyroid and parathyroid neoplasms, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, non-small-cell lung cancer, bladder carcinoma, epithelial carcinoma, glioma, pituitary neoplasms, astrocytoma, medulloblastoma, craniopharyngioma, ependymoma, pinealoma, hemangioblastoma, acoustic neuroma, schwannomas, oligodendroglioma, meningioma, spinal cord tumors, melanoma, neuroblastoma, pheochromocytoma, Types 1-3 endocrine neoplasia, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrobm's macroglobulinemia, and heavy chain disease.

Other examples of leukemias include acute and/or chronic leukemias, e.g., lymphocytic leukemia (e.g., as exemplified by the p388 (murine) cell line), large granular lymphocytic leukemia, and lymphoblastic leukemia; T-cell leukemias, e.g., T-cell leukemia (e.g., as exemplified by the CEM, Jurkat, and HSB-2 (acute), YAC-1 (murine) cell lines), T-lymphocytic leukemia, and T-lymphoblastic leukemia; B cell leukemia (e.g., as exemplified by the SB (acute) cell line), and B-lymphocytic leukemia; mixed cell leukemias, e.g., B and T cell leukemia and B and T lymphocytic leukemia; myeloid leukemias, e.g., granulocytic leukemia, myelocytic leukemia (e.g., as exemplified by the HL-60 (promyelocyte) cell line), and myelogenous leukemia (e.g., as exemplified by the K562 (chronic) cell line); neutrophilic leukemia; eosinophilic leukemia; monocytic leukemia (e.g., as exemplified by the THP-1 (acute) cell line); myelomonocytic leukemia; Naegeli-type myeloid leukemia; and nonlymphocytic leukemia. Other examples of leukemias are described in Chapter 60 of The Chemotherapy Sourcebook, Michael C. Perry Ed., Williams & Williams (1992) and Section 36 of Holland Frie Cancer Medicine 5th Ed., Bast et al. Eds., B.C. Decker Inc. (2000). The entire teachings of the preceding references are incorporated herein by reference.

In one embodiment, the methods of the present invention include treating cancers including, but not limited to, non-solid tumors such as multiple myeloma, T-leukemia (e.g., as exemplified by Jurkat and CEM cell lines); B-leukemia (e.g., as exemplified by the SB cell line); promyelocytes (e.g., as exemplified by the HL-60 cell line); uterine sarcoma (e.g., as exemplified by the MES-SA cell line); monocytic leukemia (e.g., as exemplified by the THP-1 (acute) cell line); and lymphoma (e.g., as exemplified by the U937 cell line).

Immunosensitve cancers respond to immunotherapy, i.e., agents that stimulate the immune system. Examples of immunosensitive cancers include, renal cell carcinoma, melanoma, multiple myeloma, myeloma, lymphoma, non-small-cell lung cancer, bladder cancer, prostate cancer, squamous cell carcinoma, basal cell carcinoma, fibrosarcoma, malignant brain tumors, Kaposi's Sarcoma, chronic myelogenous leukemia (CML) and hairy cell leukemia.

In certain embodiments, the present invention is directed to preventing or delaying the recurrence of a proliferative disease, such as cancer, in subjects who have been treated for the proliferative disease, such as cancer, comprising administering an effective amount of

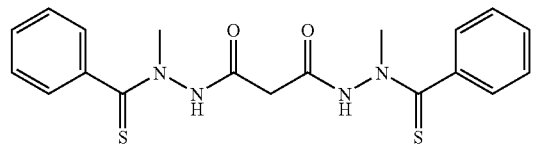

or a tautomer, pharmaceutically acceptable salt, solvate, clathrate, or prodrug thereof, in combination with hyperthermia, and optionally a microtubulin stabilizer, such as, taxol or taxotere.

In certain embodiments, the present invention is directed to preventing or delaying the recurrence of a proliferative disease, such as cancer, in subjects who have been treated for the proliferative disease, such as cancer, comprising administering an effective amount of

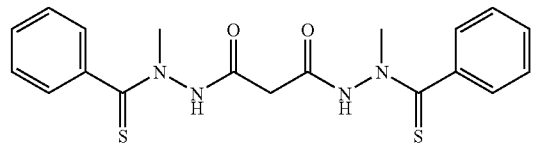

or a tautomer, pharmaceutically acceptable salt, solvate, clathrate, or prodrug thereof, in combination with radiotherapy, and optionally a microtubulin stabilizer, such as, taxol or taxotere.

In certain embodiments, the present invention is directed to preventing or delaying the recurrence of an immunosensitive cancer selected from the group consisting of renal cell carcinoma, melanoma, multiple myeloma, myeloma, lymphoma, non-small-cell lung cancer, bladder cancer, prostate cancer, squamous cell carcinoma, basal cell carcinoma, fibrosarcoma, malignant brain tumors, Kaposi's Sarcoma, chronic myelogenous leukemia (CML) and hairy cell leukemia in subjects who have been treated for the cancer, comprising administering an effective amount of

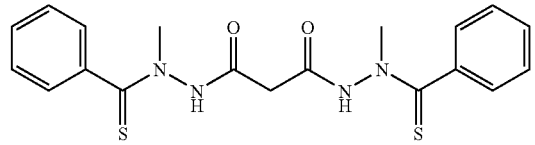

or a tautomer, pharmaceutically acceptable salt, solvate, clathrate, or prodrug thereof, in combination with hyperthermia, and optionally a microtubulin stabilizer, such as, taxol or taxotere.

In certain embodiments, the present invention is directed to preventing or delaying the recurrence of an immunosensitive cancer selected from the group consisting of renal cell carcinoma, melanoma, multiple myeloma, myeloma, lymphoma, non-small-cell lung cancer, bladder cancer, prostate cancer, squamous cell carcinoma, basal cell carcinoma, fibrosarcoma, malignant brain tumors, Kaposi's Sarcoma, chronic myelogenous leukemia (CML) and hairy cell leukemia in subjects who have been treated for the cancer, comprising administering an effective amount of

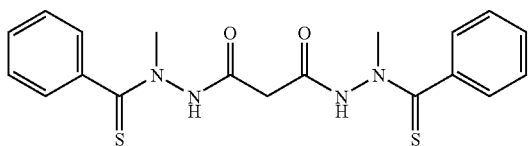

or a tautomer, pharmaceutically acceptable salt, solvate, clathrate, or prodrug thereof, in combination with radiotherapy, and optionally a microtubulin stabilizer, such as, taxol or taxotere.

In certain embodiments, the present invention is directed to treating a subject with a proliferative disease, such as cancer, comprising administering an effective amount of

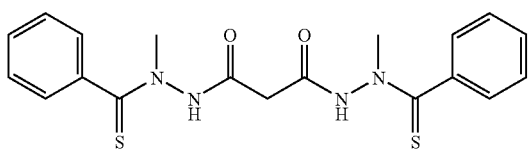

or a tautomer, pharmaceutically acceptable salt, solvate, clathrate, or prodrug thereof, in combination with hyperthermia, and optionally a microtubulin stabilizer, such as, taxol or taxotere.

In certain embodiments, the present invention is directed to treating a subject with a proliferative disease, such as cancer, comprising administering an effective amount of

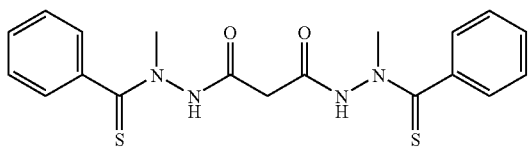

or a tautomer, pharmaceutically acceptable salt, solvate, clathrate, or prodrug thereof, in combination with radiotherapy, and optionally a microtubulin stabilizer, such as, taxol or taxotere.

In certain embodiments, the present invention is directed to treating a subject with an immunosensitive cancer selected from the group consisting of renal cell carcinoma, melanoma, multiple myeloma, myeloma, lymphoma, non-small-cell lung cancer, bladder cancer, prostate cancer, squamous cell carcinoma, basal cell carcinoma, fibrosarcoma, malignant brain tumors, Kaposi's Sarcoma, chronic myelogenous leukemia (CML) and hairy cell leukemia, comprising administering an effective amount of

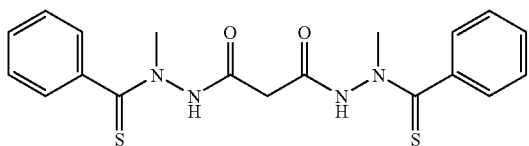

or a tautomer, pharmaceutically acceptable salt, solvate, clathrate, or prodrug thereof, in combination with hyperthermia, and optionally a microtubulin stabilizer, such as, taxol or taxotere.

In certain embodiments, the present invention is directed to treating a subject with an immunosensitive cancer selected from the group consisting of renal cell carcinoma, melanoma, multiple myeloma, myeloma, lymphoma, non-small-cell lung cancer, bladder cancer, prostate cancer, squamous cell carcinoma, basal cell carcinoma, fibrosarcoma, malignant brain tumors, Kaposi's Sarcoma, chronic myelogenous leukemia (CML) and hairy cell leukemia, comprising administering an effective amount of

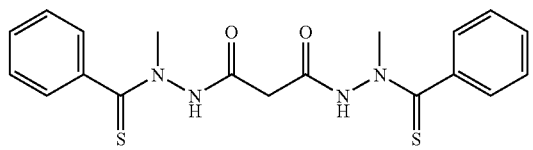

or a tautomer, pharmaceutically acceptable salt, solvate, clathrate, or prodrug thereof, in combination with radiotherapy, and optionally a microtubulin stabilizer, such as, taxol or taxotere.

In another embodiment, the disclosed method involves treating a subject with melanoma.

Melanoma, can be divided into five main subgroups:

i) Congenital Nevus: which is congenital and not malignant.

ii) Lentigo Maligna (Hutchinsons Freckle): which is a form of melanoma more common among the elderly population. These lesions may grow for years as an in-situ tumor before developing the more aggressive vertical growth phase. This type of melanoma is found most often in the damaged skin on the face, ears, arms, and upper trunk.

iii) Superficial Spreading Malignant Melanoma: is generally the most common form accounting for approximately 65% of diagnosed melanoma. The cancer presumably begins at one focus in the skin at the dermo-epidermal junction. It initially grows in a horizontal plane, along, just above and below the dermo-epidermal junction. This is referred to as the "radial" growth phase of melanoma and is clinically macular or only slightly elevated.

This melanoma travels along the top layer of the skin for a fairly long time before penetrating more deeply. The melanoma can be seen almost anywhere on the body, but is most likely to occur on the trunk in men, the legs in women, and the upper back in both. This type of melanoma is mainly found in the younger population.

iv) Acral Lentiginous Malignant Melanoma: as with superficial spreading malignant melanoma, acral lentiginous malignant melanoma also spreads superficially before penetrating more deeply. It is quite different from the others, though, as it usually appears as a black or brown discoloration under the nails or on the soles of the feet or palms of the hands. This type of melanoma is the most common melanoma in African-Americans and Asians, and the least common among Caucasians.

v) Nodular Malignant Melanoma: is a much less common form of melanoma. Unlike the other types, nodular melanoma, is usually invasive at the time it is first diagnosed. The malignancy is recognized when it becomes a bump. In this tumor, there is presumably no horizontal growth phase. The depth of the lesion appears to correlate with the prognosis of the subject, and nodular melanoma is less often amenable to definitive treatment than is the superficial spreading variety.

The methods of the present invention encompass treating all of the subgroups of melanoma defined above.

Melanoma can further be divided into four different stages, which are divided based on the progression of the disease:

Stage I

Cancer is found in the outer layer of the skin (epidermis) and/or the upper part of the inner layer of skin (dermis), but it has not spread to nearby lymph nodes. The tumor is less than 1.5 millimeters (1/16 of an inch) thick.

Stage II

The tumor is 1.5 millimeters to 4 millimeters (less than 1/6 of an inch) thick. It has spread to the lower part of the inner layer of skin (dermis), but not into the tissue below the skin or into nearby lymph nodes.

Stage III

Any of the following mean that the tumor is stage III:

The tumor is more than 4 millimeters (approximately 1/6 of an inch) thick.

The tumor has spread to the body tissue below the skin.

There are additional tumor growths within one inch of the original tumor (satellite tumors).

The tumor has spread to nearby lymph nodes or there are additional tumor growths (satellite tumors) between the original tumor and the lymph nodes in the area Stage IV The tumor has spread to other organs or to lymph nodes far away from the original tumor.

In another embodiment, the disclosed method involves treating a subject with renal cell carcinoma.

Renal cell carcinoma is the most common type of kidney cancer. It accounts for more than 90% of malignant kidney tumors. Renal cell carcinoma begins small and grows larger over time. Although renal cell carcinoma usually grows as a single mass within the kidney, a kidney may contain more than 1 tumor. Sometimes tumors may be found in both kidneys at the same time. Some renal cell carcinomas are noticed only after they have become quite large; most are found before they metastasize to other organs through the bloodstream or lymph vessels. Like most cancers, renal cell carcinoma is difficult to treat once it has metastasized.

There are five main types of renal cell carcinoma: clear cell, papillary, chromophobe, collecting duct, and "unclassified."

When viewed under a microscope, the individual cells that make up clear cell renal cell carcinoma appear very pale or clear. This is the most common form of renal cell carcinoma. About 80% of people with renal cell carcinoma have this kind of cancer.

Papillary renal cell carcinoma is the second most common type—about 10% to 15% of people have this kind. These cancers form little finger-like projections (called papillae) in some, if not most, of the tumor. Some doctors call these cancers chromophilic because the cells take up certain dyes used in preparing the tissue to be viewed under the microscope, causing them to appear pink.

Chromophobe renal carcinoma is the third most common type—accounting for about 5% of cases. The cells of these cancers are also pale, like the clear cells, but are much larger and have certain other features that can be recognized.

The fourth type, collecting duct renal carcinoma, is very rare. The major feature is that the cancer cells can form irregular tubes.

About 5% of renal cancers are unclassified because their appearance does not fit into any of the other categories.

Renal cell cancers are usually divided into four stages. The stage describes the cancer's size and how far it has spread beyond the kidney.

The Stage are generally defined below:

Stage I

The tumor is 7 cm or smaller and limited to the kidney. There is no spread to lymph nodes or distant organs.

Stage II:

The tumor is larger than 7 cm but is still limited to the kidney. There is no spread to lymph nodes or distant organs.

Stage III:

This includes:

any tumor that has spread to 1 nearby lymph node but not to more than 1 lymph node or other organs; and/or tumors that have not spread to lymph nodes or distant organs but have spread to the adrenal glands, to fatty tissue around the kidney, and/or have grown into the large vein (vena cava) leading from the kidney to the heart.

Stage IV:

This includes:

any cancers that have spread directly through the fatty tissue and beyond Gerota fascia, the fibrous tissue that surrounds the kidney; and/or any cancer that has spread to more than 1 lymph node near the kidney, or to any lymph node distant from the kidney, or to any distant organs such as the lungs, bone, or brain.

The disclosed methods include treating all five types of renal cell carcinoma in all four stages of disease progression as defined immediately above.

The first line treatment for renal cell carcinoma, when detected at an early stage, is often to surgically remove the cancer, for example, by radial nephrectomy. However, in many cases, as many as 20 or 30% of subjects develop metastatic (Stage III or IV) disease. For those subjects with metastatic (Stage III and IV) renal cell carcinoma, the prognosis is bleak.

In certain embodiments, the present invention is directed to treating renal cell carcinoma in a subject, comprising administering an effective amount of

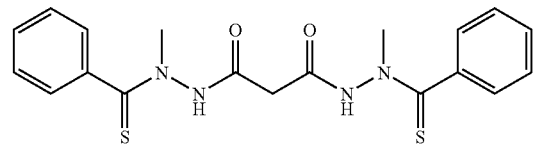

or a tautomer, pharmaceutically acceptable salt, solvate, clathrate, or prodrug thereof, in combination with hyperthermia, and optionally a microtubulin stabilizer, such as, taxol or taxotere.

In certain embodiments, the present invention is directed to preventing or delaying the recurrence of renal cell carcinoma in subjects who have been treated for Stage I, II, or III renal cell carcinoma, comprising administering an effective amount of

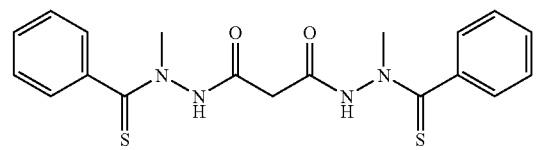

or a tautomer, pharmaceutically acceptable salt, solvate, clathrate, or prodrug thereof, in combination with hyperthermia, and optionally a microtubulin stabilizer, such as, taxol or taxotere.

In certain embodiments, the present invention is directed to treating renal cell carcinoma in a subject, comprising administering an effective amount of

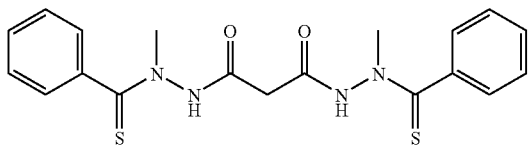

or a tautomer, pharmaceutically acceptable salt, solvate, clathrate, or prodrug thereof, in combination with radiotherapy, and optionally a microtubulin stabilizer, such as, taxol or taxotere.

In certain embodiments, the present invention is directed to preventing or delaying the recurrence of renal cell carcinoma in subjects who have been treated for Stage I, II, or III renal cell carcinoma, comprising administering an effective amount of

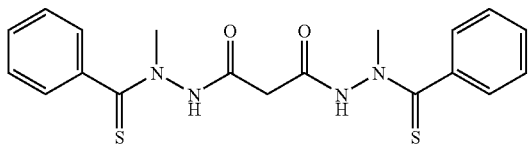

or a tautomer, pharmaceutically acceptable salt, solvate, clathrate, or prodrug thereof, in combination with radiotherapy, and optionally a microtubulin stabilizer, such as, taxol or taxotere.

In certain embodiments, the present invention is directed to preventing or delaying the recurrence of renal cell carcinoma in subjects who have been treated for Stage I, II, or III renal cell carcinoma, comprising administering an effective amount of a bis(thiohydrazide amide) described herein, in combination with hyperthermia, and optionally a microtubulin stabilizer, such as, taxol or taxotere.

In certain embodiments, the present invention is directed to preventing or delaying the recurrence of renal cell carcinoma in subjects who have been treated for Stage I, II, or III renal cell carcinoma, comprising administering an effective amount of a bis(thiohydrazide amide) described herein, in combination with hyperthermia, and an effective amount of a microtubulin stabilizer, such as, taxol or taxotere.

In certain embodiments, the present invention is directed to treating subjects with Stage III and IV renal cell carcinoma with an effective amount of a bis(thiohydrazide amide) described herein, in combination with hyperthermia, and an effective amount of a microtubulin stabilizer, such as, taxol or taxotere.

In certain embodiments, the present invention is directed to treating subjects with Stage IV renal cell carcinoma with an effective amount of a bis(thiohydrazide amide) described herein, in combination with hyperthermia, and an effective amount microtubulin stabilizer, such as, taxol or taxotere.

In certain embodiments, the present invention is directed to preventing or delaying the recurrence of renal cell carcinoma in subjects who have been treated for Stage I, II, or III renal cell carcinoma, comprising administering an effective amount of a bis(thiohydrazide amide) described herein, in combination with radiotherapy, and optionally a microtubulin stabilizer, such as, taxol or taxotere.

In certain embodiments, the present invention is directed to preventing or delaying the recurrence of renal cell carcinoma in subjects who have been treated for Stage I, II, or III renal cell carcinoma, comprising administering an effective amount of a bis(thiohydrazide amide) described herein, in combination with radiotherapy, and an effective amount of a microtubulin stabilizer, such as, taxol or taxotere.

In certain embodiments, the present invention is directed to treating subjects with Stage III and IV renal cell carcinoma with an effective amount of a bis(thiohydrazide amide) described herein, in combination with radiotherapy, and an effective amount of a microtubulin stabilizer, such as, taxol or taxotere.

In certain embodiments, the present invention is directed to treating subjects with Stage IV renal cell carcinoma with an effective amount of a bis(thiohydrazide amide) described herein, in combination with radiotherapy, and an effective amount microtubulin stabilizer, such as, taxol or taxotere.

In certain embodiments, the present invention is directed to preventing or delaying the recurrence of renal cell carcinoma in subjects who have been treated for Stage I, II, or III renal cell carcinoma, comprising administering an effective amount of

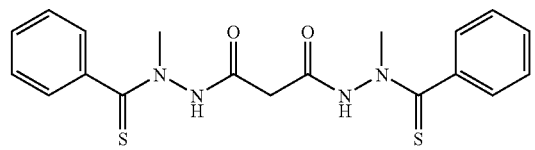

or a tautomer, pharmaceutically acceptable salt, solvate, clathrate, or prodrug thereof, in combination with hyperthermia, and optionally a microtubulin stabilizer, such as, taxol or taxotere.

In certain embodiments, the present invention is directed to preventing or delaying the recurrence of renal cell carcinoma in subjects who have been treated for Stage I, II, or III renal cell carcinoma, comprising administering an effective amount of

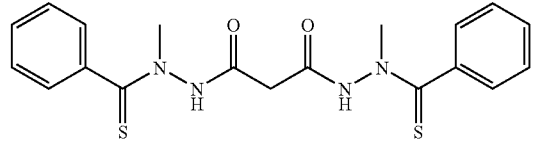

or a tautomer, pharmaceutically acceptable salt, solvate, clathrate, or prodrug thereof, in combination with hyperthermia, and an effective amount of a microtubulin stabilizer, such as, taxol or taxotere.

In certain embodiments, the present invention is directed to treating subjects with Stage III and IV renal cell carcinoma with an effective amount of

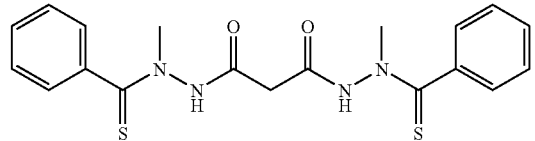

or a tautomer, pharmaceutically acceptable salt, solvate, clathrate, or prodrug thereof, in combination with hyperthermia, and an effective amount of a microtubulin stabilizer, such as, taxol or taxotere.

In certain embodiments, the present invention is directed to preventing or delaying the recurrence of renal cell carcinoma in subjects who have been treated for Stage I, II, or III renal cell carcinoma, comprising administering an effective amount of

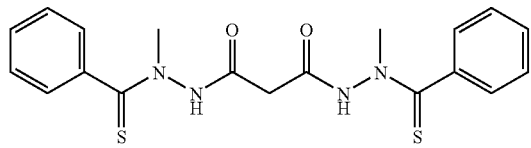

or a tautomer, pharmaceutically acceptable salt, solvate, clathrate, or prodrug thereof, in combination with radiotherapy, and optionally a microtubulin stabilizer, such as, taxol or taxotere.

In certain embodiments, the present invention is directed to preventing or delaying the recurrence of renal cell carcinoma in subjects who have been treated for Stage I, II, or III renal cell carcinoma, comprising administering an effective amount of

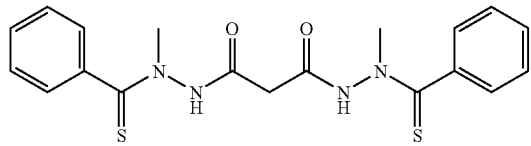

or a tautomer, pharmaceutically acceptable salt, solvate, clathrate, or prodrug thereof, in combination with radiotherapy, and an effective amount of a microtubulin stabilizer, such as, taxol or taxotere.

In certain embodiments, the present invention is directed to treating subjects with Stage III and IV renal cell carcinoma with an effective amount of

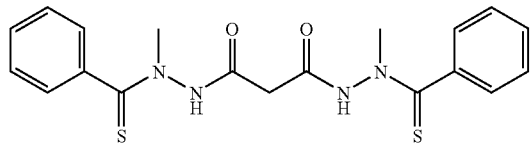

or a tautomer, pharmaceutically acceptable salt, solvate, clathrate, or prodrug thereof, in combination with radiotherapy, and an effective amount of a microtubulin stabilizer, such as, taxol or taxotere.

In another embodiment, the disclosed method involves treating subjects whose cancer has become "multi-drug resistant".

In a particular embodiment the disclosed method involves treating immunosensitive cancers, including, but not limited to, renal cell carcinoma, melanoma, multiple myeloma, myeloma, lymphoma, non-small-cell lung cancer, squamous cell carcinoma, basal cell carcinoma, fibrosarcoma, malignant brain tumors, Kaposi's Sarcoma, hairy cell leukemia, ovarian cancer, breast cancer, colorectal cancer, lung cancer, leukemia, prostate cancer, pancreatic cancer, head and neck cancer, and liver cancer. Preferably, the immunosensitive cancer is selected from the group Renal cell carcinoma, Melanoma (including superficial spreading SSM, nodular NM, acral lentiginous ALM, lentigo maligna LMM also called Hutchinson's Freckle), Multiple myeloma, Myeloma, Lymphoma, Non-small-cell lung cancer, bladder cancer, prostate cancer, Squamous cell carcinoma, Basal cell carcinoma, Fibrosarcoma, malignant brain tumors, Kaposi's Sarcoma, chronic myelogenous leukemia (CML) and hairy cell leukemia.

In one preferred embodiment the present invention is a method of treating an immunosensitive cancer selected from the group Renal cell carcinoma, Melanoma (including superficial spreading SSM, nodular NM, acral lentiginous ALM, lentigo maligna LMM also called Hutchinson's Freckle), Multiple myeloma, Myeloma, Lymphoma, Non-small-cell lung cancer, Squamous cell carcinoma, Basal cell carcinoma, Fibrosarcoma, malignant brain tumors, Kaposi's Sarcoma, chronic myelogenous leukemia (CML) and hairy cell leukemia, comprising administering an effective amount of a bis (thiohydrazide amide) as described herein in combination with hyperthermia or radiotherapy and further comprising administering an effective amount of a cancer vaccine.

In another preferred embodiment the present invention is a method of treating an immunosensitive cancer selected from the group Renal cell carcinoma, Melanoma (including superficial spreading SSM, nodular NM, acral lentiginous ALM, lentigo maligna LMM also called Hutchinson's Freckle), Multiple myeloma, Myeloma, Lymphoma, Non-small-cell lung cancer, Squamous cell carcinoma, Basal cell carcinoma, Fibrosarcoma, malignant brain tumors, Kaposi's Sarcoma, chronic myelogenous leukemia (CML) and hairy cell leukemia, comprising administering an effective amount of a bis (thiohydrazide amide) as described herein in combination with hyperthermia or radiotherapy and further comprising administering an effective amount of a tumor cell vaccine.

In another preferred embodiment the present invention is a method of treating an immunosensitive cancer selected from the group Renal cell carcinoma, Melanoma (including superficial spreading SSM, nodular NM, acral lentiginous ALM, lentigo maligna LMM also called Hutchinson's Freckle), Multiple myeloma, Myeloma, Lymphoma, Non-small-cell lung cancer, Squamous cell carcinoma, Basal cell carcinoma, Fibrosarcoma, malignant brain tumors, Kaposi's Sarcoma, chronic myelogenous leukemia (CML) and hairy cell leukemia, comprising administering an effective amount of a bis (thiohydrazide amide) as described herein in combination with hyperthermia or radiotherapy and further comprising administering an effective amount of a viral vaccine.

In another preferred embodiment the present invention is a method of treating an immunosensitive cancer selected from the group Renal cell carcinoma, Melanoma (including superficial spreading SSM, nodular NM, acral lentiginous ALM, lentigo maligna LMM also called Hutchinson's Freckle), Multiple myeloma, Myeloma, Lymphoma, Non-small-cell lung cancer, Squamous cell carcinoma, Basal cell carcinoma, Fibrosarcoma, malignant brain tumors, Kaposi's Sarcoma, chronic myelogenous leukemia (CML) and hairy cell leukemia, comprising administering an effective amount of a bis (thiohydrazide amide) as described herein in combination with hyperthermia or radiotherapy and further comprising administering an effective amount of an autologous tumor cell vaccine.

In another preferred embodiment the present invention is a method of treating an immunosensitive cancer selected from the group Renal cell carcinoma, Melanoma (including superficial spreading SSM, nodular NM, acral lentiginous ALM, lentigo maligna LMM also called Hutchinson's Freckle), Multiple myeloma, Myeloma, Lymphoma, Non-small-cell lung cancer, Squamous cell carcinoma, Basal cell carcinoma, Fibrosarcoma, malignant brain tumors, Kaposi's Sarcoma, chronic myelogenous leukemia (CML) and hairy cell leukemia, comprising administering an effective amount of a bis (thiohydrazide amide) as described herein in combination with hyperthermia or radiotherapy and further comprising administering an effective amount of an allogeneic tumor cell vaccine.

In another preferred embodiment the present invention is a method of treating an immunosensitive cancer selected from the group Renal cell carcinoma, Melanoma (including superficial spreading SSM, nodular NM, acral lentiginous ALM, lentigo maligna LMM also called Hutchinson's Freckle), Multiple myeloma, Myeloma, Lymphoma, Non-small-cell lung cancer, Squamous cell carcinoma, Basal cell carcinoma, Fibrosarcoma, malignant brain tumors, Kaposi's Sarcoma, chronic myelogenous leukemia (CML) and hairy cell leukemia, comprising administering an effective amount of a bis (thiohydrazide amide) as described herein in combination with hyperthermia or radiotherapy and further comprising administering an effective amount of a dendritic cell vaccine.

In another preferred embodiment the present invention is a method of treating an immunosensitive cancer selected from the group Renal cell carcinoma, Melanoma (including superficial spreading SSM, nodular NM, acral lentiginous ALM, lentigo maligna LMM also called Hutchinson's Freckle), Multiple myeloma, Myeloma, Lymphoma, Non-small-cell lung cancer, Squamous cell carcinoma, Basal cell carcinoma, Fibrosarcoma, malignant brain tumors, Kaposi's Sarcoma, chronic myelogenous leukemia (CML) and hairy cell leukemia, comprising administering an effective amount of a bis (thiohydrazide amide) as described herein in combination with hyperthermia or radiotherapy and further comprising administering an effective amount of a antigen vaccine.

In another preferred embodiment the present invention is a method of treating an immunosensitive cancer selected from the group Renal cell carcinoma, Melanoma (including superficial spreading SSM, nodular NM, acral lentiginous ALM, lentigo maligna LMM also called Hutchinson's Freckle), Multiple myeloma, Myeloma, Lymphoma, Non-small-cell lung cancer, Squamous cell carcinoma, Basal cell carcinoma, Fibrosarcoma, malignant brain tumors, Kaposi's Sarcoma, chronic myelogenous leukemia (CML) and hairy cell leukemia, comprising administering an effective amount of a bis (thiohydrazide amide) as described herein in combination with hyperthermia or radiotherapy and further comprising administering an effective amount of a anti-idiotype vaccine.

In another preferred embodiment the present invention is a method of treating an immunosensitive cancer selected from the group Renal cell carcinoma, Melanoma (including superficial spreading SSM, nodular NM, acral lentiginous ALM, lentigo maligna LMM also called Hutchinson's Freckle), Multiple myeloma, Myeloma, Lymphoma, Non-small-cell lung cancer, Squamous cell carcinoma, Basal cell carcinoma, Fibrosarcoma, malignant brain tumors, Kaposi's Sarcoma, chronic myelogenous leukemia (CML) and hairy cell leukemia, comprising administering an effective amount of a bis (thiohydrazide amide) as described herein in combination with hyperthermia or radiotherapy and further comprising administering an effective amount of a DNA vaccine.

In another preferred embodiment the present invention is a method of treating an immunosensitive cancer selected from the group Renal cell carcinoma, Melanoma (including superficial spreading SSM, nodular NM, acral lentiginous ALM, lentigo maligna LMM also called Hutchinson's Freckle), Multiple myeloma, Myeloma, Lymphoma, Non-small-cell lung cancer, Squamous cell carcinoma, Basal cell carcinoma, Fibrosarcoma, malignant brain tumors, Kaposi's Sarcoma, chronic myelogenous leukemia (CML) and hairy cell leukemia, comprising administering an effective amount of a bis (thiohydrazide amide) as described herein in combination with hyperthermia or radiotherapy and further comprising administering an effective amount of a Tumor-Infiltrating Lymphocyte (TIL) Vaccine with Interleukin-2 (IL-2).

In another preferred embodiment the present invention is a method of treating an immunosensitive cancer selected from the group Renal cell carcinoma, Melanoma (including superficial spreading SSM, nodular NM, acral lentiginous ALM, lentigo maligna LMM also called Hutchinson's Freckle), Multiple myeloma, Myeloma, Lymphoma, Non-small-cell lung cancer, Squamous cell carcinoma, Basal cell carcinoma, Fibrosarcoma, malignant brain tumors, Kaposi's Sarcoma, chronic myelogenous leukemia (CML) and hairy cell leukemia, comprising administering an effective amount of a bis (thiohydrazide amide) as described herein in combination with hyperthermia or radiotherapy and further comprising administering an effective amount of a Lymphokine-Activated Killer (LAK) Cell Therapy.

In another preferred embodiment the present invention is a method of treating an immunosensitive cancer selected from the group Renal cell carcinoma, Melanoma (including superficial spreading SSM, nodular NM, acral lentiginous ALM, lentigo maligna LMM also called Hutchinson's Freckle), Multiple myeloma, Myeloma, Lymphoma, Non-small-cell lung cancer, Squamous cell carcinoma, Basal cell carcinoma, Fibrosarcoma, malignant brain tumors, Kaposi's Sarcoma, chronic myelogenous leukemia (CML) and hairy cell leukemia, comprising administering an effective amount of a bis (thiohydrazide amide) as described herein in combination with hyperthermia or radiotherapy and further comprising administering an effective amount of Rituximab (Rituxan).

In another preferred embodiment the present invention is a method of treating an immunosensitive cancer selected from the group Renal cell carcinoma, Melanoma (including superficial spreading SSM, nodular NM, acral lentiginous ALM, lentigo maligna LMM also called Hutchinson's Freckle), Multiple myeloma, Myeloma, Lymphoma, Non-small-cell lung cancer, Squamous cell carcinoma, Basal cell carcinoma, Fibrosarcoma, malignant brain tumors, Kaposi's Sarcoma, chronic myelogenous leukemia (CML) and hairy cell leukemia, comprising administering an effective amount of a bis (thiohydrazide amide) as described herein in combination with hyperthermia or radiotherapy and further comprising administering an effective amount of Trastuzumab (Herceptin).

In another preferred embodiment the present invention is a method of treating an immunosensitive cancer selected from the group Renal cell carcinoma, Melanoma (including superficial spreading SSM, nodular NM, acral lentiginous ALM, lentigo maligna LMM also called Hutchinson's Freckle), Multiple myeloma, Myeloma, Lymphoma, Non-small-cell lung cancer, Squamous cell carcinoma, Basal cell carcinoma, Fibrosarcoma, malignant brain tumors, Kaposi's Sarcoma, chronic myelogenous leukemia (CML) and hairy cell leukemia, comprising administering an effective amount of a bis (thiohydrazide amide) as described herein in combination with hyperthermia or radiotherapy and further comprising administering an effective amount of Alemtuzumab (Campath).

In another preferred embodiment the present invention is a method of treating an immunosensitive cancer selected from the group Renal cell carcinoma, Melanoma (including superficial spreading SSM, nodular NM, acral lentiginous ALM, lentigo maligna LMM also called Hutchinson's Freckle), Multiple myeloma, Myeloma, Lymphoma, Non-small-cell lung cancer, Squamous cell carcinoma, Basal cell carcinoma, Fibrosarcoma, malignant brain tumors, Kaposi's Sarcoma, chronic myelogenous leukemia (CML) and hairy cell leukemia, comprising administering an effective amount of a bis (thiohydrazide amide) as described herein in combination with hyperthermia or radiotherapy and further comprising administering an effective amount of and Cetuximab (Erbitux).

In another preferred embodiment the present invention is a method of treating an immunosensitive cancer selected from the group Renal cell carcinoma, Melanoma (including superficial spreading SSM, nodular NM, acral lentiginous ALM, lentigo maligna LMM also called Hutchinson's Freckle), Multiple myeloma, Myeloma, Lymphoma, Non-small-cell lung cancer, Squamous cell carcinoma, Basal cell carcinoma, Fibrosarcoma, malignant brain tumors, Kaposi's Sarcoma, chronic myelogenous leukemia (CML) and hairy cell leukemia, comprising administering an effective amount of a bis (thiohydrazide amide) as described herein in combination with hyperthermia or radiotherapy and further comprising administering an effective amount of Bevacizumab (Avastin).

In another preferred embodiment the present invention is a method of treating an immunosensitive cancer selected from the group Renal cell carcinoma, Melanoma (including superficial spreading SSM, nodular NM, acral lentiginous ALM, lentigo maligna LMM also called Hutchinson's Freckle), Multiple myeloma, Myeloma, Lymphoma, Non-small-cell lung cancer, Squamous cell carcinoma, Basal cell carcinoma, Fibrosarcoma, malignant brain tumors, Kaposi's Sarcoma, chronic myelogenous leukemia (CML) and hairy cell leukemia, comprising administering an effective amount of a bis (thiohydrazide amide) as described herein in combination with hyperthermia or radiotherapy and further comprising administering an effective amount of a Radiolabeled antibody Ibritumomab tiuxetan (Zevalin).

In another preferred embodiment the present invention is a method of treating an immunosensitive cancer selected from the group Renal cell carcinoma, Melanoma (including superficial spreading SSM, nodular NM, acral lentiginous ALM, lentigo maligna LMM also called Hutchinson's Freckle), Multiple myeloma, Myeloma, Lymphoma, Non-small-cell lung cancer, Squamous cell carcinoma, Basal cell carcinoma, Fibrosarcoma, malignant brain tumors, Kaposi's Sarcoma, chronic myelogenous leukemia (CML) and hairy cell leukemia, comprising administering an effective amount of a bis (thiohydrazide amide) as described herein in combination with hyperthermia or radiotherapy and further comprising administering an effective amount of a radiolabeled antibody Tositumomab (Bexxar).

In another preferred embodiment the present invention is a method of treating an immunosensitive cancer selected from the group Renal cell carcinoma, Melanoma (including superficial spreading SSM, nodular NM, acral lentiginous ALM, lentigo maligna LMM also called Hutchinson's Freckle), Multiple myeloma, Myeloma, Lymphoma, Non-small-cell lung cancer, Squamous cell carcinoma, Basal cell carcinoma, Fibrosarcoma, malignant brain tumors, Kaposi's Sarcoma, chronic myelogenous leukemia (CML) and hairy cell leukemia, comprising administering an effective amount of a bis (thiohydrazide amide) as described herein in combination with hyperthermia or radiotherapy and further comprising administering an effective amount of a immunotoxin Gemtuzumab ozogamicin (Mylotarg).

In another preferred embodiment the present invention is a method of treating an immunosensitive cancer selected from the group Renal cell carcinoma, Melanoma (including superficial spreading SSM, nodular NM, acral lentiginous ALM, lentigo maligna LMM also called Hutchinson's Freckle), Multiple myeloma, Myeloma, Lymphoma, Non-small-cell lung cancer, Squamous cell carcinoma, Basal cell carcinoma, Fibrosarcoma, malignant brain tumors, Kaposi's Sarcoma, chronic myelogenous leukemia (CML) and hairy cell leukemia, comprising administering an effective amount of a bis (thiohydrazide amide) as described herein in combination with hyperthermia or radiotherapy and further comprising administering an effective amount of BL22.

In another preferred embodiment the present invention is a method of treating an immunosensitive cancer selected from the group Renal cell carcinoma, Melanoma (including superficial spreading SSM, nodular NM, acral lentiginous ALM, lentigo maligna LMM also called Hutchinson's Freckle), Multiple myeloma, Myeloma, Lymphoma, Non-small-cell lung cancer, Squamous cell carcinoma, Basal cell carcinoma, Fibrosarcoma, malignant brain tumors, Kaposi's Sarcoma, chronic myelogenous leukemia (CML) and hairy cell leukemia, comprising administering an effective amount of a bis (thiohydrazide amide) as described herein in combination with hyperthermia or radiotherapy and further comprising administering an effective amount of OncoScint.

In another preferred embodiment the present invention is a method of treating an immunosensitive cancer selected from the group Renal cell carcinoma, Melanoma (including superficial spreading SSM, nodular NM, acral lentiginous ALM, lentigo maligna LMM also called Hutchinson's Freckle), Multiple myeloma, Myeloma, Lymphoma, Non-small-cell lung cancer, Squamous cell carcinoma, Basal cell carcinoma, Fibrosarcoma, malignant brain tumors, Kaposi's Sarcoma, chronic myelogenous leukemia (CML) and hairy cell leukemia, comprising administering an effective amount of a bis (thiohydrazide amide) as described herein in combination with hyperthermia or radiotherapy and further comprising administering an effective amount of ProstaScint.

In another preferred embodiment the present invention is a method of treating an immunosensitive cancer selected from the group Renal cell carcinoma, Melanoma (including superficial spreading SSM, nodular NM, acral lentiginous ALM, lentigo maligna LMM also called Hutchinson's Freckle), Multiple myeloma, Myeloma, Lymphoma, Non-small-cell lung cancer, Squamous cell carcinoma, Basal cell carcinoma, Fibrosarcoma, malignant brain tumors, Kaposi's Sarcoma, chronic myelogenous leukemia (CML) and hairy cell leukemia, comprising administering an effective amount of a bis (thiohydrazide amide) as described herein in combination with hypernernia or radiotherapy and further comprising administering an effective amount of denileukin diftitox (Ontak).

In another preferred embodiment the present invention is a method of treating an immunosensitive cancer selected from the group Renal cell carcinoma, Melanoma (including superficial spreading SSM, nodular NM, acral lentiginous ALM, lentigo maligna LMM also called Hutchinson's Freckle), Multiple myeloma, Myeloma, Lymphoma, Non-small-cell lung cancer, Squamous cell carcinoma, Basal cell carcinoma, Fibrosarcoma, malignant brain tumors, Kaposi's Sarcoma, chronic myelogenous leukemia (CML) and hairy cell leukemia, comprising administering an effective amount of a bis (thiohydrazide amide) as described herein in combination with hyperthemmia or radiotherapy and further comprising administering an effective amount of a granulocyte-macrophage colony-stimulating factor (GM-CSF).

In another preferred embodiment the present invention is a method of treating an immunosensitive cancer selected from the group Renal cell carcinoma, Melanoma (including superficial spreading SSM, nodular NM, acral lentiginous ALM, lentigo maligna LMM also called Hutchinson's Freckle), Multiple myeloma, Myeloma, Lymphoma, Non-small-cell lung cancer, Squamous cell carcinoma, Basal cell carcinoma, Fibrosarcoma, malignant brain tumors, Kaposi's Sarcoma, chronic myelogenous leukemia (CML) and hairy cell leukemia, comprising administering an effective amount of a bis (thiohydrazide amide) as described herein in combination with hyperthermia or radiotherapy and further comprising administering an effective amount of granulocyte-colony stimulating factor (G-CSF).

In another preferred embodiment the present invention is a method of treating an immunosensitive cancer selected from the group Renal cell carcinoma, Melanoma (including superficial spreading SSM, nodular NM, acral lentiginous ALM, lentigo maligna LMM also called Hutchinson's Freckle), Multiple myeloma, Myeloma, Lymphoma, Non-small-cell lung cancer, Squamous cell carcinoma, Basal cell carcinoma, Fibrosarcoma, malignant brain tumors, Kaposi's Sarcoma, chronic myelogenous leukemia (CML) and hairy cell leukemia, comprising administering an effective amount of a bis (thiohydrazide amide) as described herein in combination with hyperthermia or radiotherapy and further comprising administering an effective amount of macrophage inflammatory protein (MIP)-1-alpha.

In another preferred embodiment the present invention is a method of treating an immunosensitive cancer selected from the group Renal cell carcinoma, Melanoma (including superficial spreading SSM, nodular NM, acral lentiginous ALM, lentigo maligna LMM also called Hutchinson's Freckle), Multiple myeloma, Myeloma, Lymphoma, Non-small-cell lung cancer, Squamous cell carcinoma, Basal cell carcinoma, Fibrosarcoma, malignant brain tumors, Kaposi's Sarcoma, chronic myelogenous leukemia (CML) and hairy cell leukemia, comprising administering an effective amount of a bis (thiohydrazide amide) as described herein in combination with hyperthermia or radiotherapy and further comprising administering an effective amount of an interleukin.

In another preferred embodiment the present invention is a method of treating an immunosensitive cancer selected from the group Renal cell carcinoma, Melanoma (including superficial spreading SSM, nodular NM, acral lentiginous ALM, lentigo maligna LMM also called Hutchinson's Freckle), Multiple myeloma, Myeloma, Lymphoma, Non-small-cell lung cancer, Squamous cell carcinoma, Basal cell carcinoma, Fibrosarcoma, malignant brain tumors, Kaposi's Sarcoma, chronic myelogenous leukemia (CML) and hairy cell leukemia, comprising administering an effective amount of a bis (thiohydrazide amide) as described herein in combination with hyperthermia or radiotherapy and further comprising administering an effective amount of IL-1.

In another preferred embodiment the present invention is a method of treating an immunosensitive cancer selected from the group Renal cell carcinoma, Melanoma (including superficial spreading SSM, nodular NM, acral lentiginous ALM, lentigo maligna LMM also called Hutchinson's Freckle), Multiple myeloma, Myeloma, Lymphoma, Non-small-cell lung cancer, Squamous cell carcinoma, Basal cell carcinoma, Fibrosarcoma, malignant brain tumors, Kaposi's Sarcoma, chronic myelogenous leukemia (CML) and hairy cell leukemia, comprising administering an effective amount of a bis (thiohydrazide amide) as described herein in combination with hyperthermia or radiotherapy and further comprising administering an effective amount of IL-2.

In another preferred embodiment the present invention is a method of treating an immunosensitive cancer selected from the group Renal cell carcinoma, Melanoma (including superficial spreading SSM, nodular NM, acral lentiginous ALM, lentigo maligna LMM also called Hutchinson's Freckle), Multiple myeloma, Myeloma, Lymphoma, Non-small-cell lung cancer, Squamous cell carcinoma, Basal cell carcinoma, Fibrosarcoma, malignant brain tumors, Kaposi's Sarcoma, chronic myelogenous leukemia (CML) and hairy cell leukemia, comprising administering an effective amount of a bis (thiohydrazide amide) as described herein in combination with hyperthermia or radiotherapy and further comprising administering an effective amount of IL-4.

In another preferred embodiment the present invention is a method of treating an immunosensitive cancer selected from the group Renal cell carcinoma, Melanoma (including superficial spreading SSM, nodular NM, acral lentiginous ALM, lentigo maligna LMM also called Hutchinson's Freckle), Multiple myeloma, Myeloma, Lymphoma, Non-small-cell lung cancer, Squamous cell carcinoma, Basal cell carcinoma, Fibrosarcoma, malignant brain tumors, Kaposi's Sarcoma, chronic myelogenous leukemia (CML) and hairy cell leukemia, comprising administering an effective amount of a bis (thiohydrazide amide) as described herein in combination with hyperthemmia or radiotherapy and further comprising administering an effective amount of IL-6.

In another preferred embodiment the present invention is a method of treating an immunosensitive cancer selected from the group Renal cell carcinoma, Melanoma (including superficial spreading SSM, nodular NM, acral lentiginous ALM, lentigo maligna LMM also called Hutchinson's Freckle), Multiple myeloma, Myeloma, Lymphoma, Non-small-cell lung cancer, Squamous cell carcinoma, Basal cell carcinoma, Fibrosarcoma, malignant brain tumors, Kaposi's Sarcoma, chronic myelogenous leukemia (CML) and hairy cell leukemia, comprising administering an effective amount of a bis (thiohydrazide amide) as described herein in combination with hyperthermia or radiotherapy and further comprising administering an effective amount of IL-7.

In another preferred embodiment the present invention is a method of treating an immunosensitive cancer selected from the group Renal cell carcinoma, Melanoma (including superficial spreading SSM, nodular NM, acral lentiginous ALM, lentigo maligna LMM also called Hutchinson's Freckle), Multiple myeloma, Myeloma, Lymphoma, Non-small-cell lung cancer, Squamous cell carcinoma, Basal cell carcinoma, Fibrosarcoma, malignant brain tumors, Kaposi's Sarcoma, chronic myelogenous leukemia (CML) and hairy cell leukemia, comprising administering an effective amount of a bis (thiohydrazide amide) as described herein in combination with hyperthermia or radiotherapy and further comprising administering an effective amount of IL-12.

In another preferred embodiment the present invention is a method of treating an immunosensitive cancer selected from the group Renal cell carcinoma, Melanoma (including superficial spreading SSM, nodular NM, acral lentiginous ALM, lentigo maligna LMM also called Hutchinson's Freckle), Multiple myeloma, Myeloma, Lymphoma, Non-small-cell lung cancer, Squamous cell carcinoma, Basal cell carcinoma, Fibrosarcoma, malignant brain tumors, Kaposi's Sarcoma, chronic myelogenous leukemia (CML) and hairy cell leukemia, comprising administering an effective amount of a bis (thiohydrazide amide) as described herein in combination with hyperthermia or radiotherapy and further comprising administering an effective amount of IL-15.

In another preferred embodiment the present invention is a method of treating an immunosensitive cancer selected from the group Renal cell carcinoma, Melanoma (including superficial spreading SSM, nodular NM, acral lentiginous ALM, lentigo maligna LMM also called Hutchinson's Freckle), Multiple myeloma, Myeloma, Lymphoma, Non-small-cell lung cancer, Squamous cell carcinoma, Basal cell carcinoma, Fibrosarcoma, malignant brain tumors, Kaposi's Sarcoma, chronic myelogenous leukemia (CML) and hairy cell leukemia, comprising administering an effective amount of a bis (thiohydrazide amide) as described herein in combination with hyperthermia or radiotherapy and further comprising administering an effective amount of IL-18.

In another preferred embodiment the present invention is a method of treating an immunosensitive cancer selected from the group Renal cell carcinoma, Melanoma (including superficial spreading SSM, nodular NM, acral lentiginous ALM, lentigo maligna LMM also called Hutchinson's Freckle), Multiple myeloma, Myeloma, Lymphoma, Non-small-cell lung cancer, Squamous cell carcinoma, Basal cell carcinoma, Fibrosarcoma, malignant brain tumors, Kaposi's Sarcoma, chronic myelogenous leukemia (CML) and hairy cell leukemia, comprising administering an effective amount of a bis (thiohydrazide amide) as described herein in combination with hyperthermia or radiotherapy and further comprising administering an effective amount of IL-21.

In another preferred embodiment the present invention is a method of treating an immunosensitive cancer selected from the group Renal cell carcinoma, Melanoma (including superficial spreading SSM, nodular NM, acral lentiginous ALM, lentigo maligna LMM also called Hutchinson's Freckle), Multiple myeloma, Myeloma, Lymphoma, Non-small-cell lung cancer, Squamous cell carcinoma, Basal cell carcinoma, Fibrosarcoma, malignant brain tumors, Kaposi's Sarcoma, chronic myelogenous leukemia (CML) and hairy cell leukemia, comprising administering an effective amount of a bis (thiohydrazide amide) as described herein in combination with hyperthermia or radiotherapy and further comprising administering an effective amount of IL-27.

In another preferred embodiment the present invention is a method of treating an immunosensitive cancer selected from the group Renal cell carcinoma, Melanoma (including superficial spreading SSM, nodular NM, acral lentiginous ALM, lentigo maligna LMM also called Hutchinson's Freckle), Multiple myeloma, Myeloma, Lymphoma, Non-small-cell lung cancer, Squamous cell carcinoma, Basal cell carcinoma, Fibrosarcoma, malignant brain tumors, Kaposi's Sarcoma, chronic myelogenous leukemia (CML) and hairy cell leukemia, comprising administering an effective amount of a bis (thiohydrazide amide) as described herein in combination with hyperthermia or radiotherapy and further comprising administering an effective amount of a tumor necrosis factors.

In another preferred embodiment the present invention is a method of treating an immunosensitive cancer selected from the group Renal cell carcinoma, Melanoma (including superficial spreading SSM, nodular NM, acral lentiginous ALM, lentigo maligna LMM also called Hutchinson's Freckle), Multiple myeloma, Myeloma, Lymphoma, Non-small-cell lung cancer, Squamous cell carcinoma, Basal cell carcinoma, Fibrosarcoma, malignant brain tumors, Kaposi's Sarcoma, chronic myelogenous leukemia (CML) and hairy cell leukemia, comprising administering an effective amount of a bis (thiohydrazide amide) as described herein in combination with hyperthermia or radiotherapy and further comprising administering an effective amount of TNF-alpha.

In another preferred embodiment the present invention is a method of treating an immunosensitive cancer selected from the group Renal cell carcinoma, Melanoma (including superficial spreading SSM, nodular NM, acral lentiginous ALM, lentigo maligna LMM also called Hutchinson's Freckle), Multiple myeloma, Myeloma, Lymphoma, Non-small-cell lung cancer, Squamous cell carcinoma, Basal cell carcinoma, Fibrosarcoma, malignant brain tumors, Kaposi's Sarcoma, chronic myelogenous leukemia (CML) and hairy cell leukemia, comprising administering an effective amount of a bis (thiohydrazide amide) as described herein in combination with hyperthermia or radiotherapy and further comprising administering an effective amount of an interferon.

In another preferred embodiment the present invention is a method of treating an immunosensitive cancer selected from the group Renal cell carcinoma, Melanoma (including superficial spreading SSM, nodular NM, acral lentiginous ALM, lentigo maligna LMM also called Hutchinson's Freckle), Multiple myeloma, Myeloma, Lymphoma, Non-small-cell lung cancer, Squamous cell carcinoma, Basal cell carcinoma, Fibrosarcoma, malignant brain tumors, Kaposi's Sarcoma, chronic myelogenous leukemia (CML) and hairy cell leukemia, comprising administering an effective amount of a bis (thiohydrazide amide) as described herein in combination with hyperthermia or radiotherapy and further comprising administering an effective amount of IFN-alpha.

In another preferred embodiment the present invention is a method of treating an immunosensitive cancer selected from the group Renal cell carcinoma, Melanoma (including superficial spreading SSM, nodular NM, acral lentiginous ALM, lentigo maligna LMM also called Hutchinson's Freckle), Multiple myeloma, Myeloma, Lymphoma, Non-small-cell lung cancer, Squamous cell carcinoma, Basal cell carcinoma, Fibrosarcoma, malignant brain tumors, Kaposi's Sarcoma, chronic myelogenous leukemia (CML) and hairy cell leukemia, comprising administering an effective amount of a bis (thiohydrazide amide) as described herein in combination with hyperthermia or radiotherapy and further comprising administering an effective amount of IFN-beta.

In another preferred embodiment the present invention is a method of treating an immunosensitive cancer selected from the group Renal cell carcinoma, Melanoma (including superficial spreading SSM, nodular NM, acral lentiginous ALM, lentigo maligna LMM also called Hutchinson's Freckle), Multiple myeloma, Myeloma, Lymphoma, Non-small-cell lung cancer, Squamous cell carcinoma, Basal cell carcinoma, Fibrosarcoma, malignant brain tumors, Kaposi's Sarcoma, chronic myelogenous leukemia (CML) and hairy cell leukemia, comprising administering an effective amount of a bis (thiohydrazide amide) as described herein in combination with hyperthermia or radiotherapy and further comprising administering an effective amount of IFN-gamma.

In another preferred embodiment the present invention is a method of treating an immunosensitive cancer selected from the group Renal cell carcinoma, Melanoma (including superficial spreading SSM, nodular NM, acral lentiginous ALM, lentigo maligna LMM also called Hutchinson's Freckle), Multiple myeloma, Myeloma, Lymphoma, Non-small-cell lung cancer, Squamous cell carcinoma, Basal cell carcinoma, Fibrosarcoma, malignant brain tumors, Kaposi's Sarcoma, chronic myelogenous leukemia (CML) and hairy cell leukemia, comprising administering an effective amount of a bis (thiohydrazide amide) as described herein in combination with hyperthermia or radiotherapy and further comprising administering an effective amount of aluminum hydroxide (alum).

In another preferred embodiment the present invention is a method of treating an immunosensitive cancer selected from the group Renal cell carcinoma, Melanoma (including superficial spreading SSM, nodular NM, acral lentiginous ALM, lentigo maligna LMM also called Hutchinson's Freckle), Multiple myeloma, Myeloma, Lymphoma, Non-small-cell lung cancer, Squamous cell carcinoma, Basal cell carcinoma, Fibrosarcoma, malignant brain tumors, Kaposi's Sarcoma, chronic myelogenous leukemia (CML) and hairy cell leukemia, comprising administering an effective amount of a bis (thiohydrazide amide) as described herein in combination with hyperthermia or radiotherapy and further comprising administering an effective amount of Bacille Calmette-Guérin (BCG).

In another preferred embodiment the present invention is a method of treating an immunosensitive cancer selected from the group Renal cell carcinoma, Melanoma (including superficial spreading SSM, nodular NM, acral lentiginous ALM, lentigo maligna LMM also called Hutchinson's Freckle), Multiple myeloma, Myeloma, Lymphoma, Non-small-cell lung cancer, Squamous cell carcinoma, Basal cell carcinoma, Fibrosarcoma, malignant brain tumors, Kaposi's Sarcoma, chronic myelogenous leukemia (CML) and hairy cell leukemia, comprising administering an effective amount of a bis (thiohydrazide amide) as described herein in combination with hyperthermia or radiotherapy and further comprising administering an effective amount of Keyhole limpet hemocyanin (KLH).

In another preferred embodiment the present invention is a method of treating an immunosensitive cancer selected from the group Renal cell carcinoma, Melanoma (including superficial spreading SSM, nodular NM, acral lentiginous ALM, lentigo maligna LMM also called Hutchinson's Freckle), Multiple myeloma, Myeloma, Lymphoma, Non-small-cell lung cancer, Squamous cell carcinoma, Basal cell carcinoma, Fibrosarcoma, malignant brain tumors, Kaposi's Sarcoma, chronic myelogenous leukemia (CML) and hairy cell leukemia, comprising administering an effective amount of a bis (thiohydrazide amide) as described herein in combination with hyperthermia or radiotherapy and further comprising administering an effective amount of Incomplete Freund's adjuvant (IFA).

In another preferred embodiment the present invention is a method of treating an immunosensitive cancer selected from the group Renal cell carcinoma, Melanoma (including superficial spreading SSM, nodular NM, acral lentiginous ALM, lentigo maligna LMM also called Hutchinson's Freckle), Multiple myeloma, Myeloma, Lymphoma, Non-small-cell lung cancer, Squamous cell carcinoma, Basal cell carcinoma, Fibrosarcoma, malignant brain tumors, Kaposi's Sarcoma, chronic myelogenous leukemia (CML) and hairy cell leukemia, comprising administering an effective amount of a bis (thiohydrazide amide) as described herein in combination with hyperthermia or radiotherapy and further comprising administering an effective amount of QS-21.

In another preferred embodiment the present invention is a method of treating an immunosensitive cancer selected from the group Renal cell carcinoma, Melanoma (including superficial spreading SSM, nodular NM, acral lentiginous ALM, lentigo maligna LMM also called Hutchinson's Freckle), Multiple myeloma, Myeloma, Lymphoma, Non-small-cell lung cancer, Squamous cell carcinoma, Basal cell carcinoma, Fibrosarcoma, malignant brain tumors, Kaposi's Sarcoma, chronic myelogenous leukemia (CML) and hairy cell leukemia, comprising administering an effective amount of a bis (thiohydrazide amide) as described herein in combination with hyperthermia or radiotherapy and further comprising administering an effective amount of DETOX.

In another preferred embodiment the present invention is a method of treating an immunosensitive cancer selected from the group Renal cell carcinoma, Melanoma (including superficial spreading SSM, nodular NM, acral lentiginous ALM, lentigo maligna LMM also called Hutchinson's Freckle), Multiple myeloma, Myeloma, Lymphoma, Non-small-cell lung cancer, Squamous cell carcinoma, Basal cell carcinoma, Fibrosarcoma, malignant brain tumors, Kaposi's Sarcoma, chronic myelogenous leukemia (CML) and hairy cell leukemia, comprising administering an effective amount of a bis (thiohydrazide amide) as described herein in combination with hyperthermia or radiotherapy and further comprising administering an effective amount of Levamisole.

In another preferred embodiment the present invention is a method of treating an immunosensitive cancer selected from the group Renal cell carcinoma, Melanoma (including superficial spreading SSM, nodular NM, acral lentiginous ALM, lentigo maligna LMM also called Hutchinson's Freckle), Multiple myeloma, Myeloma, Lymphoma, Non-small-cell lung cancer, Squamous cell carcinoma, Basal cell carcinoma, Fibrosarcoma, malignant brain tumors, Kaposi's Sarcoma, chronic myelogenous leukemia (CML) and hairy cell leukemia, comprising administering an effective amount of a bis (thiohydrazide amide) as described herein in combination with hyperthermia or radiotherapy and further comprising administering an effective amount of Dinitrophenyl (DNP).

In another preferred embodiment the present invention is a method of treating an immunosensitive cancer selected from the group Renal cell carcinoma, Melanoma (including superficial spreading SSM, nodular NM, acral lentiginous ALM, lentigo maligna LMM also called Hutchinson's Freckle), Multiple myeloma, Myeloma, Lymphoma, Non-small-cell lung cancer, Squamous cell carcinoma, Basal cell carcinoma, Fibrosarcoma, malignant brain tumors, Kaposi's Sarcoma, chronic myelogenous leukemia (CML) and hairy cell leukemia, comprising administering an effective amount of a bis (thiohydrazide amide) as described herein in combination with hyperthermia or radiotherapy and further comprising administering an effective amount of a tumor-infiltrating lymphocyte.

In another preferred embodiment the present invention is a method of treating an immunosensitive cancer selected from the group Renal cell carcinoma, Melanoma (including superficial spreading SSM, nodular NM, acral lentiginous ALM, lentigo maligna LMM also called Hutchinson's Freckle), Multiple myeloma, Myeloma, Lymphoma, Non-small-cell lung cancer, Squamous cell carcinoma, Basal cell carcinoma, Fibrosarcoma, malignant brain tumors, Kaposi's Sarcoma, chronic myelogenous leukemia (CML) and hairy cell leukemia, comprising administering an effective amount of a bis (thiohydrazide amide) as described herein in combination with hyperthermia or radiotherapy and further comprising administering an effective amount of a human monoclonal antibody to ganglioside antigens.

In another preferred embodiment the present invention is a method of treating an immunosensitive cancer selected from the group Renal cell carcinoma, Melanoma (including superficial spreading SSM, nodular NM, acral lentiginous ALM, lentigo maligna LMM also called Hutchinson's Freckle), Multiple myeloma, Myeloma, Lymphoma, Non-small-cell lung cancer, Squamous cell carcinoma, Basal cell carcinoma, Fibrosarcoma, malignant brain tumors, Kaposi's Sarcoma, chronic myelogenous leukemia (CML) and hairy cell leukemia, comprising administering an effective amount of a bis (thiohydrazide amide) as described herein in combination with hyperthermia or radiotherapy and further comprising administering an effective amount of a polyvalent antigen vaccine.

In another preferred embodiment the present invention is a method of treating an immunosensitive cancer selected from the group Renal cell carcinoma, Melanoma (including superficial spreading SSM, nodular NM, acral lentiginous ALM, lentigo maligna LMM also called Hutchinson's Freckle), Multiple myeloma, Myeloma, Lymphoma, Non-small-cell lung cancer, Squamous cell carcinoma, Basal cell carcinoma, Fibrosarcoma, malignant brain tumors, Kaposi's Sarcoma, chronic myelogenous leukemia (CML) and hairy cell leukemia, comprising administering an effective amount of a bis (thiohydrazide amide) as described herein in combination with hyperthermia or radiotherapy and further comprising administering an effective amount of a combination of IL-2 with IFN-alpha.

In another preferred embodiment the present invention is a method of treating an immunosensitive cancer selected from the group Renal cell carcinoma, Melanoma (including superficial spreading SSM, nodular NM, acral lentiginous ALM, lentigo maligna LMM also called Hutchinson's Freckle), Multiple myeloma, Myeloma, Lymphoma, Non-small-cell lung cancer, Squamous cell carcinoma, Basal cell carcinoma, Fibrosarcoma, malignant brain tumors, Kaposi's Sarcoma, chronic myelogenous leukemia (CML) and hairy cell leukemia, comprising administering an effective amount of a bis (thiohydrazide amide) as described herein in combination with hyperthermia or radiotherapy and further comprising administering an effective amount of a combination of an interleukin with a cytokine.

In another preferred embodiment the present invention is a method of treating an immunosensitive cancer selected from the group Renal cell carcinoma, Melanoma (including superficial spreading SSM, nodular NM, acral lentiginous ALM, lentigo maligna LMM also called Hutchinson's Freckle), Multiple myeloma, Myeloma, Lymphoma, Non-small-cell lung cancer, Squamous cell carcinoma, Basal cell carcinoma, Fibrosarcoma, malignant brain tumors, Kaposi's Sarcoma, chronic myelogenous leukemia (CML) and hairy cell leukemia, comprising administering an effective amount of a bis (thiohydrazide amide) as described herein in combination with hyperthermia or radiotherapy and further comprising administering an effective amount of combination of IL-12 and TNF-alpha.

In another preferred embodiment the present invention is a method of treating an immunosensitive cancer selected from the group Renal cell carcinoma, Melanoma (including superficial spreading SSM, nodular NM, acral lentiginous ALM, lentigo maligna LMM also called Hutchinson's Freckle), Multiple myeloma, Myeloma, Lymphoma, Non-small-cell lung cancer, Squamous cell carcinoma, Basal cell carcinoma, Fibrosarcoma, malignant brain tumors, Kaposi's Sarcoma, chronic myelogenous leukemia (CML) and hairy cell leukemia, comprising administering an effective amount of a bis (thiohydrazide amide) as described herein in combination with hyperthermia or radiotherapy and further comprising administering an effective amount of a combination of BCG with a melanoma vaccine and optionally another immunotherapy as described herein.

In another preferred embodiment the present invention is a method of treating an immunosensitive cancer selected from the group Renal cell carcinoma, Melanoma (including superficial spreading SSM, nodular NM, acral lentiginous ALM, lentigo maligna LMM also called Hutchinson's Freckle), Multiple myeloma, Myeloma, Lymphoma, Non-small-cell lung cancer, Squamous cell carcinoma, Basal cell carcinoma, Fibrosarcoma, malignant brain tumors, Kaposi's Sarcoma, chronic myelogenous leukemia (CML) and hairy cell leukemia, comprising administering an effective amount of a bis (thiohydrazide amide) as described herein in combination with hyperthermia or radiotherapy and further comprising administering an effective amount of a combination of IL-2, interferon and an anti-cancer agent as described herein.

In another preferred embodiment the present invention is a method of treating an immunosensitive cancer selected from the group Renal cell carcinoma, Melanoma (including superficial spreading SSM, nodular NM, acral lentiginous ALM, lentigo maligna LMM also called Hutchinson's Freckle), Multiple myeloma, Myeloma, Lymphoma, Non-small-cell lung cancer, Squamous cell carcinoma, Basal cell carcinoma, Fibrosarcoma, malignant brain tumors, Kaposi's Sarcoma, chronic myelogenous leukemia (CML) and hairy cell leukemia, comprising administering an effective amount of a bis (thiohydrazide amide) as described herein in combination with hyperthermia or radiotherapy and further comprising administering an effective amount of a combination of a tumor cell vaccine with BCG.

In another preferred embodiment the present invention is a method of treating an immunosensitive cancer selected from the group Renal cell carcinoma, Melanoma (including superficial spreading SSM, nodular NM, acral lentiginous ALM, lentigo maligna LMM also called Hutchinson's Freckle), Multiple myeloma, Myeloma, Lymphoma, Non-small-cell lung cancer, Squamous cell carcinoma, Basal cell carcinoma, Fibrosarcoma, malignant brain tumors, Kaposi's Sarcoma, chronic myelogenous leukemia (CML) and hairy cell leukemia, comprising administering an effective amount of a bis (thiohydrazide amide) as described herein in combination with hyperthernia or radiotherapy and further comprising administering an effective amount of a combination of a DNA vaccine and tumor-infiltrating lymphocytes.

In another preferred embodiment the present invention is a method of treating an immunosensitive cancer selected from the group Renal cell carcinoma, Melanoma (including superficial spreading SSM, nodular NM, acral lentiginous ALM, lentigo maligna LMM also called Hutchinson's Freckle), Multiple myeloma, Myeloma, Lymphoma, Non-small-cell lung cancer, Squamous cell carcinoma, Basal cell carcinoma, Fibrosarcoma, malignant brain tumors, Kaposi's Sarcoma, chronic myelogenous leukemia (CML) and hairy cell leukemia, comprising administering an effective amount of a bis (thiohydrazide amide) as described herein in combination with hyperthermia or radiotherapy and further comprising administering an effective amount of a combination of a chimeric bispecific G250/anti-CD3 monoclonal antibody.

In all of the above preceding paragraphs of preferred embodiments taxol or taxotere are also optionally administered.

In one embodiment of the present invention the bis(thiohydrazide amides) described herein and the other anticancer therapies described herein can be administered to a subject in the form of a pharmaceutical composition.

As used herein, a "pharmaceutical composition" can be a formulation containing the disclosed compounds, in a form suitable for administration to a subject. The pharmaceutical composition can be in bulk or in unit dosage form. The unit dosage form can be in any of a variety of forms, including, for example, a capsule, an IV bag, a tablet, a single pump on an aerosol inhaler, or a vial. The quantity of active ingredient (i.e., a formulation of the disclosed compound or salts thereof) in a unit dose of composition can be an effective amount and can be varied according to the particular treatment involved. It may be appreciated that it can be necessary to make routine variations to the dosage depending on the age and condition of the patient. The dosage can also depend on the route of administration. Examples of suitable dosages are those described in PCT/US2006/014531 filed 13 Apr. 2006, titled Combination Cancer Therapy With Bis[Thiohydrazide]

Amide Compounds, the entire contents of which are incorporated herein by reference. A variety of routes are contemplated, including topical, oral, pulmonary, rectal, vaginal, parenternal, including transdermal, subcutaneous, intravenous, intramuscular, intraperitoneal and intranasal.

The compounds described herein, and the pharmaceutically acceptable salts thereof can be used in pharmaceutical preparations in combination with a pharmaceutically acceptable carrier or diluent. Suitable pharmaceutically acceptable carriers include inert solid fillers or diluents and sterile aqueous or organic solutions. The compounds can be present in such pharmaceutical compositions in amounts sufficient to provide the desired dosage amount in the range described herein. Techniques for formulation and administration of the disclosed compounds of the invention can be found in *Remington: the Science and Practice of Pharmacy*, 19$^{th}$ edition, Mack Publishing Co., Easton, Pa. (1995). The bis(thio-hydrazide amide) disclosed herein can be prepared by the methods described in U.S. Provisional Patent No. 60/708,977 filed 16 Aug. 2005, titled Bis(Thio-Hydrazide Amide) Formulation, the entire teachings of which is incorporated herein by reference.

In one embodiment the bis(thio hydrazide amide) described herein is added to a solution of Taxol in Cremophor®. In one embodiment, Taxol is 6 mg/mL and the bis (thiohydrazid amide) (e.g., compound (I) is 16 mg/L in the Cremophor® solution. Optionally, the solution is then diluted with a saline solution. Specifically, for Intravenous Administration: Taxol is diluted prior to infusion, for example, Taxol is diluted in 0.9% Sodium Chloride Injection, USP; 5% Dextrose Injection, USP; 5% Dextrose and 0.9% Sodium Chloride Injection, USP, or 5% Dextrose in Ringer's Injection to a final concentration of 0.3 to 1.2 mg/mL.

For oral administration, the disclosed compounds or salts thereof can be combined with a suitable solid or liquid carrier or diluent to form capsules, tablets, pills, powders, syrups, solutions, suspensions, or the like.

The tablets, pills, capsules, and the like can contain from about 1 to about 99 weight percent of the active ingredient and a binder such as gum tragacanth, acacias, corn starch or gelatin; excipients such as dicalcium phosphate; a disintegrating agent such as corn starch, potato starch or alginic acid; a lubricant such as magnesium stearate; and/or a sweetening agent such as sucrose, lactose or saccharin. When a dosage unit form is a capsule, it may contain, in addition to materials of the above type, a liquid carrier such as a fatty oil.

Various other materials can be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor, and the like.

For parental administration, the bis(thio-hydrazide) amides can be combined with sterile aqueous or organic media to form injectable solutions or suspensions. For example, solutions in sesame or peanut oil, aqueous propylene glycol and the like can be used, as well as aqueous solutions of water-soluble pharmaceutically-acceptable salts of the compounds. Dispersions can also be prepared in glycerol, liquid polyethylene glycols and mixtures thereof in oils. Under ordinary conditions of storage and use, these preparations contain a preservative to prevent the growth of microorganisms.

In addition to the formulations previously described, the compounds may also be formulated as a depot preparation. Suitable formulations of this type include biocompatible and biodegradable polymeric hydrogel formulations using crosslinked or water insoluble polysaccharide formulations, polymerizable polyethylene oxide formulations, impregnated membranes, and the like. Such long acting formulations may be administered by implantation or transcutaneous delivery (for example subcutaneously or intramuscularly), intramuscular injection or a transdermal patch. Typically, they can be implanted in, or applied to, the microenvironment of an affected organ or tissue, for example, a membrane impregnated with the disclosed compound can be applied to an open wound or burn injury. Thus, for example, the compounds may be formulated with suitable polymeric or hydrophobic materials, for example, as an emulsion in an acceptable oil, or ion exchange resins, or as sparingly soluble derivatives, for example, as a sparingly soluble salt.

For topical administration, suitable formulations may include biocompatible oil, wax, gel, powder, polymer, or other liquid or solid carriers. Such formulations may be administered by applying directly to affected tissues, for example, a liquid formulation to treat infection of conjuntival tissue can be administered dropwise to the subject's eye, a cream formulation can be administer to a wound site, or a bandage may be impregnated with a formulation, and the like.

For rectal administration, suitable pharmaceutical compositions are, for example, topical preparations, suppositories or enemas.

For vaginal administration, suitable pharmaceutical compositions are, for example, topical preparations, pessaries, tampons, creams, gels, pastes, foams or sprays.

In addition, the compounds may also be formulated to deliver the active agent by pulmonary administration, e.g., administration of an aerosol formulation containing the active agent from, for example, a manual pump spray, nebulizer or pressurized metered-dose inhaler. Suitable formulations of this type can also include other agents, such as antistatic agents, to maintain the disclosed compounds as effective aerosols.

The term "pulmonary" as used herein refers to any part, tissue or organ whose primary function is gas exchange with the external environment, i.e., $O_2/CO_2$ exchange, within a patient. "Pulmonary" typically refers to the tissues of the respiratory tract. Thus, the phrase "pulmonary administration" refers to administering the formulations described herein to any part, tissue or organ whose primary function is gas exchange with the external environment (e.g., mouth, nose, pharynx, oropharynx, laryngopharynx, larynx, trachea, carina, bronchi, bronchioles, alveoli). For purposes of the present invention, "pulmonary" is also meant to include a tissue or cavity that is contingent to the respiratory tract, in particular, the sinuses.

A drug delivery device for delivering aerosols can comprise a suitable aerosol canister with a metering valve containing a pharmaceutical aerosol formulation as described and an actuator housing adapted to hold the canister and allow for drug delivery. The canister in the drug delivery device has a head space representing greater than about 15% of the total volume of the canister. Often, the polymer intended for pulmonary administration is dissolved, suspended or emulsified in a mixture of a solvent, surfactant and propellant. The mixture is maintained under pressure in a canister that has been sealed with a metering valve.

For nasal administration, either a solid or a liquid carrier can be used. The solid carrier includes a coarse powder having particle size in the range of, for example, from about 20 to about 500 microns and such formulation is administered by rapid inhalation through the nasal passages. Where the liquid carrier is used, the formulation may be administered as a nasal spray or drops and may include oil or aqueous solutions of the active ingredients.

In addition to the formulations described above, a formulation can optionally include, or be co-administered with one or more additional drugs. The formulation may also contain preserving agents, solubilizing agents, chemical buffers, surfactants, emulsifiers, colorants, odorants and sweeteners.

A "subject" is a mammal, preferably a human, but can also be an animal in need of veterinary treatment, e.g., companion animals (e.g., dogs, cats, and the like), farm animals (e.g., cows, sheep, pigs, horses, and the like) and laboratory animals (e.g., rats, mice, guinea pigs, and the like).

As noted above, one embodiment of the present invention is directed to treating subjects with an immunosensitive cancer. "Treating a subject with an immunosensitive cancer" includes achieving, partially or substantially, one or more of the following results: arresting the growth or spread of a cancer, reducing the extent of a cancer (e.g., reducing size of a tumor or reducing the number of affected sites), inhibiting the growth rate of a cancer, and ameliorating or improving a clinical symptom or indicator associated with a cancer. "Treating a subject with an immunosensitive cancer" also includes partially or totally inhibiting, delaying or preventing the progression of cancer including cancer metastasis; partially or totally inhibiting, delaying or preventing the recurrence of cancer including cancer metastasis (in a subject who has been treated for cancer); or partially or totally preventing the onset or development of cancer (chemoprevention). Partially or totally inhibiting, delaying or preventing the recurrence of means inhibiting, delaying or preventing the recurrence of the cancer, after the original tumor has been removed, for example, by surgery. A subject who has been "treated for an immunosensitive cancer", is a subject in which, for example, the primary tumor has been, for example, removed surgically or has gone into remission following treatment by, for example, chemotherapy.

The term "effective amount" is the quantity of compound in which a beneficial clinical outcome is achieved when the compound is administered to a subject with a cancer. A "beneficial clinical outcome" includes prevention, inhibition or a delay in the recurrence of cancer, a reduction in tumor mass, a reduction in metastasis, a reduction in the severity of the symptoms associated with the cancer and/or an increase in the longevity of the subject compared with the absence of the treatment. The precise amount of immunotherapy, compound or other anti-cancer agent administered to a subject will depend on the type and severity of the disease or condition and on the characteristics of the subject, such as general health, age, sex, body weight and tolerance to drugs. It will also depend on the degree, severity and type of cancer. The skilled artisan will be able to determine appropriate dosages depending on these and other factors. Effective amounts of the disclosed bis(thiohydrazide amides) typically range between about 1 mg/mm$^2$ per day and about 10 grams/mm$^2$ per day, and preferably between 10 mg/mm$^2$ per day and about 5 grams/mm$^2$. When co-administered with an immunotherapy or another anti-cancer agent, an "effective amount" of the immunotherapy or anti-cancer agent will depend on the type of drug used. Suitable dosages are known for approved anti-cancer agents and approved immunotherapies and can be adjusted by the skilled artisan according to the condition of the subject, the type of cancer being treated and the amount of bis(thio-hydrazide amide) disalt being used.

Examples of specific dosage regimens for the disclosed compounds used in combination with taxanes are provided below. When combined with an immunotherapy, it is understood that an effective amount of the immunotherapy is also used One dosage regimen includes the step of co-administering to the subject over three to five weeks, a taxane in an amount of between about 243 µmol/m2 to 315 µmol/m2 (e.g., equivalent to paclitaxel in about 210-270 mg/m2); and a bis(thiohydrazide amide) (e.g., as represented by Structural Formula I) in an amount between about 1473 µmol/m2 and about 1722 µmol/m2 (e.g., Compound (1) in about 590-690 mg/m2).

In another dosage regimen the taxane and the bis(thiohydrazide) amide can each be administered in three equal weekly doses for three weeks of a four week period. In preferred embodiments, the four week administration period can be repeated until the cancer is in remission. The taxane can be any taxane defined herein. In a specific embodiment, the taxane is paclitaxel intravenously administered in a weekly dose of about 94 µmol/m2 (80 mg/m2). Typically, the bis (thiohydrazide amide) can be intravenously administered in a weekly dose of between about 500 µmol/m2 and about 562 µmol/m2, or more typically in a weekly dose of about 532 µmol/m2. (e.g., Compound (1) in about 590-690 mg/m2).

Another dosage regimen includes intravenously administering to the subject in a four week period, three equal weekly doses of paclitaxel in an amount of about 94 µmol/m2; and compound (I) or a pharmaceutically acceptable salt or solvate thereof in an amount of about 532 µmol/m2.

In another dosage regimen, the subject can be intravenously administered between about 220 µmol/m2 and about 1310 µmol/m2 (e.g., Compound (1) in about 88-525 mg/m2) of the bis(thiohydrazide amide) once every 3 weeks, generally between about 220 µmol/m2 and about 1093 µmol/m2 (e.g., Compound (1) in about 88-438 mg/m2) once every 3 weeks, typically between about 624 µmol/m2 and about 1124 µmol/m2 m2 (e.g., Compound (1) in about 250-450 mg/m2), more typically between about 811 µmol/m2 and about 936 µmol/m2 m2 (e.g., Compound (1) in about 325-375 mg/m2), or in particular embodiments, about 874 µmol/m2 ((e.g., Compound (1) in about 350 mg/m2). In particular embodiments, the subject can be intravenously administered between about 582 µmol/m2 and about 664 µmol/m2 (e.g., Compound (1) in about 233-266 mg/m2) of the bis(thiohydrazide amide) once every 3 weeks. In certain embodiments, the bis(thiohydrazide amide) is in an amount of about 664 µmol/m2 (e.g., Compound (1) in about 266 mg/m2).

In another dosage regimen, the subject can be intravenously administered between about 200 µmol/m2 to about 263 µmol/m2 of the taxane as paclitaxel once every 3 weeks (e.g., paclitaxel in about 175-225 mg/m2). In some embodiments, the subject can be intravenously administered between about 200 µmol/m2 to about 234 µmol/m2 of the taxane as paclitaxel once every 3 weeks (e.g., paclitaxel in about 175-200 mg/m2). In certain embodiments, the paclitaxel is administered in an amount of about 234 µmol/m2 (200 mg/m2). In certain embodiments, the paclitaxel is administered in an amount of about 205 µmol/m2 (175 mg/m2).

In one embodiment, the taxane, e.g., paclitaxel, and the bis(thiohydrazide amide), e.g., Compound (1), can be administered together in a single pharmaceutical composition.

In one embodiment, the method of the present invention includes treating a subject once every three weeks, independently or together a taxane in an amount of about 205 µmol/m2 (e.g., paclitaxel in about 175 mg/m2); and a bis(thiohydrazide amide) represented by Structural Formula I or a pharmaceutically acceptable salt or solvate thereof in an amount between about 220 µmol/m2 and about 1310 µmol/m2 (e.g., Compound (1) in about 88-525 mg/m2). Typically, the taxane is paclitaxel intravenously administered in an amount of about 205 µmol/m2. The bis(thiohydrazide amide) can typically be intravenously administered between about 220 µmol/m2 and about 1093 µmol/m2 (e.g., Compound (1) in about 88-438 mg/m2), more typically between about 749 µmol/m2 and about 999 µmol/m2 (e.g., compound (I) in about 300-400 mg/m2), in some embodiments between about 811 µmol/m2 and about 936 µmol/m2 (e.g., Compound (1) in about 325-375 mg/m2). In certain embodiments, the bis(thio-hydrazide amide) can be Compound (1) intravenously administered between about 874 µmol/m2 (about 350 mg/m2).

In a particular embodiment, the methods of the present invention involve intravenously administering to the subject in a single dose per three week period: paclitaxel in an amount of about 205 µmol/m2 (175 mg/m2); and Compound (1) or a pharmaceutically acceptable salt or solvate thereof in an amount of about 874 µmol/m2 (350 mg/m2).

Particular formulations, dosages and modes of administration are as described in US Publication No. 20060135595 and PCT/US2006/014531 filed 13 Apr. 2006, titled Combination Cancer Therapy With Bis[Thiohydrazide] Amide Compounds the entire contents of each of which are incorporated herein by reference).

The bis(thio-hydrazide amide) disclosed herein can be prepared by the methods described in U.S. Publication Nos. 20060135595, 2003/0045518 and 2003/0119914, U.S. application Ser. No. 11/432,307, filed 11 May 2006, titled Synthesis Of Bis(Thio-Hydrazide Amide) Salts, U.S. Provisional Patent No. 60/708,977 filed 16 Aug. 2005, titled Bis(Thio-Hydrazide Amide) Formulation and also according to methods described in U.S. Publication No. 2004/0225016 A1, entitled TREATMENT FOR CANCERS. The entire teachings of these applications are incorporated herein by reference.

The present invention is illustrated by the following examples, which are not intended to be limiting in any way.

EXEMPLIFICATION

Example 1

Weekly Treatment Regimen of Compound (I) and Paclitaxel Combined in Stage 1V Metastatic Melanoma Patients in Comparison with Paclitaxel Alone, Based on Time to Progression A total of 81 people with Stage 1V melanoma were tested in a randomized trial with ratios of 2:1, compound (I)+paclitaxel (53 people): paclitaxel alone (28 people). The dosages administered were 213 mg/m² compound (I), 80 mg/m² paclitaxel, and the dosage regimen was 3 weekly doses per each 4 week cycle. Patients were treated until progression of the disease. Patients who progressed on paclitaxel alone were given the option to crossover to compound (I)+paclitaxel and were treated until progression. The tumor assessments were performed at baseline, Cycle 2, and every other Cycle thereafter.

The baseline grades of metastatic diseases of the patients are shown below:

|  | compound (1) + Paclitaxel (n = 53) | Paclitaxel (n = 28) |
|---|---|---|
| M1a - metastasis to distant skin and subcutaneous tissue | 7 (13%) | 2 (7%) |
| M1b - metastasis to lungs | 18 (34%) | 5 (18%) |
| M1c - metastasis to other distant organs, such as liver and brain | 28 (53%) | 21 (75%) |

Though the majority of the patients in the paclitaxel alone treatment group were M1c, an analysis of the effect of M grade did not show a statistically significant effect on the patient's likelihood of progressing more quickly (p-value=0.5368). The actual treatment the patient received did have a statistically significant effect on the patient's likelihood of progressing more quickly (p-value=0.0281).

The probability-value for the continuum of potential outcomes was divided into four scenarios from best to worst:
  i) Inverted or Equal results;
  ii) 4783 better p>0.2;
  iii) Favorable 0.05<p<0.2 to; and
  iv) Favorable p<0.05.

Table 1 shows the Kaplier Meyer estimates of the Time to Progression of the disease (Efficacy Sample):

TABLE 1

| Time to Progression (days) | compound (1) + Paclitaxel (n = 50) | Paclitaxel (n = 27) | p-value* |
|---|---|---|---|
| 25th percentile (95% confidence interval (CI)) Median (95% CI) 75th percentile (95% CI) | 54.0 (49.0, 95.0) 134.0 (86.0, 217.0 273.0 (168.0, 331.0) | 49.0 (29.0, 52.0) 56.0 (49.0, 105.0) 106.0 (61.0, 218.0) | 0.017 |

The p-value is from a log-rank test

Based on the four scenarios above the study results are in line with the best of the four possible scenarios.

Table 2 shows the best overall response per Response Evaluation Criteria In Solid Tumors (RECIST) (Efficacy Sample)

TABLE 2

|  | compound (1) + Paclitaxel (n = 50) | Paclitaxel (n = 27) | p-value* |
|---|---|---|---|
| Best Overall Response |  |  |  |
| Complete Response (CR) | 1 (2.0%) | 0 |  |
| Partial Response (PR) | 7 (14.0%) | 1 (3.7%) |  |
| Stable Disease (SD) | 25 (50.0%) | 10 (37%) |  |
| Progressive Disease (PD) | 17 (34.0%) | 16 (59.3%) |  |
| Two-Sided Fisher's Exact Test |  |  |  |
| CR + PR (95% CI) | 16.0% (7.2%, 29.1%) | 3.7% (0.1%, 19.0%) | 0.149 |

As can be seen from Table 2 compounds of the present invention in combination with paclitaxel show a significant improvement over paclitaxel alone. Specifically compounds of the present invention in combination with paclitaxel showed one patent with a complete response and over 50% of the patients had stable disease compared with Paclitaxel alone which only showed 37% of the patients with stable disease.

Tables 3 and 4 show the relative treatment results of compound (1) in combination with Paclitaxel compared with Paclitaxel alone and other currently used treatments for melanoma. As can be seen from Tables 3 and 4 the number of days to progression of the disease is greatly enhanced for compound (1) in combination with Paclitaxel compared with Paclitaxel alone. In addition the time to progression benefit is much better than any single-agent therapy and much better than all but one combination therapy.

The combination therapy, cisplatin vinblastine dacarbazine IL-2 and IFN, which had a longer time to progression than compound (1) in combination with Paclitaxel, however, has severe side effects and requires patients to be hospitalized for administration of the combination. Conversely, compound (1) in combination with Paclitaxel only showed a mild increase in the side effects over Paclitaxel alone. None of the side effect were sever enough to cause any patients to discontinue treatment with compound (1) in combination with Paclitaxel during the trial.

TABLE 3

| Agent/Regimen | CR (%) | PR (%) | OR (%) | TTP (days) | Survival (months) |
|---|---|---|---|---|---|
| Natural disease progression | | | | | 6-9 |
| "Any Treatment" | | | 5-10 | | |
| Single-Agent Chemotherapy | | | | | |
| DTIC (dacarbazine) | rare <3 | | 10-20 | | no improvement |
| Temozolomide (Temodar) | 2.6 | 9.6% | 13.5 | 58 | 7.7 |
| Paclitaxel (Taxol) | | | 12, 17.8 | | |
| Paclitaxel | 0 | 3.7 | 3.7 | 57 | N.D. |
| Fotemustine | | | 15.2 | 55 | 7.3 |
| Sorafenib | | 2.6 | | | |
| Anti-Estrogen Therapy | | | | | |
| Tamoxifen | 1 | 3.9 | 4.9 | | |

TABLE 4

| Agent/Regimen | CR (%) | PR (%) | OR (%) | TTP (days) | Survival (months) |
|---|---|---|---|---|---|
| Natural disease progression | | | | | 6-9 |
| "Any Treatment" | | | 5-10 | | |
| Biologic Response Modifiers | | | | | |
| Interleukin-2 (IL-2; Proleukin ®) | 6 | 10 | 14.3, 16 | | 8.7,<12 |
| Interferon (IFN alfa-2b, IFN) | 3-5 | | 15 | | |
| Biochemotherapy | | | | | |
| INF in combination | | | 24 | | |
| MDX-010 + IL-2 | 5.6 | 16.7 | 22.2 | | |
| MDX-010 + MDX-1379 | 3.6 | 8.9 | 12.5 | | |
| Dacarbazide + Genasense | | | 11.7 | 78 | 9.1 |
| Dacarbazide + Cisplatin + IFN | | | | 92 | 9 |
| Dacarbazide + Cisplatin + IFN + IL-2 | | | | 119 | 9 |
| Paclitaxel +: compound (1) | 2.0 | 14.0 | 16 | 134 | N.D. |
| Cisplatin + vinblastine + dacarbazine + IL-2 + IFN | 6.6 | | | 149 | 11.9 |
| Carmustine + dacarbazine + cisplatin + Nolvadex + IL-2 + IFN | 13 | 30 | 43 | | | cisplatin vinblastine dacarbazine IL-2 and IFN

Example 2

Compounds of the Invention Accumulate in the Kidneys

A study was designed to investigate the tissue distribution of compounds (1) and (18) in SW female mice, N=2 per group (total 4 groups including vehicle control. Reagents were obtained from Sigma, St Louis, Mo.; mice were obtained from Taconic Farms (Germantown N.Y.). The vehicle employed was 10% DMSO, 18% Cremophor RH40. The compounds were administered intravenously at a dose of 25 mg/kg. Blood was collected 30 min after administration, and tissue collection was performed immediately after blood collection. Plasma samples were prepared by combining 50 μL plasma+50 μL1% dithiothreitol (DTT)+150 μL $CH_3CN$ (0.1% HCOOH), centrifuged at 10,000 rpm×5 min; 150 μL supernatant+90 μL $H_2O$. Tissue samples were prepared by homogenizing a weighed tissue sample in phosphor-buffered saline (PBS, ×1)+1% DTT (×1)+$CH_3CN$ (0.1% HCOOH) (×3)), centrifuged at 10,000 rpm×5 min; 150 μL supernatant+ 90 μL $H_2O$. 100 μL prepared samples were subjected to HPLC, using 5-95% $CH_3CN$ (0.1% HCOOH) as the eluent. The running time was 15 min. With this method, the retention times were 7.25 min for compound (18) and 7.99 min for compound (I).

Figure 2:
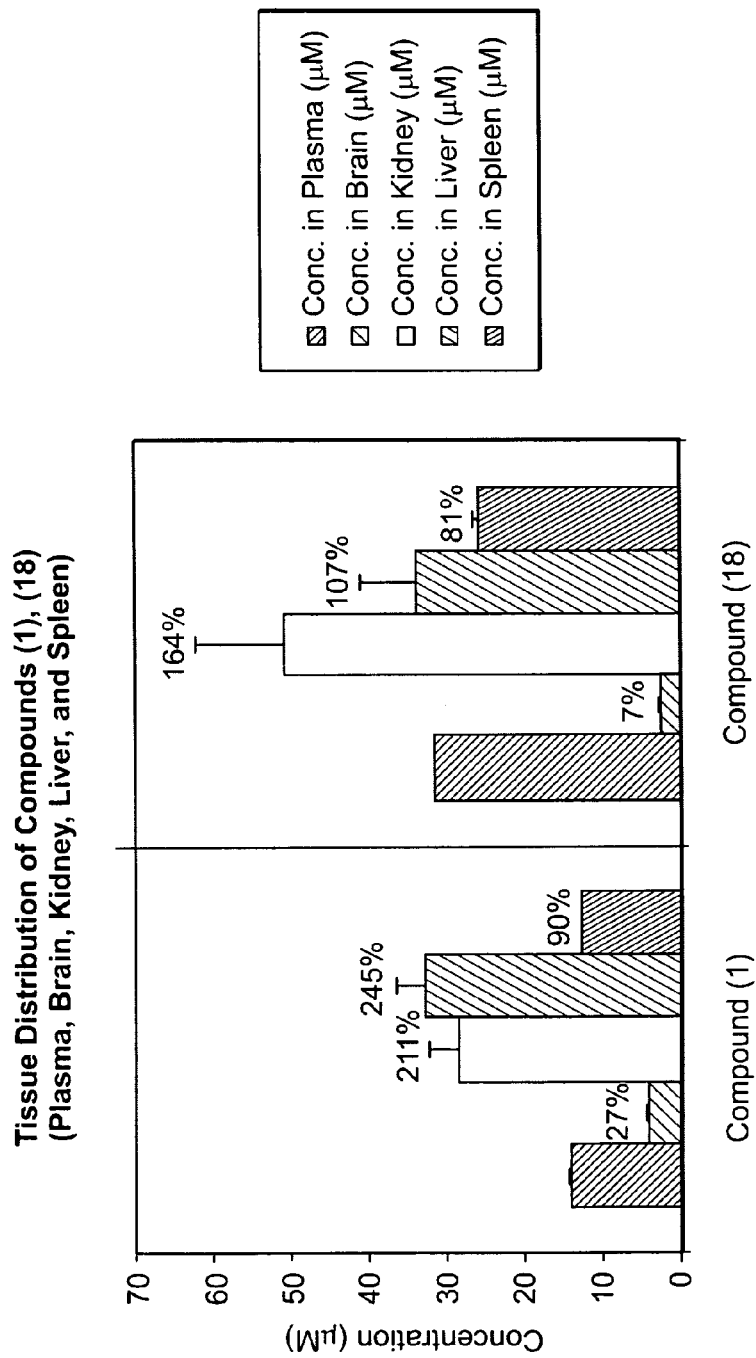
FIG. 2 is a graph of the tissue distribution of compound (I) and compound (18).

FIG. 1 is a bar graph showing the concentrations of compound (1) and compound (18) in mouse plasma, brain, kidney, liver and spleen measured 30 min after injection in a first experiment. FIG. 2 is a graph of the tissue distribution of compound (1) and compound (18). Compound (1) was detected in the kidney at concentrations of about 28 μM which was about 211% of the plasma. Compound (18) was detected in kidney at a concentration of about 51 μM, which was about 164% of the plasma concentration. Therefore, both compounds effectively accumulate in the kidneys.

Example 3

Direct Evidence that Compound 1 Induces the Generation of ROS in Drug-Treated Cells We performed a series of experiments to directly show that Compound 1 induces the generation of ROS in drug-treated cells. In these experiments, we monitored the production of ROS using the cell permeable Carboxy-$H_2$DCFDA probe. When this probe is oxidized by ROS, it emits a green fluorescence that can be detected using flow cytometry or fluorescent microscopy. Ramos cells were treated with Compound 1 (0.5 μM) for 24 hours or pre-treated with 1.0 mM or 10 mM NAC for 1 hour prior to addition of Compound 1 was then washed gently once with warm HBSS/Ca/Mg (GIBCO.14025). 25 μM carboxy-$H_2$DCFDA (Invitrogen. C400) working solution was added to cover the cells, and the cells were incubated for 30 minutes at 37° C., protected from light. The cells were gently washed three times in warm HBSS/Ca/Mg. ROS levels, as determined by fluorescence intensity, were determined by flow cytometry (excitation at 495 nm, emission at 529 nm).

Figure 3:
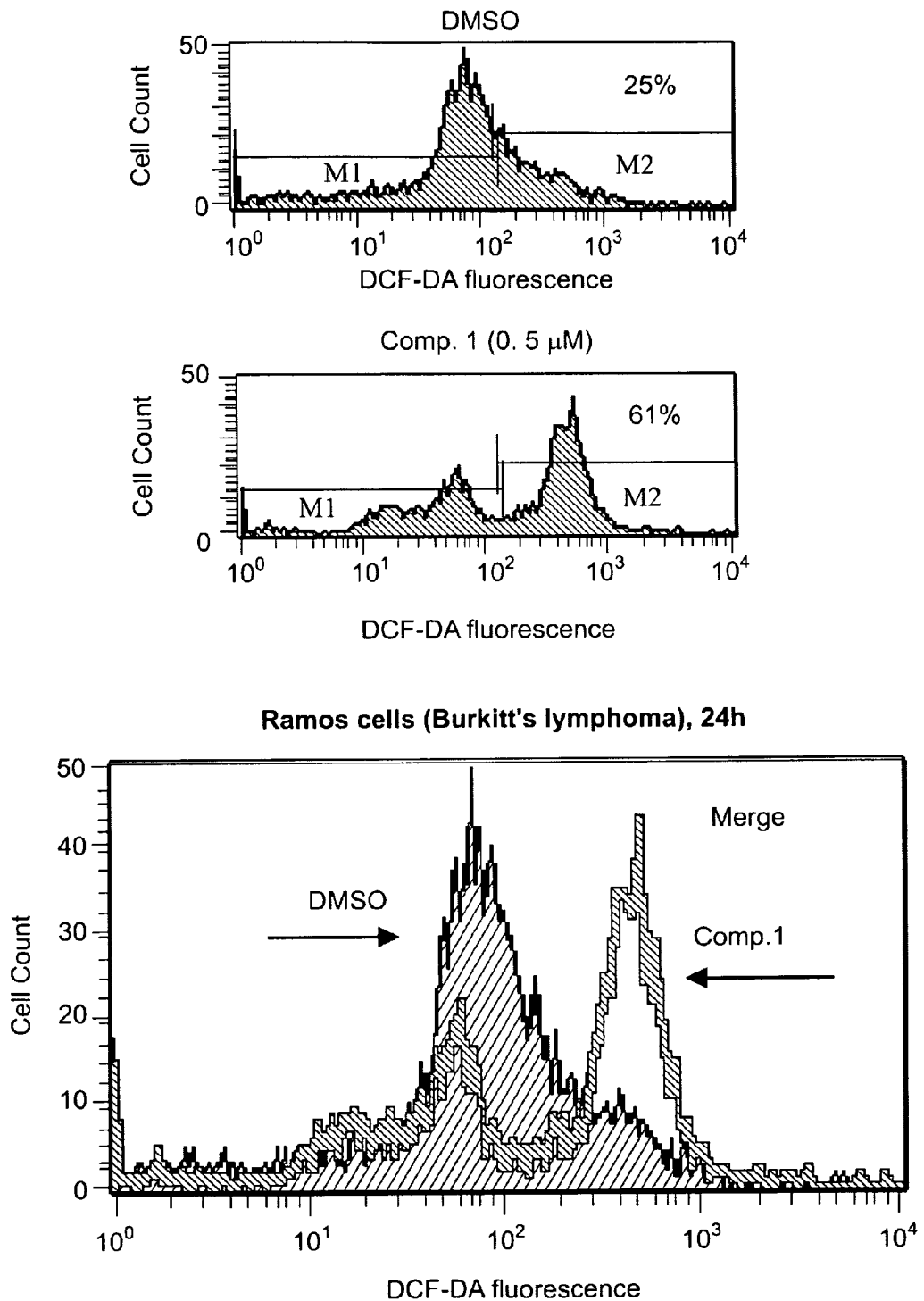
FIG. 3 is a graph showing that Ramos cells treated with Compound 1 emit more reactive oxygen species than cells treated with DMSO alone. The production of reactive oxygen species by the cells was measured using a cell permeable DCF-DA probe which, when oxidized by reactive oxygen species, emits a green fluorescence that was detected by flow cytometry.
Figure 4:
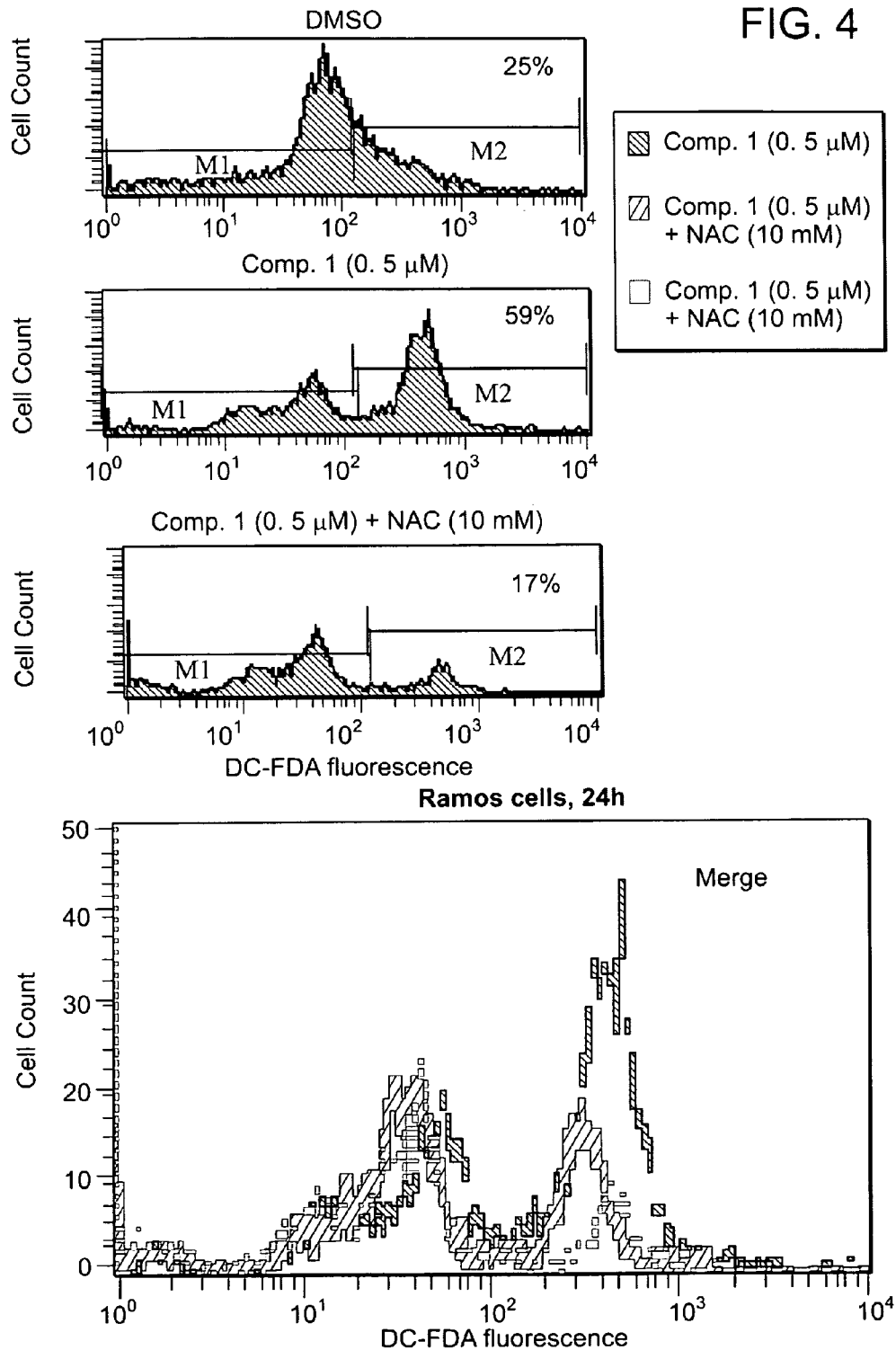
FIG. 4 is a graph showing that induction of reactive oxygen species by Compound 1 can be blocked by treating Ramos cells with NAC in combination with Compound 1. The production of reactive oxygen species was measured using a DCF-DA probe and detected using flow cytometry.
Figure 5:
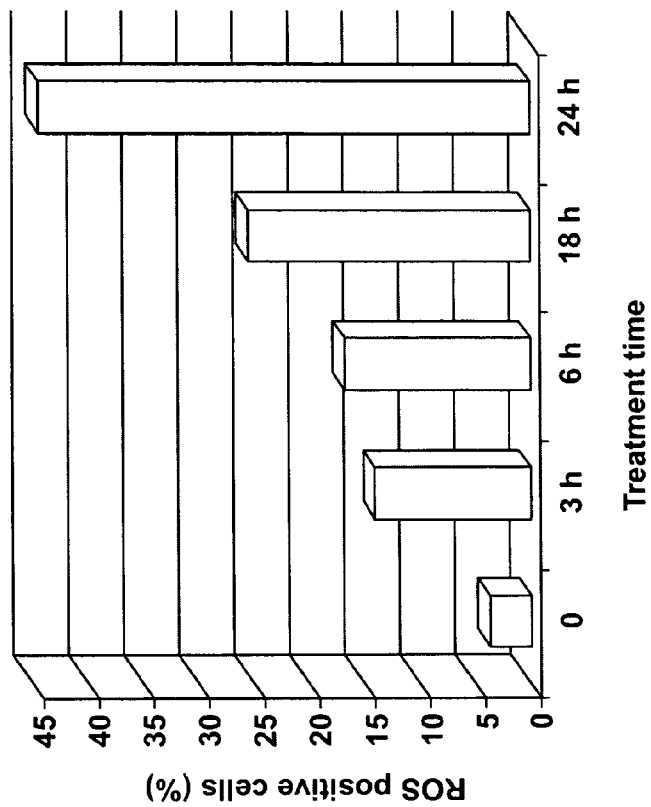
FIG. 5 is a graph showing that Compound 1 induced the production of reactive oxygen species in Ramos cells in a time dependent manner. The production of reactive oxygen species was measured using a DCF-DA probe and detected using flow cytometry.
Figure 5:
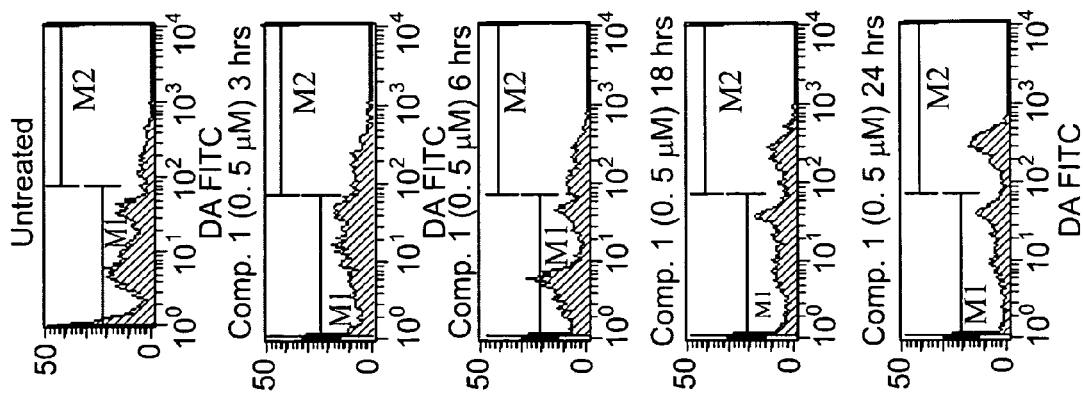
Figure 6:
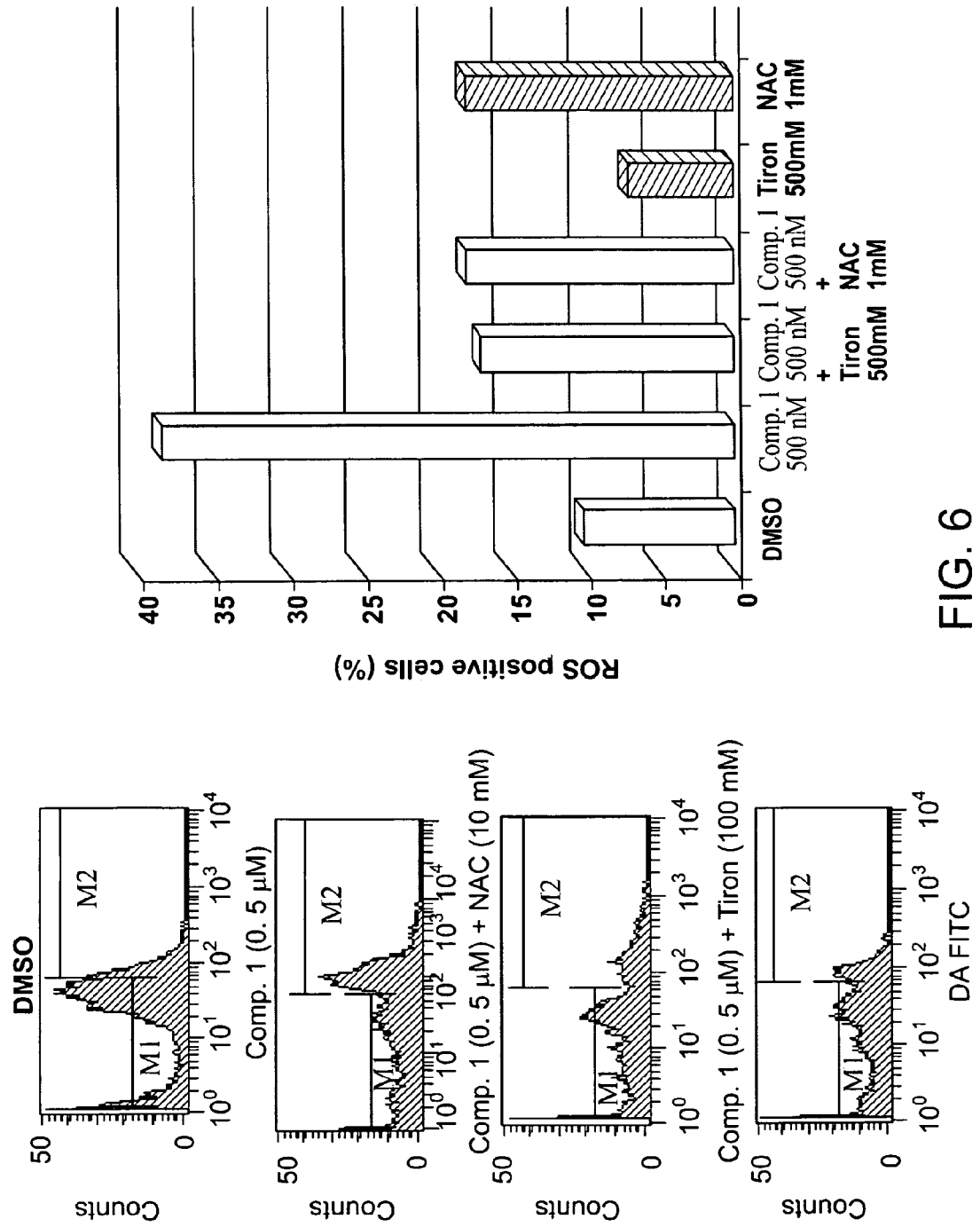
FIG. 6 is a graph showing both Tiron and NAC block the production of reactive oxygen species induced by treatment of cells with Compound 1. Tiron and NAC are antioxidants that function by different mechanisms. The production of reactive oxygen species was measured using a DCF-DA probe and detected using flow cytometry.

Treatment of Ramos cells for 24 hours with Compound 1 induced the generation of ROS in cells resulting in the oxidation and activation of the Carboxy-$H_2$DCFDA probe (FIG. 3). Treatment of drug-treated cells with NAC almost completely blocked the generation of ROS by Compound 1 (FIG. 4). Compound 1 induced ROS in a time dependent manner and induction of ROS was observed as early as 3 hours (FIG. 5). These data indicate that Compound 1 induces oxidative stress and ROS generation in drug-treated cells.

Example 4

The Free-Radical Scavenger Tiron also Blocks ROS Generation and Hsp70 Induction by Compound 1

Figure 7:
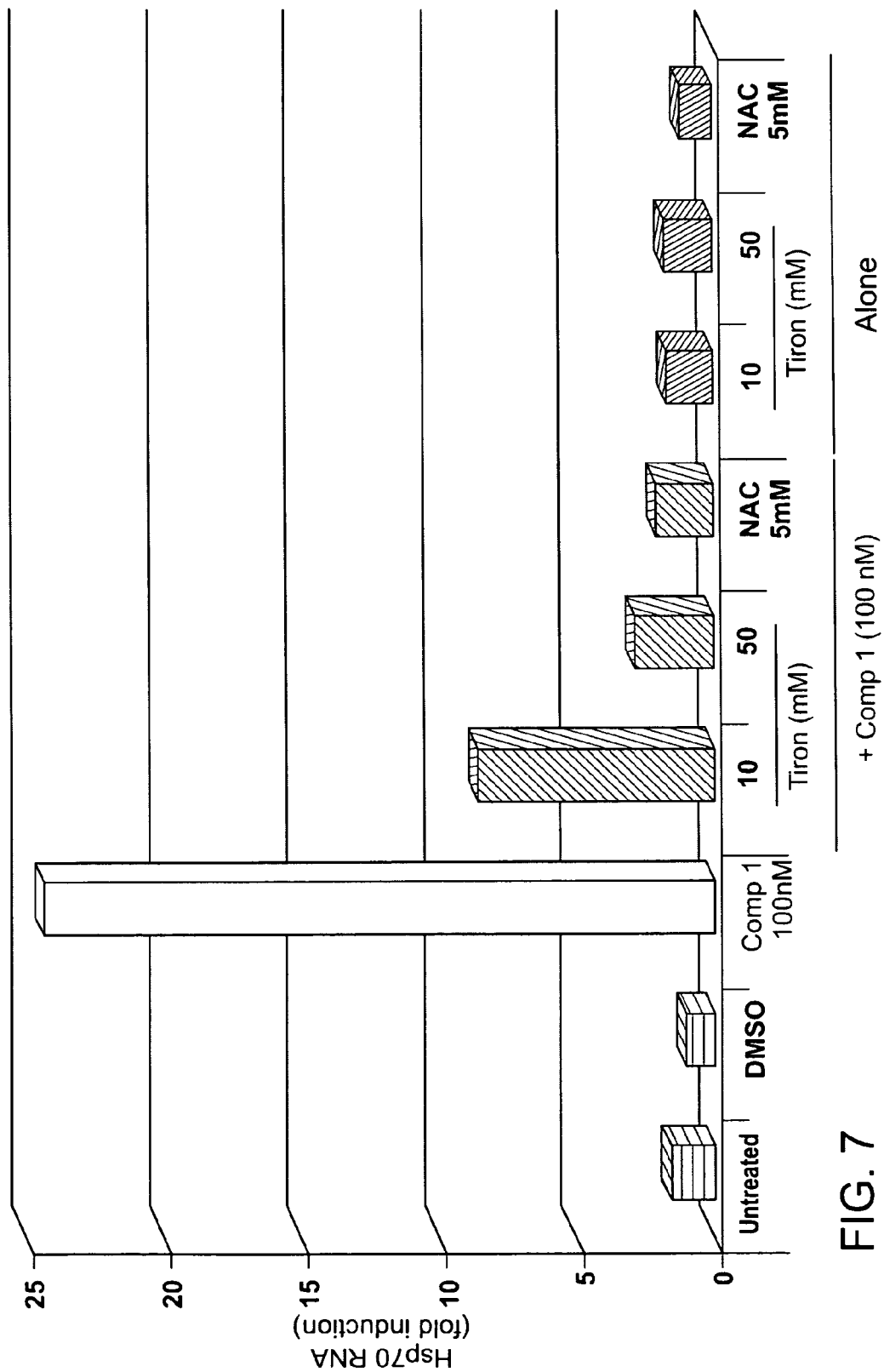
FIG. 7 is a graph showing Tiron blocks the induction of Hsp70 by Compound 1.

Tiron is a direct scavenger of ROS and is a potent inhibitor of oxidative stress. Ramos cells were pre-treated with 500 mM Tiron 1 hour prior to addition of Compound 1 (0.5 μM) for 24 hours, then measurement of ROS levels was performed as in Example 3. The addition of Tiron to Compound I-treated cells blocked the ability of Compound 1 to generate ROS (FIG. 6) and induce Hsp70 (FIG. 7). These data demonstrate that multiple antioxidants with differing mechanisms of action can block the activity of Compound 1.

Example 5

Compound 1 Enhances the Anti-Tumor Activity of Ionizing Radiation Against Human Tumor Cells in a Mouse Xenograft Model The human squamous non-small cell lung cancer cell line, RERF-LC-AI (RCB0444; S. Kyoizumi, et al., *Cancer Res.* 45:3274-3281, 1985), was obtained from the Riken Cell Bank (Tsukubua, Ibaraki, Japan). The cells were cultured in growth media prepared with Iscove's Modified Dulbecco's Media, 10% fetal bovine serum (FBS), 1% 100× Penicillin-Streptomycin, 1% 10×L-glutamine, 1% 10× sodium pyruvate and 1% 100×MEM non-essential amino acids. FBS was obtained from American Type Culture Collection (Manassas, Va., USA) and all other reagents were obtained from Invitrogen Corp. (Carlsbad, Calif., USA). Cells that had been cryopreserved in liquid nitrogen were rapidly thawed at 37° C. and transferred to a tissue culture flask containing growth media and then incubated at 37° C. in a 5% $CO_2$ incubator. To expand the cell line, growth media was replaced every 2-3 days until the flask became 90% confluent, typically in 5-7 days. Cultures were passaged by washing with 10 mL of room temperature phosphate buffered saline (PBS) and then disassociating cells by adding 5 mL 1× trypsin-EDTA and incubating at 37° C. until the cells detached from the surface of the flask. To inactivate the trypsin, 5 mL of growth media was added and then the contents of the flask were centrifuged to pellet the cells. The supernatant was aspirated and the cell pellet was resuspended in 10 mL of growth media and the cell number determined using a hemocytometer. Approximately 1-3×$10^6$ cells per flask were seeded into 175 $cm^2$ flasks containing 50 mL of growth media and incubated at 37° C. in a 5% $CO_2$ incubator. When the flasks reached 90% confluence, the above passaging process was repeated until sufficient cells had been obtained for implantation into mice.

Seven to eight week old, female homozygous Crl:CD1-Foxn1$^{nu/nu}$ (Nude) mice were obtained from Charles River Laboratories (Wilmington, Mass., USA). Animals were housed 4-5/cage in micro-isolators, with a 12 hr/12 hr light/dark cycle, acclimated for at least 1 week prior to use and fed normal laboratory chow ad libitum. Studies were conducted on animals between 9-10 weeks of age at implantation. To implant RERF-LC-AI tumor cells into Nude mice, cell cultures were trypsinized as above, washed in PBS and resuspended at a concentration of 5×$10^7$ cells/mL in 50% growth media and 50% Matrigel Basement Membrane Matrix (#354234; BD Biosciences; Bedford, Mass., USA). Using a 27 gauge needle and 1 cc syringe, 0.1 mL of the cell suspension was injected subcutaneously into the flanks of Nude mice. Tumor volumes (V) were calculated by caliper measurement of the width (W), length (L) and thickness (T) of tumors using the following formula: V=0.5236×(L×W×T).

In vivo passaged RERF-LC-AI tumor cells (RERF-LC-AI$^{IVP}$) were isolated to improve the rate of tumor implantation relative to the parental cell line in Nude mice. RERF-LC-AI tumors were permitted to develop in vivo until they reached approximately 250 $mm^3$ in volume, which required approximately 3 weeks following implantation. Mice were euthanized via $CO_2$ asphyxiation and their exteriors sterilized with 70% ethanol in a laminar flow hood. Using sterile technique, tumors were excised and diced in 50 mL PBS using a scalpel blade. A single cell suspension was prepared using a 55 mL Wheaton Safe-Grind tissue grinder (catalog #62400-358; VWR International, West Chester, Pa., USA) by plunging the pestle up and down 4-5 times without twisting. The suspension was strained through a 70 μM nylon cell strainer and then centrifuged to pellet the cells. The resulting pellet was resuspended in 0.1 M $NH_4Cl$ to lyse contaminating red blood cells and then immediately centrifuged to pellet the cells. The cell pellet was resuspended in growth media and seeded into 175 $cm^2$ flasks containing 50 mL of growth media at 1-3 tumors/flask or approximately 1×$10^7$ cells/flask. After overnight incubation at 37° C. in a 5% $CO_2$ incubator, non-adherent cells were removed by rinsing two times with PBS and then the cultures were fed with fresh growth media. When the flasks reached 90% confluence, the above passaging process was repeated until sufficient cells had been obtained for implantation into mice as described above.

RERF-LC-AI$^{IVP}$ tumors were then permitted to develop in vivo until the majority reached 90-230 $mm^3$ in tumor volume, which required approximately 3 weeks following implantation. Animals with oblong, very small or large tumors were discarded, and only animals carrying tumors that displayed consistent growth rates were selected for studies. Animals were randomized into treatment groups so that the average tumor volumes of each group were similar at the start of dosing. % T/C values, as a measure of efficacy, were determined as follows:
(i) If ΔT>0: % T/C=(ΔT/ΔC)×100
(ii) If ΔT<0: % T/C=(ΔT/T$_0$)×100
(iii) ΔT=Change in average tumor volume between start of dosing and the end of study.
(iv) ΔC=Change in average tumor volume between start of dosing and the end of study.
(v) T$_0$=Average tumor volume at start of dosing.

To formulate Compound 1 in 10/18 DRD, stock solutions of the test article were prepared by dissolving the appropriate amounts of the compound in dimethyl sulfoxide (DMSO) by sonication in an ultrasonic water bath. Stock solutions were prepared weekly, stored at −20° C. and diluted fresh each day for dosing. A solution of 20% Cremophor RH40 (polyoxyl 40 hydrogenated castor oil; BASF Corp., Aktiengesellschaft, Ludwigshafen, Germany) in 5% dextrose in water (D5W; Abbott Laboratories, North Chicago, Ill., USA) was also prepared by first heating 100% Cremophor RH40 at 50-60° C. until liquefied and clear, diluting 1:5 with 100% D5W, reheating again until clear and then mixing well. This solution was stored at room temperature for up to 3 months prior to use. To prepare 10/18 DRD formulations for daily dosing, DMSO stock solutions were diluted 1:10 with 20% Cremophor RH40. The final 10/18 DRD formulation for dosing contained 10% DMSO, 18% Cremophor RH40, 3.6% dextrose, 68.4% water and the appropriate amount of test article. Animals were intravenously (i.v.) injected with this formulation at 10 mL per kg body weight on five days each week (Monday, Tuesday, Wednesday, Thursday, Friday) for a total of 15 doses.

Animals were irradiated using a calibrated $^{137}$Cs gamma-ray (0.662 MeV) Model 30 Mark I irradiator (J.L. Shepherd & Associates, San Fernando, Calif., USA). Tumor-bearing animals were anesthetized for approximately 4 minutes with inhaled isoflurane (IsoFlo, Abbott Laboratories, North Chicago, Ill., USA) delivered on a stream of oxygen at 0.8 L/min and 3% volume/volume on a mobile anesthesia machine (Vet-Equip, Pleasanton, Calif., USA). This resulted in sufficient anesthesia to immobilize the animals for placement of each group of 4-5 animals into the irradiator, but the effect typically wore off 1-2 minutes prior to completion of irradiation for that group. Anesthetized animals were positioned in the irradiator approximately 3 cm in front of the $^{137}$Cs source using a restraint device capable of holding 5 animals (J.L Shepherd & Associates). Ionizing radiation was focused on the subcutaneously implanted RERF-LC-AI$^{IVP}$ tumors through a 1 cm wide collimator (J.L. Shepherd & Associates) placed in front of the $^{137}$Cs source. Animals were irradiated at 1.6 Gy (160 rad) per minute. Dosimetry demonstrated an approximately 450:1 ratio of focused radiation received by tumors relative to the head and shoulder region of animals.

Figure 8:
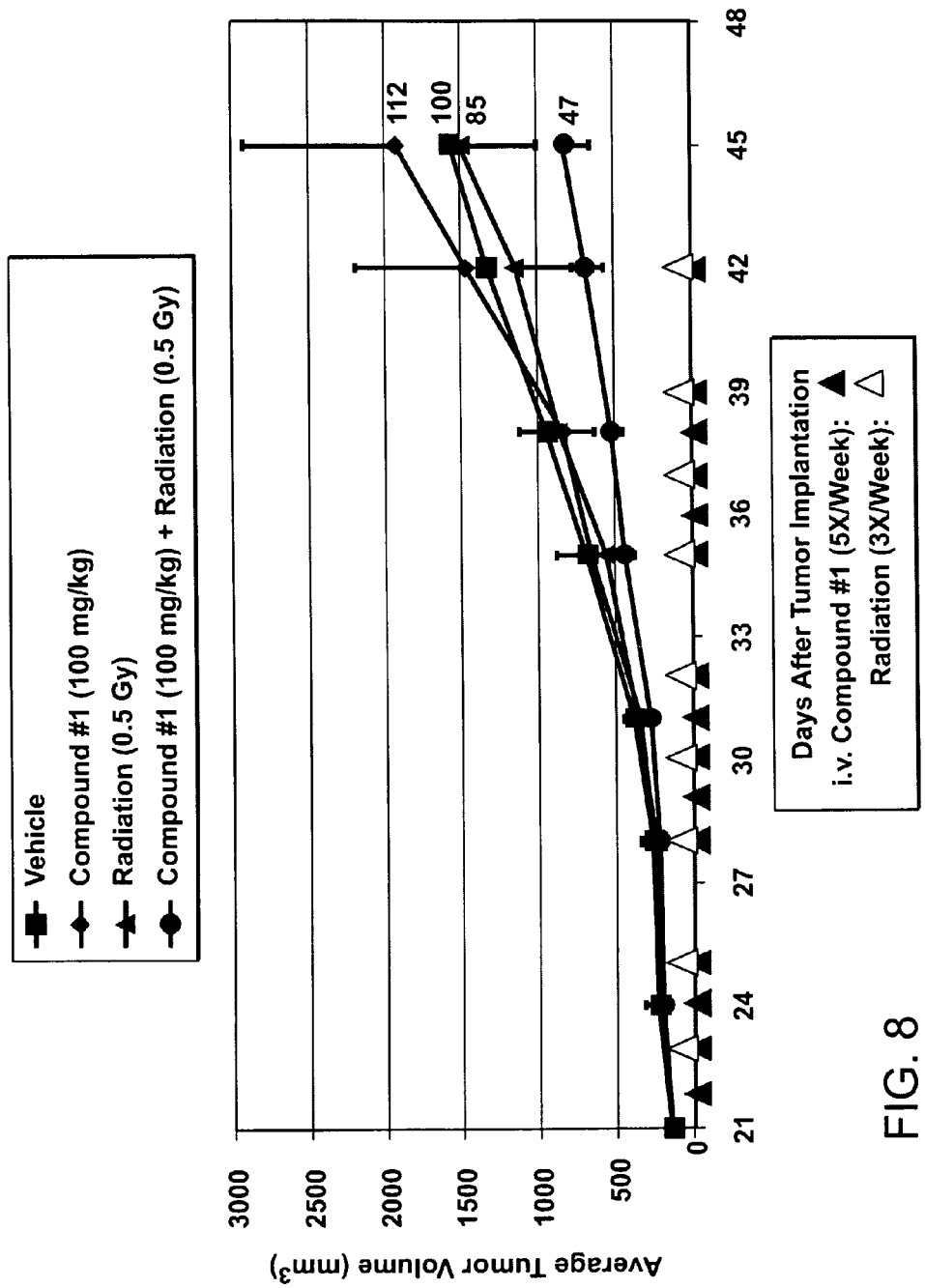
FIG. 8 shows the results of a Nude mouse xenograft study to determine the effect of Compound 1 on the in vivo growth rate of RERF-LC-AI$^{IVP}$ human lung tumor cells when dosed in combination with fractionated ionizing radiation. Tumor-bearing animals (8 mice/group) were i.v. injected 5 times per week for a total of 15 doses (closed arrowheads) with 10 mL/kg of 10/18 DRD vehicle with or without 100 mg/kg Compound 1. Animals were also irradiated 3 times per week for a total of 9 doses (open arrowheads) with 0.5 Gy radiation. In the combination treatment group, animals were irradiated 420 min prior to being dosed with Compound 1. Each group that was not dosed with Compound 1 was instead dosed with 10/18 DRD vehicle as a mock treatment. Each group that was not irradiated was instead anesthetized and restrained as a mock irradiation. Average tumor volumes for each group were determined every 3-4 days (error bars represent + or −0.5 SEM; error bars not shown the vehicle group for clarity). Treatment with a combination of 0.5 Gy radiation, delivered three times per week, in combination with 100 mg/kg Compound 1, dosed five times per week, substantially inhibited tumor growth in relative to that achieved by either single therapy alone. % T/C values are indicated on the right.

We investigated the ability of Compound 1 to enhance the in vivo anti-tumor activity of ionizing radiation. As shown in FIG. 8, treatment with neither 100 mg/kg Compound 1 dosed 5 times per week, nor irradiation with 0.5 Gy ionizing radiation delivered 3 timers per week, resulted in significant reductions in the growth rate of RERF-LC-AI$^{IVP}$ cells in Nude mice, with % T/C values of 112 and 85, respectively. However, treatment with 0.5 Gy radiation delivered 3 times per week, combined with 100 mg/kg Compound 1 dosed 5 times per week (Compound 1 was dosed 420 minutes after irradiation), substantially decreased the growth rate of RERF-LC-AI$^{IVP}$ cells in Nude mice, with a % T/C value of 47. This effect was not associated with excessive toxicity, as each treatment group had average bodyweight gains relative to the start of the study of between +3.4% and +6.0% over the course of the study.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of treating a subject with a non-small cell lung cancer, said method comprising administering to the subject an effective amount of a compound represented by the following Structural Formula:

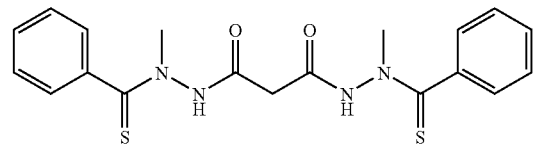

or a pharmaceutically acceptable salt thereof, in combination with radiotherapy, wherein the compound and the radiotherapy are the only anticancer therapies administered to the subject during the treatment.

2. The method of claim 1, wherein the compound is represented by the following structural formula:

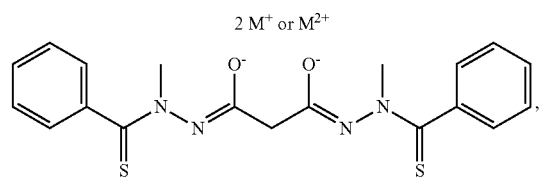

wherein M$^+$ is a pharmaceutically acceptable monovalent cation and M$^{2+}$ is a pharmaceutically acceptable divalent cation.

3. The method of claim 2, wherein the pharmaceutically acceptable monovalent cation is Na$^+$ or K$^+$.

4. The method of claim 3, wherein the compound is represented by the following structural formula:

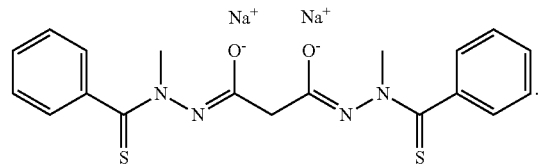

* * * * *